(12) United States Patent
Bogatcheva et al.

(10) Patent No.: US 7,884,097 B2
(45) Date of Patent: Feb. 8, 2011

(54) METHODS AND COMPOSITIONS COMPRISING DIAMINES AS NEW ANTI-TUBERCULAR THERAPEUTICS

(75) Inventors: Elena Bogatcheva, Bethesda, MD (US); Marina Protopopova, Silver Spring, MD (US); Boris Nikonenko, Rockville, MD (US)

(73) Assignee: Sequella, Inc., Rockville, MD (US)

( * ) Notice: Subject to any disclaimer, the term of this patent is extended or adjusted under 35 U.S.C. 154(b) by 1514 days.

(21) Appl. No.: 10/936,217

(22) Filed: Sep. 7, 2004

(65) Prior Publication Data

US 2005/0113574 A1 May 26, 2005

Related U.S. Application Data

(60) Provisional application No. 60/500,531, filed on Sep. 5, 2003.

(51) Int. Cl.
*A61K 31/00* (2006.01)
*A61K 31/50* (2006.01)

(52) U.S. Cl. .................. 514/218; 514/247; 514/211.08

(58) Field of Classification Search .............. 514/231.2, 514/315, 255.03, 306, 317, 649, 653, 654, 514/655, 659, 660, 408, 326, 667
See application file for complete search history.

(56) References Cited

U.S. PATENT DOCUMENTS

| | | | |
|---|---|---|---|
| 2,623,878 A | 12/1952 | Isler et al. |
| 2,709,169 A | 5/1955 | Morren et al. |
| 3,176,040 A | 3/1965 | Wilkinson et al. |
| 3,197,468 A * | 7/1965 | Sensi et al. ................. 540/458 |
| 3,553,257 A | 1/1971 | Halmos et al. |
| 3,579,586 A | 5/1971 | Zoja |
| 3,579,587 A | 5/1971 | Zoja |
| 3,629,333 A | 12/1971 | Boughton et al. |
| 3,682,922 A | 8/1972 | Klimstra et al. |
| 3,718,655 A | 2/1973 | Ferrer-Salat et al. |
| 3,769,347 A | 10/1973 | Kazan |
| 3,789,073 A | 1/1974 | Narayanan et al. |
| 3,829,493 A | 8/1974 | Butula et al. |
| 3,847,991 A | 11/1974 | Bernardi et al. |
| 3,855,300 A | 12/1974 | Takahashi et al. |
| 3,876,702 A | 4/1975 | Petersen et al. |
| 3,878,201 A | 4/1975 | Tomcufcik |
| 3,931,152 A | 1/1976 | Tomcufcik et al. |
| 3,931,157 A | 1/1976 | Child et al. |
| 3,944,608 A | 3/1976 | Singh |
| 3,944,616 A | 3/1976 | Kazan |
| 3,944,617 A | 3/1976 | Singh |
| 3,944,618 A | 3/1976 | Singh |
| 3,944,619 A | 3/1976 | Singh |
| 3,953,513 A | 4/1976 | Oppici |
| 3,979,457 A | 9/1976 | Fujii et al. |
| 4,006,234 A | 2/1977 | Child et al. |
| RE29,358 E | 8/1977 | Tomcufcik |
| RE29,588 E | 3/1978 | Halmos et al. |
| 4,150,030 A | 4/1979 | Singh |
| 4,262,122 A | 4/1981 | Lees et al. |
| 4,450,274 A | 5/1984 | Park |
| 4,457,931 A | 7/1984 | Milani et al. |
| 5,104,875 A | 4/1992 | Jürgen et al. |
| 5,256,391 A | 10/1993 | Chen et al. |
| 5,439,891 A | 8/1995 | Kapil et al. |
| 5,864,045 A | 1/1999 | Burholder et al. |
| 5,922,282 A | 7/1999 | Ledley |
| 5,985,935 A | 11/1999 | Kharazmi et al. |
| 6,300,061 B1 | 10/2001 | Jacobs, Jr. et al. |
| 6,660,744 B1 | 12/2003 | Hirst |
| 7,456,222 B2 | 11/2008 | Protopopova et al. |
| 2002/0007524 A1 | 1/2002 | Sorensen |
| 2003/0069204 A1 | 4/2003 | Inukai et al. |
| 2003/0171330 A1 | 9/2003 | Hotoda et al. |
| 2003/0236225 A1 | 12/2003 | Protopopova et al. |
| 2004/0033986 A1 | 2/2004 | Protopopova et al. |
| 2004/0058964 A1 | 3/2004 | Devadas |
| 2004/0147591 A1 | 7/2004 | Kanie et al. |
| 2005/0014800 A1 | 1/2005 | Matsuoka et al. |
| 2005/0113574 A1 | 5/2005 | Bogatcheva et al. |
| 2008/0081070 A1 | 4/2008 | Wilson et al. |

FOREIGN PATENT DOCUMENTS

| | | |
|---|---|---|
| CA | 2409741 A1 | 10/2002 |
| GB | 729332 | 5/1955 |
| GB | 961317 | 6/1964 |
| GB | 1157143 | 7/1969 |

(Continued)

OTHER PUBLICATIONS

Burman (Am J Med Sci 313:355-363, 1997).*

(Continued)

*Primary Examiner*—Brandon J Fetterolf
*Assistant Examiner*—Craig Ricci
(74) *Attorney, Agent, or Firm*—Johnson & Associates

(57) ABSTRACT

Methods and compositions for treating disease caused by infectious agents, particularly tuberculosis. In particular, methods and compositions comprising novel diamine compositions for the treatment of infectious diseases are provided. In one embodiment, these methods and compositions are used for the treatment of mycobacterial infections, including, but not limited to, tuberculosis.

3 Claims, 62 Drawing Sheets

FOREIGN PATENT DOCUMENTS

| | | |
|---|---|---|
| RU | 2168986 | 6/2001 |
| WO | WO 91/10664 A1 | 7/1991 |
| WO | WO 93/10073 A1 | 5/1993 |
| WO | WO 94/28885 A1 | 12/1994 |
| WO | WO 99/51213 A2 | 10/1999 |
| WO | WO 03/068769 A1 | 8/2003 |

OTHER PUBLICATIONS

Drug Resistance Threatens to Reverse Medical Progress, www.who.int—Press Release, pp. 1-4, Jun. 12, 2000.

PCT/US08/04491—International Search Report, *PCT—International Search Report*, pp. 1-8, Jun. 20, 2008.

PCT Search Report—PCT/US08/86224, *PCT—International Search Report*, pp. 1-5, Jul. 31, 2009.

Davis, Brian—USPTO, Notice of Allowance cited in U.S. Appl. No. 11/173,192, *USPTO Notice of Allowance*, pp. 1-5, Jul. 14, 2008.

Lee, R., Combinatorial Lead Optimization of [1,2]-Diamines Based on Ethambutol as Potential Antituberculosis Preclinical Candidates, *Journal of Combinatorial Chemistry*, vol. 5, pp. 172-187, Jan. 1, 2003.

Lewis, R., The Rise of Antibiotic-Resistant Infections, online.-www.fda.gov, pp. 1-7, Sep. 1, 1995.

Arain, T.M., et al., "Bioluminescence Screening In Vitro (Bio-*Siv*) Assays for High-Volume Antimycobacterial Drug Discovery," Antimicrob. Agents Chemother., 1996, vol. 40, No. 6, pp. 1536-1541.

Barry, C.E., III, et al., "Use of Genomics and Combinatorial Chemistry in the Development of New Antimycobacterial Drugs," Biochem. Pharmacol., 2000, vol. 59, pp. 221-231.

Bass, J.B., Jr., et al., "Treatment of Tuberculosis and Tuberculosis Infection in Adults and Children," Am. J. Respir. Crit. Care Med., 1994, vol. 149, pp. 1359-1374.

Belanger, A.E., et al., "The EmbAB Genes of Mycobacterium Avium Encode An Arabinosyl Transferase Involved in Cell Wall Arabinan Biosynthesis that is the Target for the Antimycobacterial Drug Ethambutol," Proc. Natl. Acad. Sci., 1996, vol. 93, pp. 11919-11924.

Brown, D.S., et al., "Merrifield, Alpha-MethoxyPhenyl (MAMP) Resin; A New Versatile Solid Support for the Synthesis of Secondary Amides," Tetrahedron Lett., 1998, vol. 39, pp. 8533-8536.

Chan-Tack, K.M., "Antituberculosis-Drug Resistance," correspondence in N. Engl. J. Med., 1998, vol. 339, No. 15, p. 1079.

Cole, S.T., et al., "Deciphering the Biology of Mycobacterium Tuberculosis from the Complete Genome Sequence," Nature, 1998, vol. 393, pp. 537-544, [Erratum, Nature, 1998, vol. 396, p. 190].

Cuervo, J.H., et al., "Polyalkylamine Chemical Combinatorial Libraries," in Peptides 1994: Proceedings of the European Peptide Symposium, Maia HSL Ed., Esom: Leiden, 1995, pp. 465-466.

Cynamon, et al., "Activities of Several Novel Oxazolidinones Against *Mycobacterium tuberculosis* in a Murine Model," 1999, vol. 43, No. 5, pp. 1189-1191.

Deng, L., et al., "Recognition of Multiple Effects of Ethambutol on Metabolism of Mycobacterial Cell Envelope," Antimicrob. Agents Chemother., 1995, vol. 39, No. 3, pp. 694-701.

Dye, C., et al., "Global Burden of Tuberculosis: Estimated Incidence, Prevalence, and Mortality by Country," J. Am. Med. Assoc., 1999, vol. 282, No. 7, pp. 677-686.

Farmer, P., et. al., "The Dilemma of MDR-TB in the Global Era," Int. J. Tuberc. Lung Dis., 1998, vol. 2, No. 11, pp. 869-876.

Garigipati, R.S., "Reagents for Combinatorial Organic Synthesis: Preparation and Uses of Rink-Chloride," Tetrahedron Lett., 1997, vol. 38, No. 39, pp. 6807-6810.

Gordon, D.W., et. al., "Reductive Alkylation on a Solid Phase: Synthesis of a Piperazinedione Combinatorial Library," Bioorg. Med. Chem. Lett., 1995, vol. 5, No. 1, pp. 47-50.

Gustafson, G.R., et. al., "Incorporation of Carbohydrates and Peptides into Large Triazine-Based Screening Libraries Using Automated Parallel Synthesis," Tetrahedron, 1998, vol. 54, p. 4051-4065.

Häusler, H., et al., "Ethambutol Analogues as Potential Antimycobacterial Agents," Bioorg. Med. Chem. Lett., 2001, vol. 11, pp. 1679-1681.

Lee, M.H., et. al., "Site-Specific Integration of Mycobacteriophage L5: Integration-Proficient Vectors for *Mycobacterium smegmatis, Mycobacterium tuberculosis*, and bacilli Calmette-Guerin," Proc. Natl. Acad. Sci. USA, 1991, vol. 88, pp. 3111-3115.

Lee, R.E., et. al., "Synthesis of the Mycobacterial Arabinose Donor β-D-Arabinofuranosyl-1-monophosphoryldecaprenol, Development of a Basic Arabinosyl-Transferase Assay, and Identification of Ethambutol as and Arabinosyl Transferase Inhibitor," J. Am. Chem. Soc., 1995, vol. 117, pp. 11829-11832.

Liu, G., et. al., "A General Solid-Phase Syntheses Strategy for the Preparation of 2-Pyrrolidinemethanol Ligands," J. Org. Chem., 1995, vol. 60, pp. 7712-7713.

March, J., "Advanced Organic Chemistry: Reactions, Mechanisms, and Structure," $3^{rd}$ ed., John Wiley and Sons, New York, p. 916.

The Merck Index $12^{th}$ edition (1996). S. Budavari, ed., Merck & Co., Inc., Whitehouse Station, NJ, p. 646 entry No. 3841.

O'Brien, R.J., "Scientific Blueprint for Tuberculosis Drug Development," The Global Alliance for TB Drug Development, Inc., 2001.

Pablos-Mendez, A., et. al., "Global Surveillance for Antituberculosis-Drug Resistance," 1994-1997, N. Engl. J. Med., 1998, vol. 338, No. 23, pp. 1641-1649.

Rink, H., "Solid-Phase Synthesis of Protected Peptide Fragments Using a Trialkoxy-Diphenyl-Methylester Resin," Tetrahedron Lett., 1987, vol. 28, No. 33, pp. 3787-3790.

Shawar, R.M., et al., "Rapid Screening of Natural Products for Antimycobacterial Activity by Using Luciferase-Expressing Strains of *Mycobacterium bovis* BCG and *Mycobacterium intracellular*," Antimicrob. Agents Chemother., 1997, vol. 41, No. 3, pp. 570-574.

Shepherd, R.G., et al., "Structure-Activity Studies Leading to Ethambutol, a New Type of Antituberculous Compound," Ann. N.Y. Acad. Sci., 1966, vol. 135, pp. 686-710.

Silen, J.L., et al., "Screening for Novel Antimicrobials from Encoded Combinatorial Libraries by Using a Two-Dimensional Agar Format," Antimicrob. Agents Chemother., 1998, vol. 42, No. 6, pp. 1447-1453.

Sterling, T.R., Chemical Abstracts 131:281083, abstract of AIDS, vol. 13(14), pp. 1899-1904, 1999.

Telenti, A., et al., "The *Emb* Operon, a Gene Cluster of *Mycobacterium tuberculosis* Involved in Resistance to Ethambutol," Natural Medicine, 1997, vol. 3, No. 5, pp. 567-570.

Zuckermann, R.N., et al., "Efficient Method for the Preparation of Peptoids [Oligo(N-substituted glycines)] by Submonomer Solid-Phase Synthesis," J. Am. Chem. Soc., 1992, vol. 114, pp. 10646-10647.

EPO Search Report as cited in EP 04809706, *European Patent Office—Search Report*, p. 105, Jan. 23, 2009.

Cymerman-Craig, J. et al., Chemical Constitution and Anti-Tuberculous Activity: Part II: Bases Possessing the Diphenyl Structure, *British Journal of Experimental Pathology*, vol. 36, pp. 254-260, Jan. 1, 1955.

Office Action issued in U.S. Appl. No. 11/145,499 on May 3, 2007, *U.S. PTO—Office Action*, pp. 1-4, May 3, 2007.

Office Action cited in U.S. Appl. No. 11/145,499 on Nov. 5, 2008, *U.S. PTO—Office Action*, p. 4, Nov. 5, 2008.

Office Action cited in U.S. Appl. No. 11/145,499 on Dec. 14, 2007, *U.S. PTO—Office Action*, pp. 1-5, Dec. 14, 2007.

Office Action cited in U.S. Appl. No. 11/145,499 on May 1, 2008, *U.S. PTO—Office Action*, pp. 1-4, May 1, 2008.

Forbes et al., Studies on the Mode of Action of Ethambutol, *IIIrd International Congress of Chemotherapy*, vol. 1, pp. 174-177, Jan. 1, 1964.

Hamilton-Miller, J.M.T., Inhibition of *Candida* by Compounds which Inhibit Cholesterol Biosynthesis, *Chemotherapy*, vol. 18, pp. 154-161, Jan. 1, 1973.

Murray et al., Chapter 22 Mycobacterium, *Medical Microbiology*, pp. 219-230, Jan. 1, 1990.

Roark, W. et al., Bioisosterism in Drug Design: Identification of and Structure-Activity Relationships in a Series of Glycine Anilide ACAT Inhibitors, *Bioorganic & Medicinal Chemistry Letters*, vol. 3(1), pp. 29-39, Jan. 1, 1995.

Preparation of Novel Compounds derived from Diphenylmethlyeneethylamine, *Chemical Abstracts*, vol. 107, pp. 17884, 1987.

Danchev et al. Synthesis ,Toxicological and Pharmacological Investigations of 8-Basic Substituted Derivatives of Caffeine, *Dockladi na Bulgarskata na Naukite*, vol. 48(5), pp. 119-122, May 17, 1995.

Khullar et al., Mass Spectrometry of I-Substituted Adamantanes. The Effect of Functional Groups on the Primary Fragmentation Pathways, *Journal of Organic Chemistry*, vol. 38(5), pp. 1042-1044, 1973.

Lavrova et al., Synthesis, Complexing, and Antidote Properties of N"-(2-Adamantyl) Diethylenetriaminetetraacetic Acid, *Pharmaceutical Chemistry Journal*, vol. 22(1), pp. 42-47, 1988.

Meszaros et al., An Adamantane Derivative (N-N'(1-Adamantil)-Ethylene Diamine Dibromide) Induced Automaticity in the Ventricular Myocardium of the Frog, *Acta Physiologica Academiae Scientianum Hungarieae*, vol. 58(1), pp. 79-87, 1981.

Nefzi et al., Parallel Solid Phase Synthesis of Tetrasubstituted Diethylenetriamines Via Selective Amide Alkylation, *Tetrahedron*, vol. 55, pp. 335-344, 1999.

Poindexter et al., Use of 2-Oxazolidinones as Ltent, *Tetrahedron Letters*, vol. 35(40), pp. 7331-7334, 1994.

Thomas et al., Cholesterol Lowering Bile Acid Binding Agents: Novel Lipophilic Polyamines, *J. Med. Chem.*, vol. 35(7), pp. 1233-1245, 1992.

Office Action cited in Australian Patent Application No. 2003233610, *Australian Office Action*, pp. 1-16, Oct. 23, 2009.

Znamensskii et al., Adamantane Derivatives. V. Synthesis and Radioprotective Properties of N-Adamantyl Derivatives of Aminothiols, *Pharmaceutical Chemistry Journal*, vol. 17(10), pp. 716-721, 1983.

\* cited by examiner

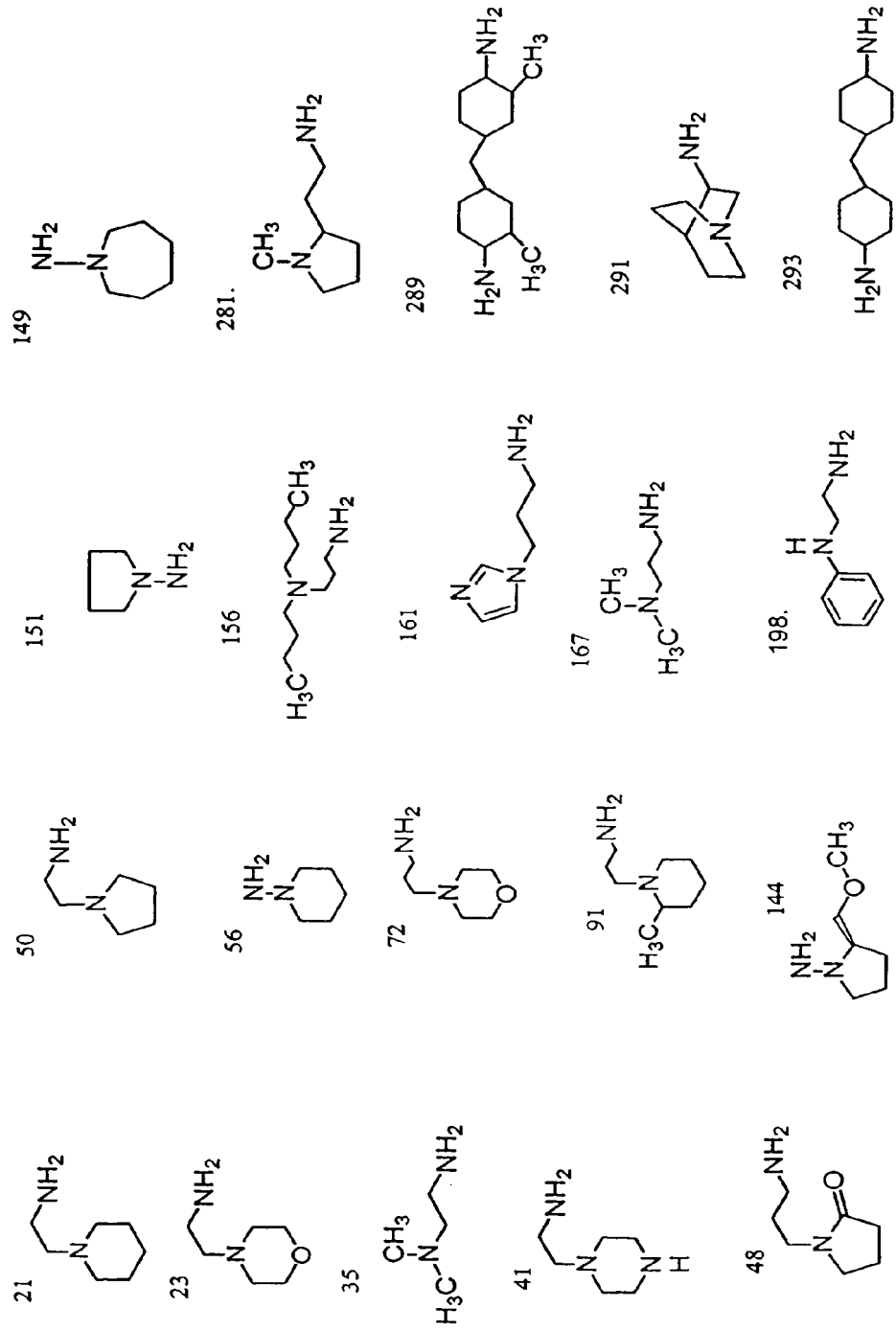
Figure 1. Starting diamines, Group 1

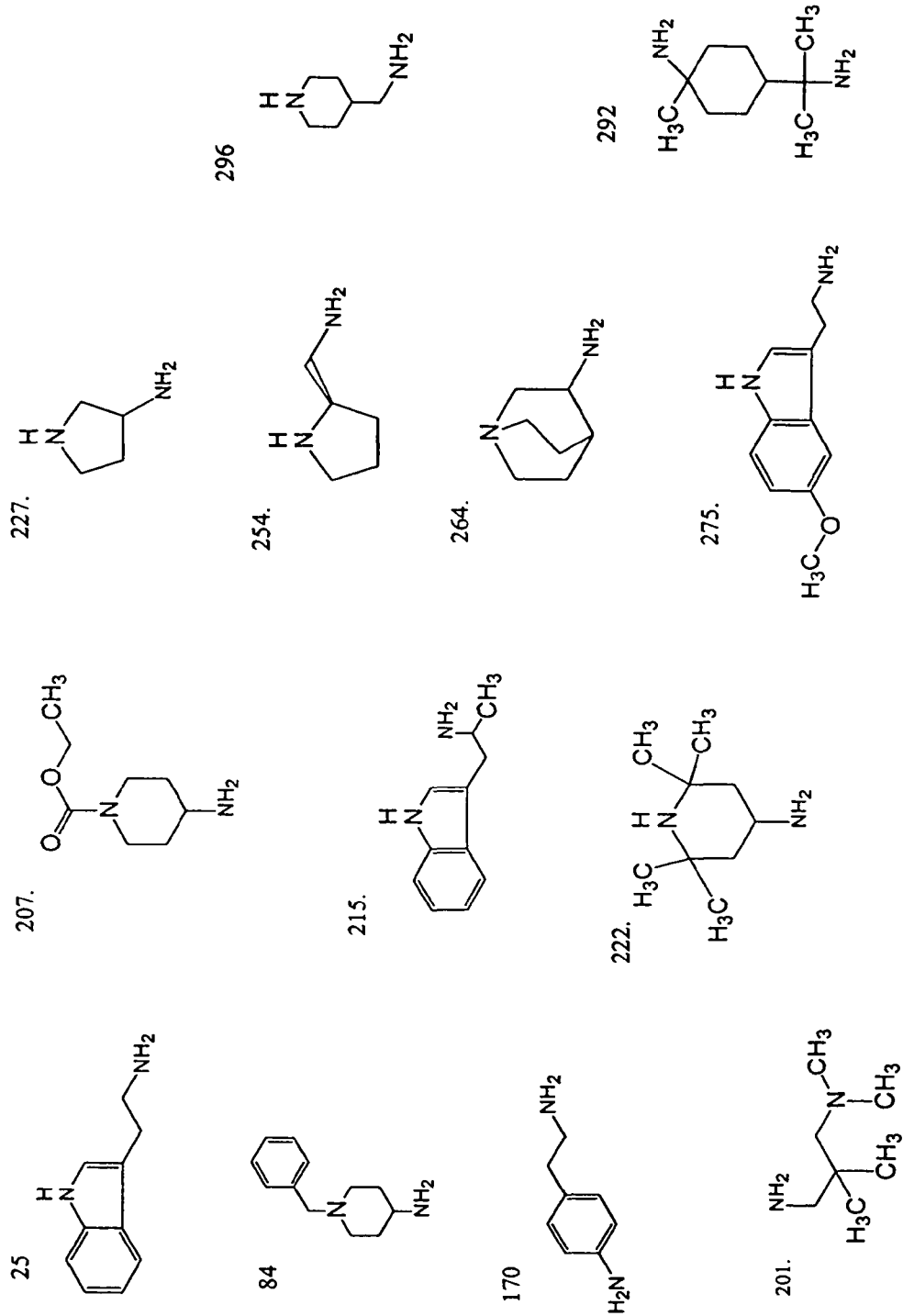
Figure 2. Starting diamines, Group 2

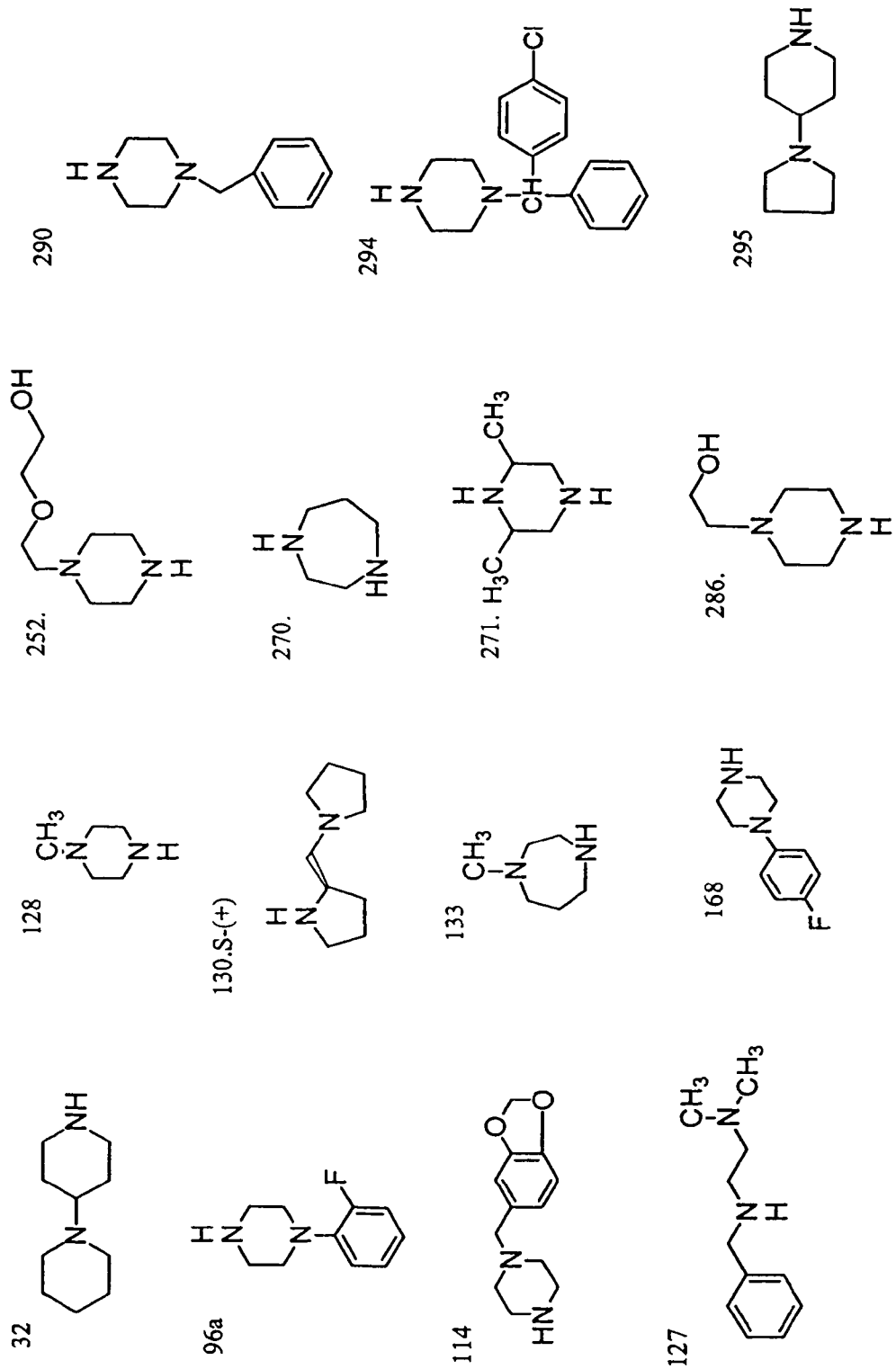
Figure 3. Starting diamines, Group 3

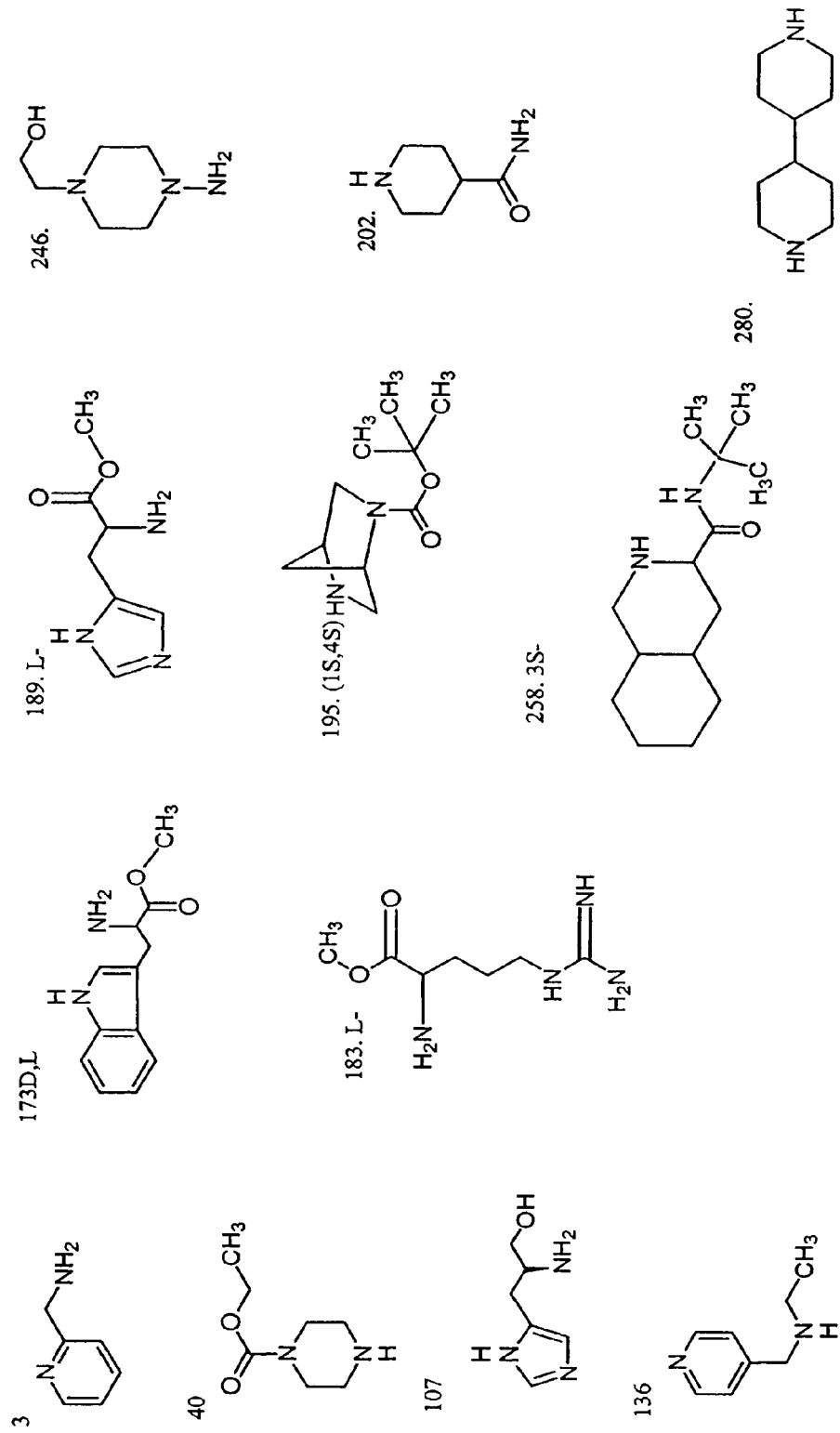
Figure 4. Starting diamines, Group 4

Table 1. Commercially available diamines used for the synthesis

| Group | # | Name |
|---|---|---|
| Group 1 | 21 | 1-(2-Aminoethyl)piperidine |
| | 23 | 4-(2-Aminoethyl)morpholine |
| | 25 | Tryptamine |
| | 41 | 1-(2-Aminoethyl)piperazine |
| | 48 | 1-(3-Aminopropyl)-2-pyrrolidinone (tech) |
| | 50 | 1-(2-Aminoethyl)-pyrrolidine |
| | 56 | 1-Aminopiperidine |
| | 72 | 4-(3-Aminopropyl)morpholine |
| | 91 | 1-(3-Aminopropyl)pipecoline |
| | 144 | (S)-1-Amino-2-(Methoxymethyl)pyrrolidine |
| | 149 | 1-Aminohomopiperidine |
| | 151 | 1-Aminopyrrolidine, hydrochloride |
| | 156 | 3-(Dibutylamino)propylamine |
| | 161 | 1-(3-Aminopropyl)imidazol |
| | 167 | 3-(Dimethylamino)propylamine |
| | 198 | N-Phenylethyldiamine |
| | 281 | 2-(2-Aminoethyl)-1-methylpyrrolidine |
| | 289 | 4,4'-Methylenebis(2-methylcyclohexylamine) |
| | 291 | R-(+)-3-Aminoquinuclidine, dihydrochloride |
| | 293 | 4,4'-Methylenebis(cyclohexylamine) |
| Group 2 | 25 | Tryptamine |
| | 84 | 4-Amino-1-benzylpiperidine |
| | 170a | 2-(4-Aminophenyl)ethylamine |
| | 201 | N,N,2,2-Tetramethyl-1,3-propanediamine |
| | 207 | Ethyl 4-amino-1-piperidinecarboxylate |
| | 215 | alpha-Methyltryptamine |
| | 222 | 4-Amino-2,2,6,6-tetramethylpiperidine |
| | 227 | 3-Aminopyrrolidine, diHCl |
| | 254 | (S)-(+)-2-(Aminomethyl)pyrrolidine |
| | 264 | 3-Aminoquinonuclidine, diHCl |
| | 275 | 5-Methoxytryptamine |
| | 292 | 1,8-Diamino-p-menthane |
| | 296 | 4-(Aminomethyl)piperidine |
| Group 3 | 32 | 4-Piperidinopiperidine |
| | 96a | 1-(2-Fluorophenyl)piperazine |
| | 114 | 1-Piperonylpiperazine |
| | 127 | N'-Benzyl-N,N-dimethylethylenediamine |
| | 128 | 1-Methylpiperazine |
| | 130 | (S)-(+)-(2-Pyrolidinylmethyl)pyrrolidine |
| | 133 | 1-Methylhomopiperazine |
| | 168 | 1-(4-Fluorophenyl)piperazine |
| | 252 | 1-(2-(2-Hydroxyethoxy)ethyl)piperazine |
| | 270 | Homopiperazine |
| | 271 | 2,6-Dimethylpiperazine |
| | 286 | 1-(2-Hydroxyethyl)piperazine |
| | 290 | 1-Benzylpiperazine |
| | 294 | 1-(4-Chlorobenzhydryl)piperazine |
| | 295 | 4-(1-Pyrrolidinyl)piperidine |

Figure 5A

| | | |
|---|---|---|
| Group 4 | 3 | 2-(Aminomethyl)pyridine |
| | 40 | Ethyl 1-piperazine carboxylate |
| | 107 | Histidinol |
| | 136 | 4-(Ethylaminomethyl)pyridine |
| | 173 | d,l-Tryptophan methyl ester, HCl |
| | 183 | l-Arginine methyl ester, HCl |
| | 189 | l-Histidine methyl ester, HCl |
| | 195 | tert-Butyl (1S,4S)-(-)-2,5-diazabicyclo[2.2.1]heptane-2-carboxylate |
| | 202 | Isonipecotamide |
| | 246 | 1-Amino-4-(2-hydroxyethyl)piperazine |
| | 258 | (3S(3a,4Ab),8A b)-N-t-butyl-D-ecahydro-3-isoquinolinecarboxamide |
| | 280 | 4,4'-Bipiperidine, HCl |

Figure 5B

TABLE 2. MASTERPLATE of CARBONYL COMPOUNDS.

| Position on Plate | Reagent # | | F.W. |
|---|---|---|---|
| a1-a12 | | Row "a" is empty | |

| Position on Plate | Reagent # | Ketones | F.W. |
|---|---|---|---|
| | | Name | |
| b1 | 97 | 3-Acetyl-1-propanol | 102 |
| b2 | 98 | 2-Adamantanone | 150.22 |
| b3 | 99 | 1-Adamantyl methyl ketone | 178.28 |
| b4 | 100 | Cyclobutanone | 70.09 |
| b5 | 101 | 1,4-Cyclohexanedione monoethylene ketal | 156.18 |
| b6 | 102 | 2-Decalone | 152.24 |
| b7 | 103 | (4-Fluorophenyl)acetone | 152.17 |
| b8 | 104 | Geranylacetone | 194.32 |
| b9 | 105 | 5-Hydroxy-2-adamantanone | 166.22 |
| b10 | 106 | 3-Hydroxy-2-butanone | 88.11 |
| b11 | 107 | 4-(4-Hydroxyphenyl)-2-butanone | 164.20 |
| b12 | 108 | 4-Methylcyclohexanone | 112.17 |

| Position on Plate | Reagent # | Aldehydes + Ketones | F.W. |
|---|---|---|---|
| | | Name | |
| c1 | 25 | 1,4-Benzodioxan-6-carboxaldehyde | 164.16 |
| c2 | 26 | 4-Benzyloxybenzaldehyde | 212.25 |
| c3 | 27 | Benzyloxyacetaldehyde | 150.18 |
| c4 | 28 | 2-Chlorobenzaldehyde | 140.57 |
| c5 | 29 | 4-Chlorobenzaldehyde | 140.57 |
| c6 | 109 | 1-Methyl-4-piperidone | 113.16 |
| c7 | 31 | 2-Chloro-4-fluorobenzaldehyde | 158.56 |
| c8 | 32 | 3-(4-Chlorophenoxy)-benzaldehyde | 232.67 |
| c9 | 33 | 5-(4-Chlorophenyl)furfural | 206.63 |
| c10 | 34 | trans-Cinnamaldehyde | 132.16 |
| c11 | 35 | (S)-(-)-Citronellal | 154.25 |
| c12 | 36 | Cyclohexanecarboxaldehyde | 112.17 |

| | | | |
|---|---|---|---|
| d1 | 37 | Cyclopropanecarboxaldehyde | 70.09 |
| d2 | 38 | 2,4-Dichlorobenzaldehyde | 175.01 |
| d3 | 39 | 2,4-Difluorobenzaldehyde | 142.11 |
| d4 | 40 | 2,5-Difluorobenzaldehyde | 142.11 |
| d5 | 41 | 2,3-Dihydroxybenzaldehyde | 138.12 |
| d6 | 42 | 2,4-Dihydroxybenzaldehyde | 138.12 |
| d7 | 43 | 2,5-Dimethoxy-3-tetrahydrofurancarboxaldehyde | 160.17 |
| d8 | 44 | 4-(Dimethylamino)benzaldehyde | 149.19 |
| d9 | 45 | 2,5-Dimethylbenzaldehyde | 134.18 |
| d10 | 110 | Nerylacetone (Geranylacetone ~ 35% Nerylacetone) | 194.32 |
| d11 | 47 | Diphenylacetaldehyde | 196.25 |
| d12 | 48 | 2-Ethoxybenzaldehyde | 150.18 |

Figure 6A

TABLE 2. MASTERPLATE of CARBONYL COMPOUNDS.

| | | | |
|---|---|---|---|
| e1 | 49 | 4-Ethoxybenzaldehyde | 150.18 |
| e2 | 50 | 3-Ethoxysalicylaldehyde | 166.18 |
| e3 | 111 | (1R)-(+)-Nopinone | 138.21 |
| e4 | 52 | 3-Fluoro-p-anisaldehyde | 154.14 |
| e5 | 53 | 2-Fluorobenzaldehyde | 124.11 |
| e6 | 54 | 4-Fluorobenzaldehyde | 124.11 |
| e7 | 55 | 3-Fluorosalicylaldehyde | 140.11 |
| e8 | 56 | 2-Furaldehyde | 96.09 |
| e9 | 112 | Norcamphor | 110.16 |
| e10 | 113 | 2-Phenylcycloheptanone | 188.27 |
| e11 | 59 | Hydrocinnamaldehyde | 134.18 |
| e12 | 60 | 3-Hydroxybenzaldehyde | 122.12 |
| f1 | 61 | 4-Hydroxybenzaldehyde | 122.12 |
| f2 | 62 | 2-Hydroxy-4-methoxybenzaldehyde | 152.15 |
| f3 | 63 | 5-(Hydroxymethyl)furfural | 126.11 |
| f4 | 64 | 4-Hydroxy-3-nitrobenzaldehyde | 167.12 |
| f5 | 65 | Cyclooctanone | 126 |
| f6 | 66 | Indole-3-carboxaldehyde | 145.16 |
| f7 | 67 | Isobutyraldehyde | 72.11 |
| f8 | 68 | 4-Isopropylbenzaldehyde | 148.21 |
| f9 | 69 | Isovaleraldehyde | 86.13 |
| f10 | 70 | 2-Methoxycinnamaldehyde | 162.19 |
| f11 | 71 | 2-Methoxy-1-naphthaldehyde | 186.21 |
| f12 | 114 | 3-Quinuclidinone hydrochloride | 161.63 |
| g1 | 73 | 2,3-(Methylenedioxy)benzaldehyde | 150.13 |
| g2 | 74 | 4-Methyl-5-imidazolecarboxaldehyde | 110.12 |
| g3 | 75 | 1-Methylindole-3-carboxaldehyde | 159.19 |
| g4 | 76 | 1-Methyl-2-pyrrolecarboxaldehyde | 109.13 |
| g5 | 77 | 4-(Methylthio)benzaldehyde | 152.22 |
| g6 | 78 | 3-Methyl-2-thiophenecarboxaldehyde | 126.18 |
| g7 | 79 | (1R)-(-)-Myrtenal | 150.22 |
| g8 | 115 | Tetrahydro-4H-pyran-4-one | 100.12 |
| g9 | 81 | 2-Naphthaldehyde | 156.18 |
| g10 | 82 | 2-Nitrobenzaldehyde | 151.12 |
| g11 | 83 | 5-Norbornene-2-carboxaldehyde | 122.17 |
| g12 | 84 | (S)-(-)-Perillaldehyde | 150.22 |
| h1 | 116 | β-Tetralone | 146.19 |
| h2 | 86 | Trimethylacetaldehyde | 86.13 |
| h3 | 87 | 2-Pyridinecarboxaldehyde | 107.11 |
| h4 | 88 | 3-Pyridinecarboxaldehyde | 107.11 |
| h5 | 89 | 4-Pyridinecarboxaldehyde | 107.11 |
| h6 | 90 | Pyrrole-2-carboxaldehyde | 95.10 |
| h7 | 91 | 4-Quinolinecarboxaldehyde | 157.17 |

Figure 6B

TABLE 2. MASTERPLATE of CARBONYL COMPOUNDS.

| | | | |
|---|---|---|---|
| h8 | 92 | 1,2,3,6-Tetrahydrobenzaldehyde | 110.16 |
| h9 | 93 | 2-Thiophenecarboxaldehyde | 112.15 |
| h10 | 94 | α,α,α-Trifluoro-p-tolualdehyde | 174.12 |
| h11 | 95 | 2,3,4-Trimethoxybenzaldehyde | 196.20 |
| h12 | 117 | p-Anisaldehyde | 136.15 |

Figure 6C

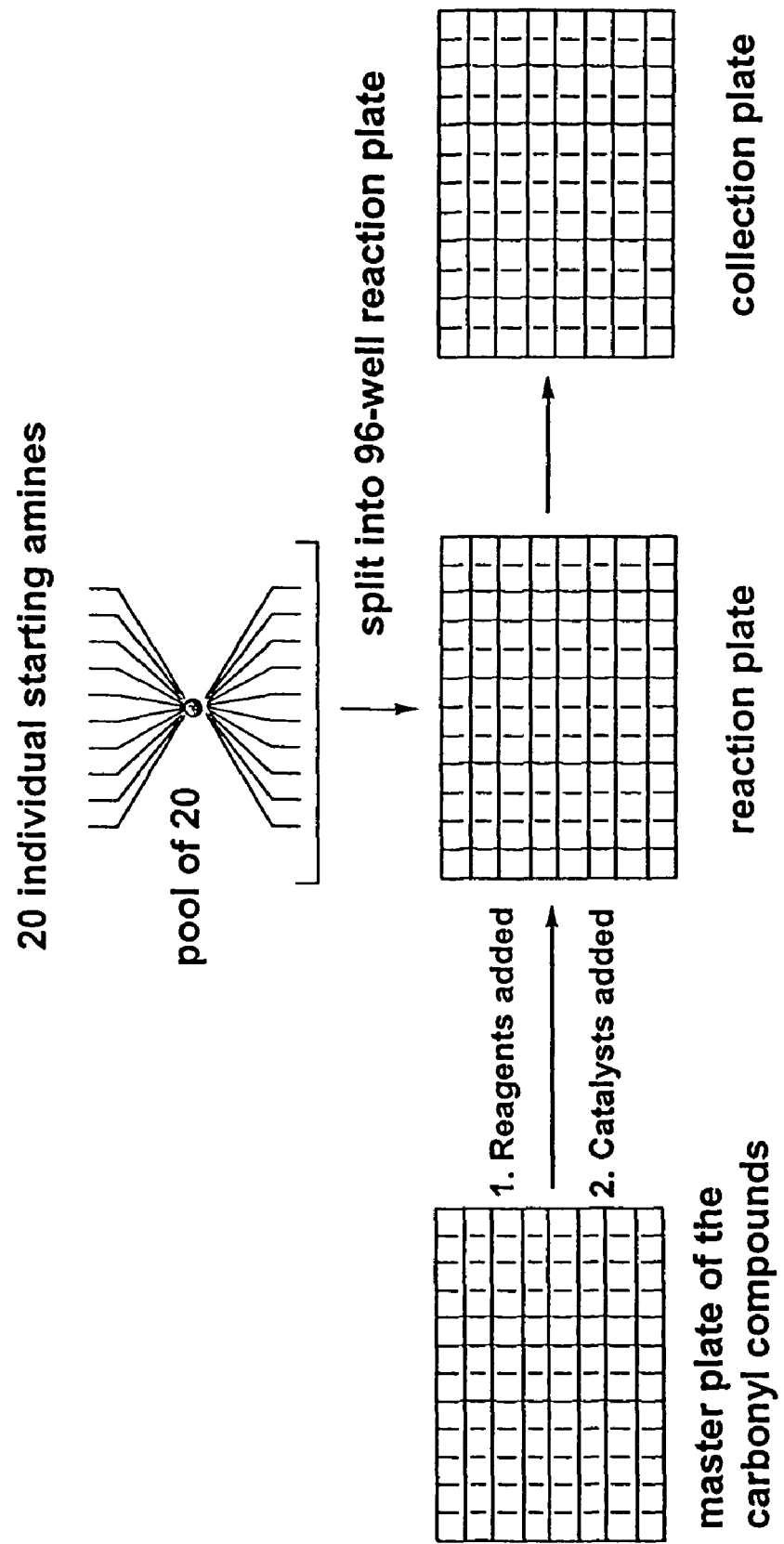
Figure 7. Synthesis in the 96-well format

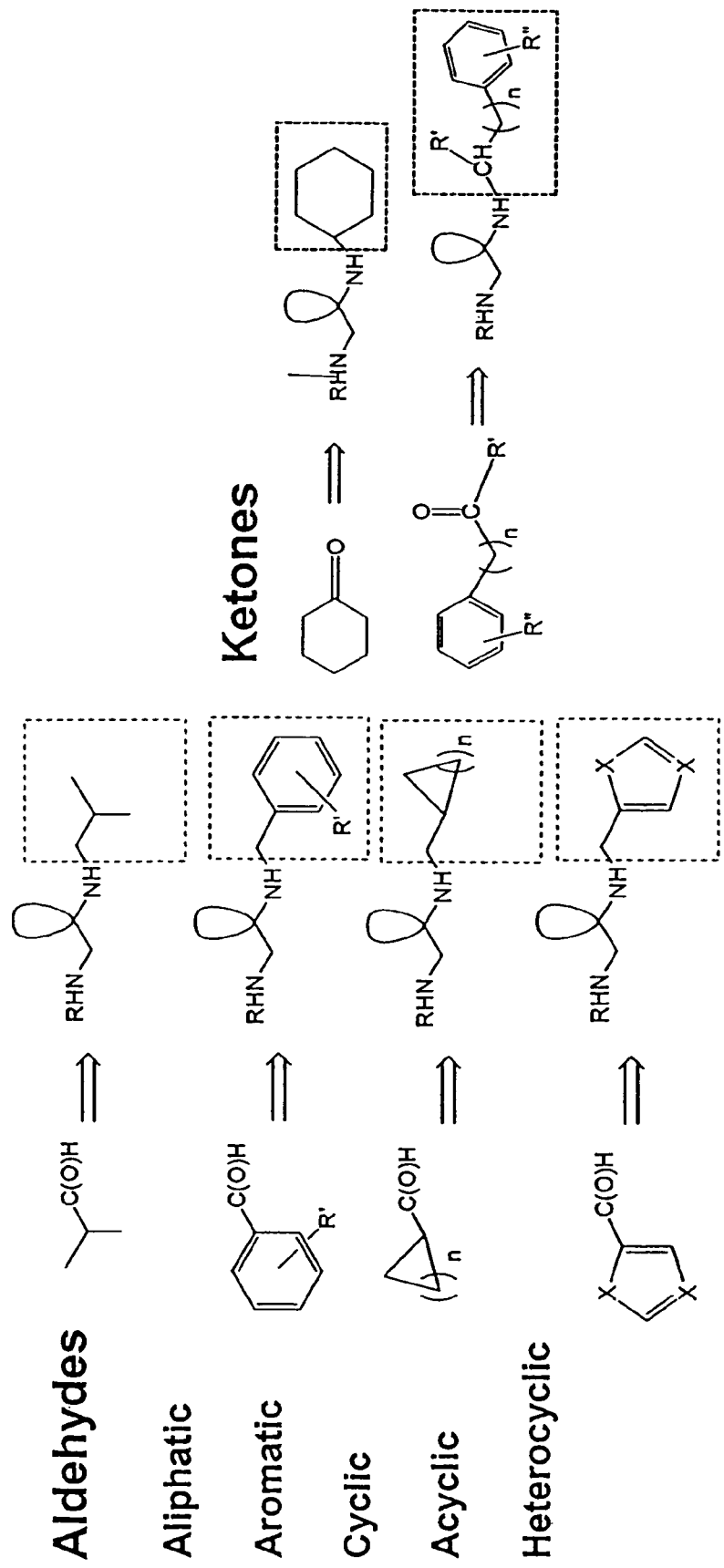
Figure 8. Carbonyl compounds used in synthesis

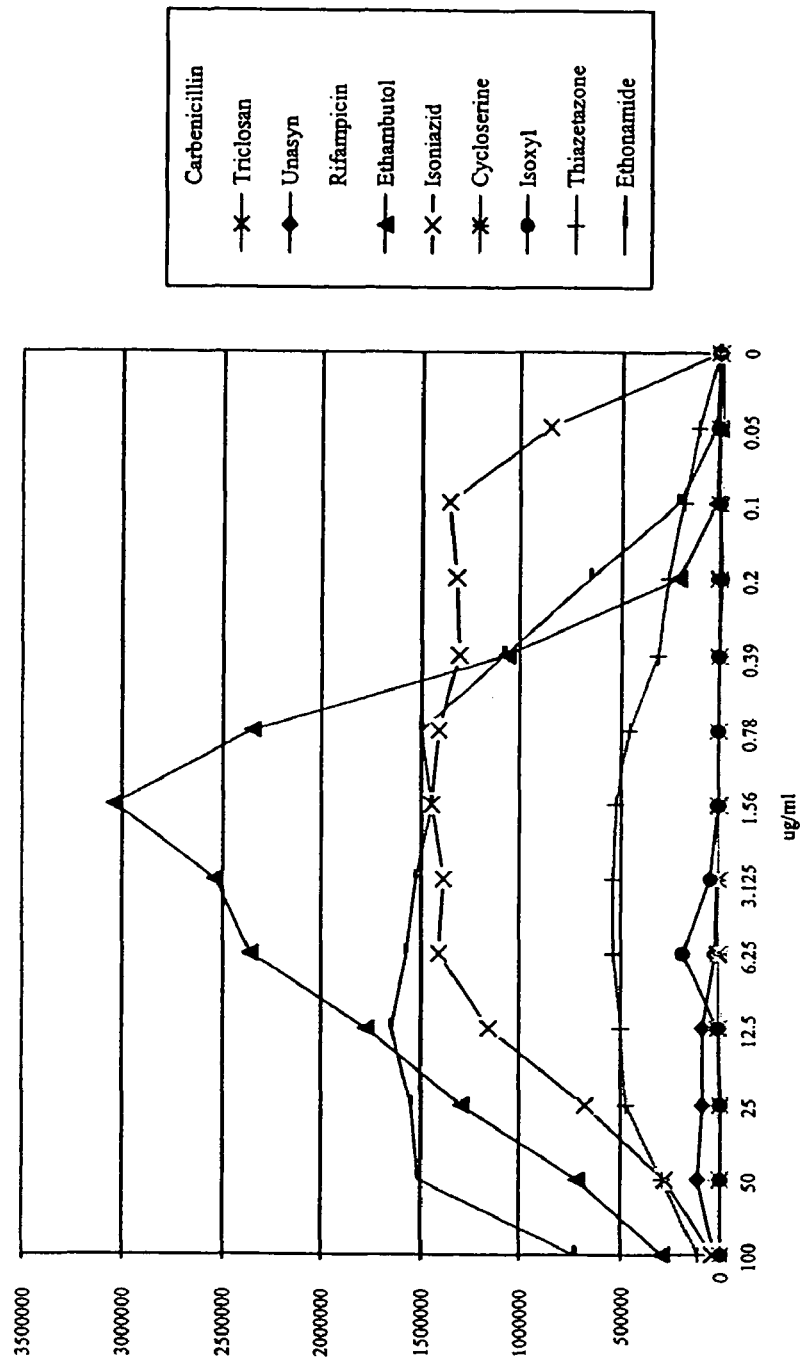
Figure 9. *M.tuberculosis* Rv0341p_Lucs Drug Response

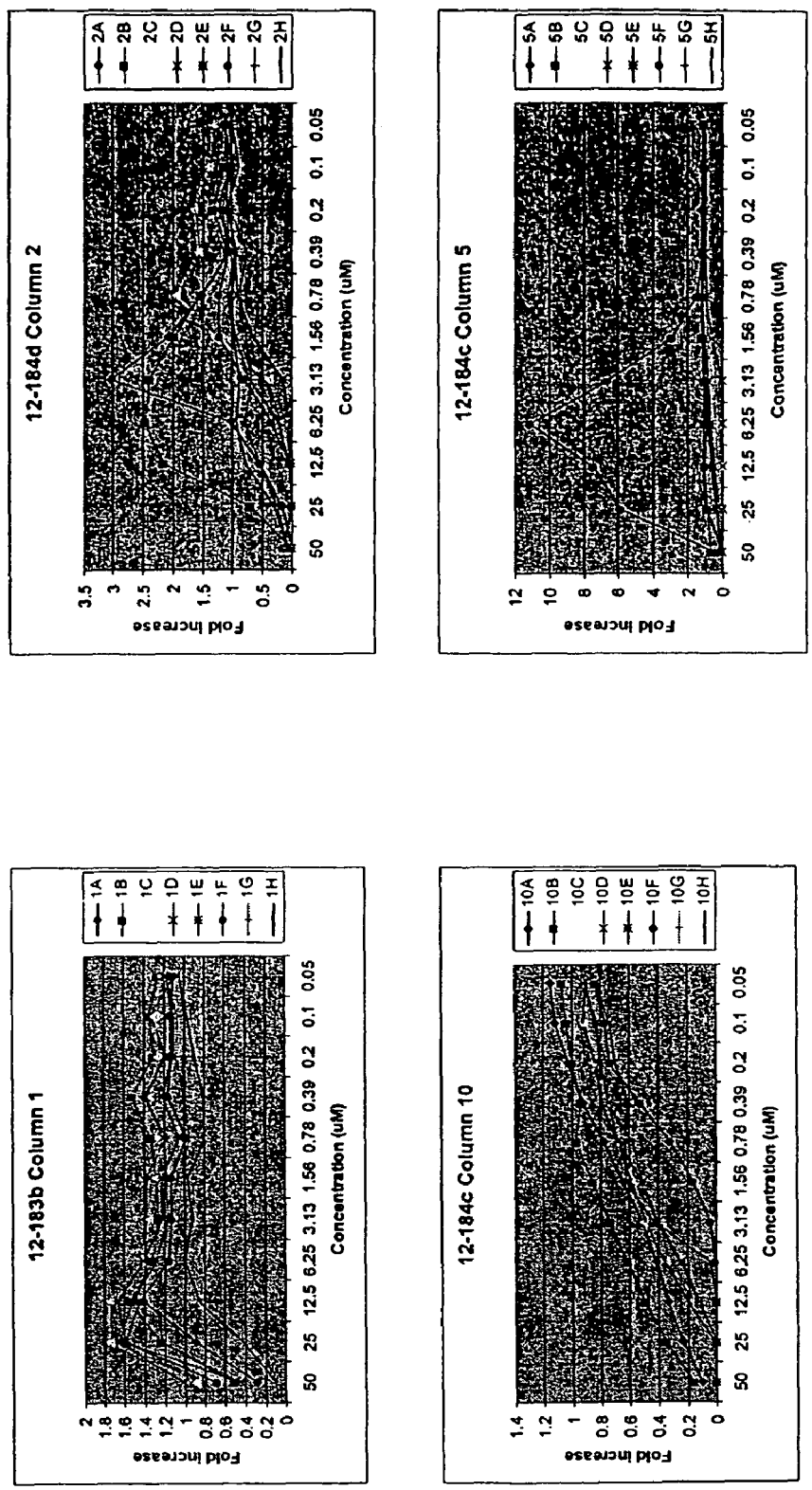
Figure 10. Luc data for representative wells

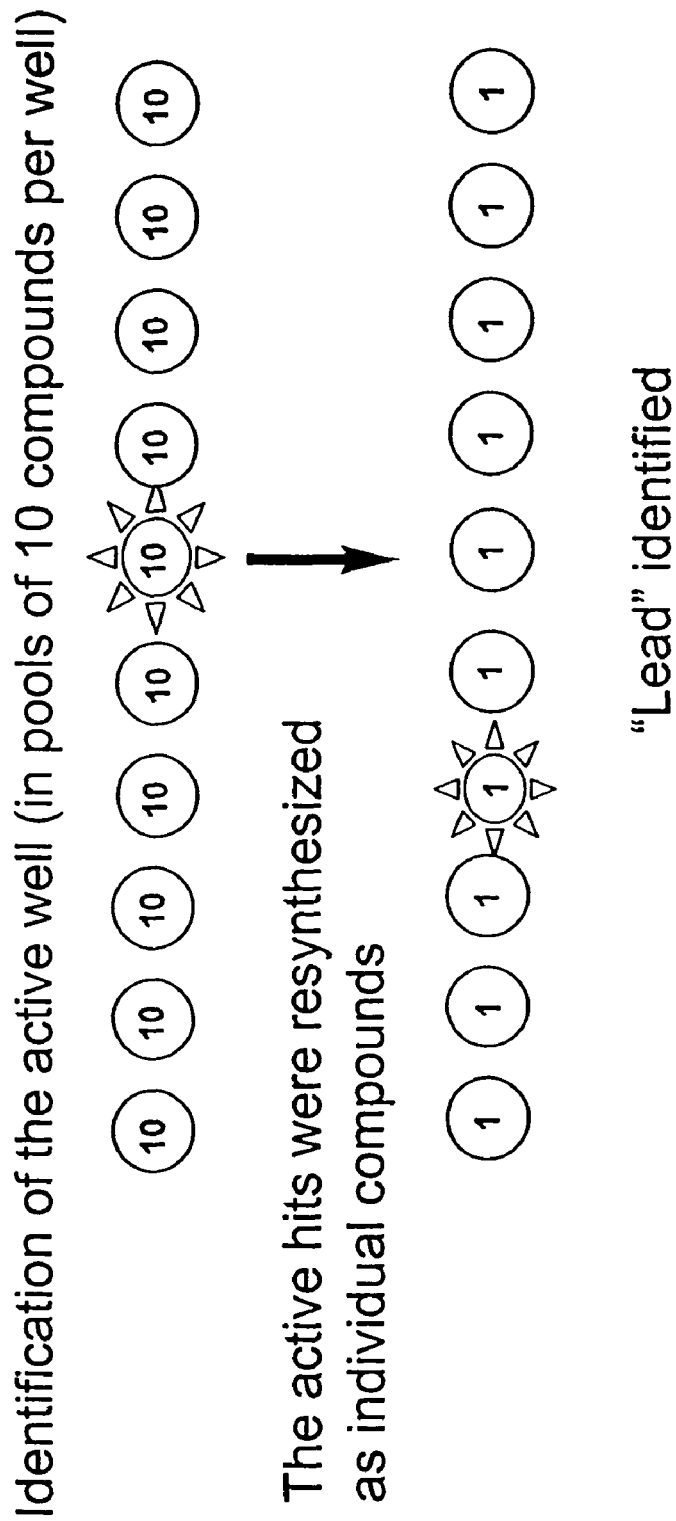
Figure 11. Deconvolution procedure (example: procedure for the compounds made in the pools of 10)

Figure 12. Deconvolution template

| | | | | | | | | | | |
|---|---|---|---|---|---|---|---|---|---|---|
| A1 | A2 | A3 | A4 | A5 | A6 | A7 | A8 | A9 | A10 | Selected carb/comp, added to A1-A10 |
| B1 | B2 | B3 | B4 | B5 | B6 | B7 | B8 | B9 | B10 | Selected carb/comp, added B1-B10 |
| C1 | C2 | C3 | C4 | C5 | C6 | C7 | C8 | C9 | C10 | Selected carb/comp, added C1-C10 |
| D1 | D2 | D3 | D4 | D5 | D6 | D7 | D8 | D9 | D10 | Selected carb/comp, added D1-D10 |
| E1 | E2 | E3 | E4 | E5 | E6 | E7 | E8 | E9 | E10 | Selected carb/comp, added E1-E10 |
| F1 | F2 | F3 | F4 | F5 | F6 | F7 | F8 | F9 | F10 | Selected carb/comp, added F1-F10 |
| G1 | G2 | G3 | G4 | G5 | G6 | G7 | G8 | G9 | G10 | Selected carb/comp, added G1-G10 |
| H1 | H2 | H3 | H4 | H5 | H6 | H7 | H8 | H9 | H10 | Selected carb/comp, added H1-H10 |
| | | | | | | | | | | "X" selected carbonyl compounds to be added |
| Amine #1 | Amine #2 | Amine #3 | Amine #4 | Amine #5 | Amine #6 | Amine #7 | Amine #8 | Amine #9 | Amine #10 | Individual starting amines ##1 through 10, commercially availbale |

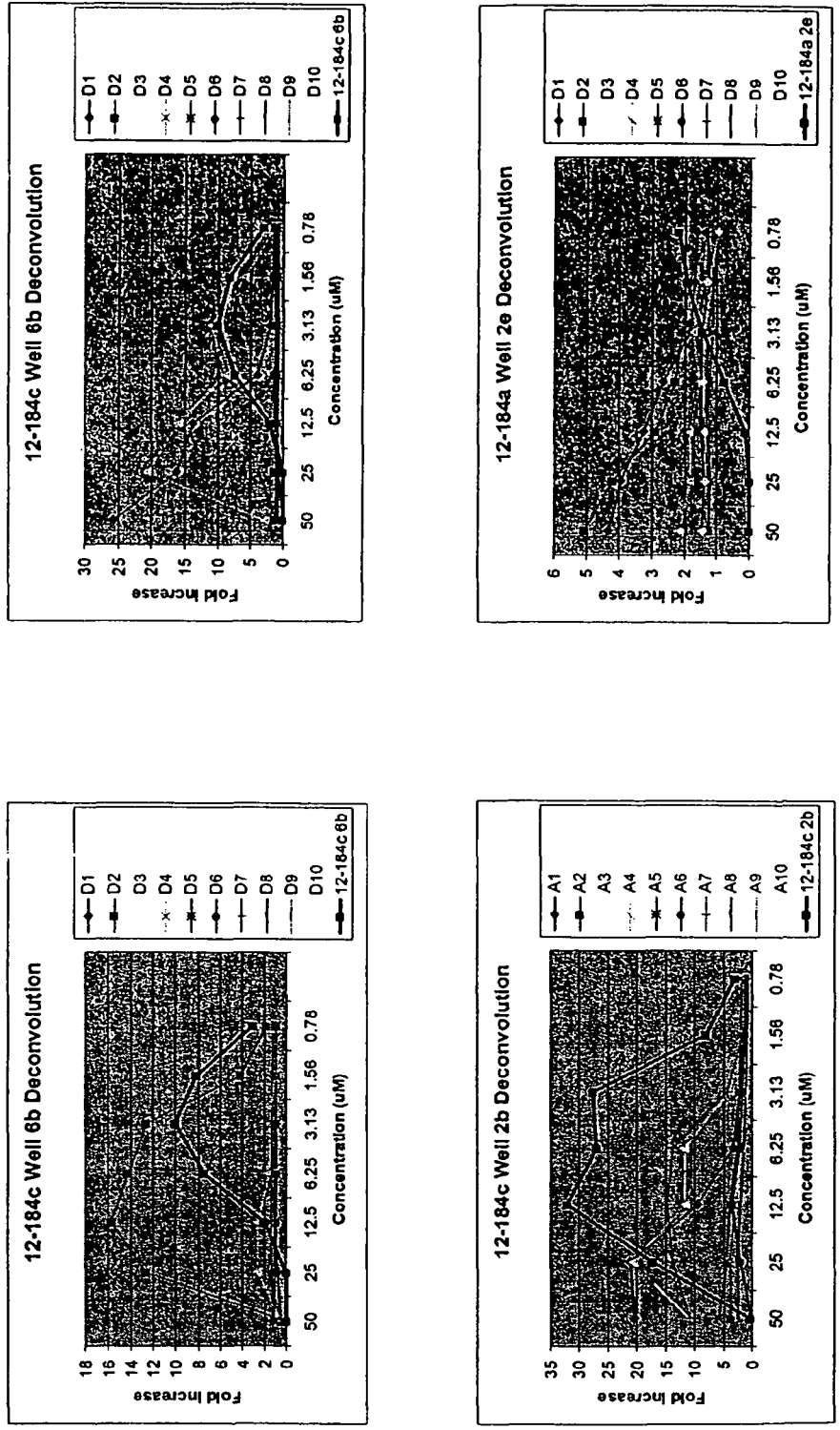
Figure 13. Representative Luc data for deconvoluted samples

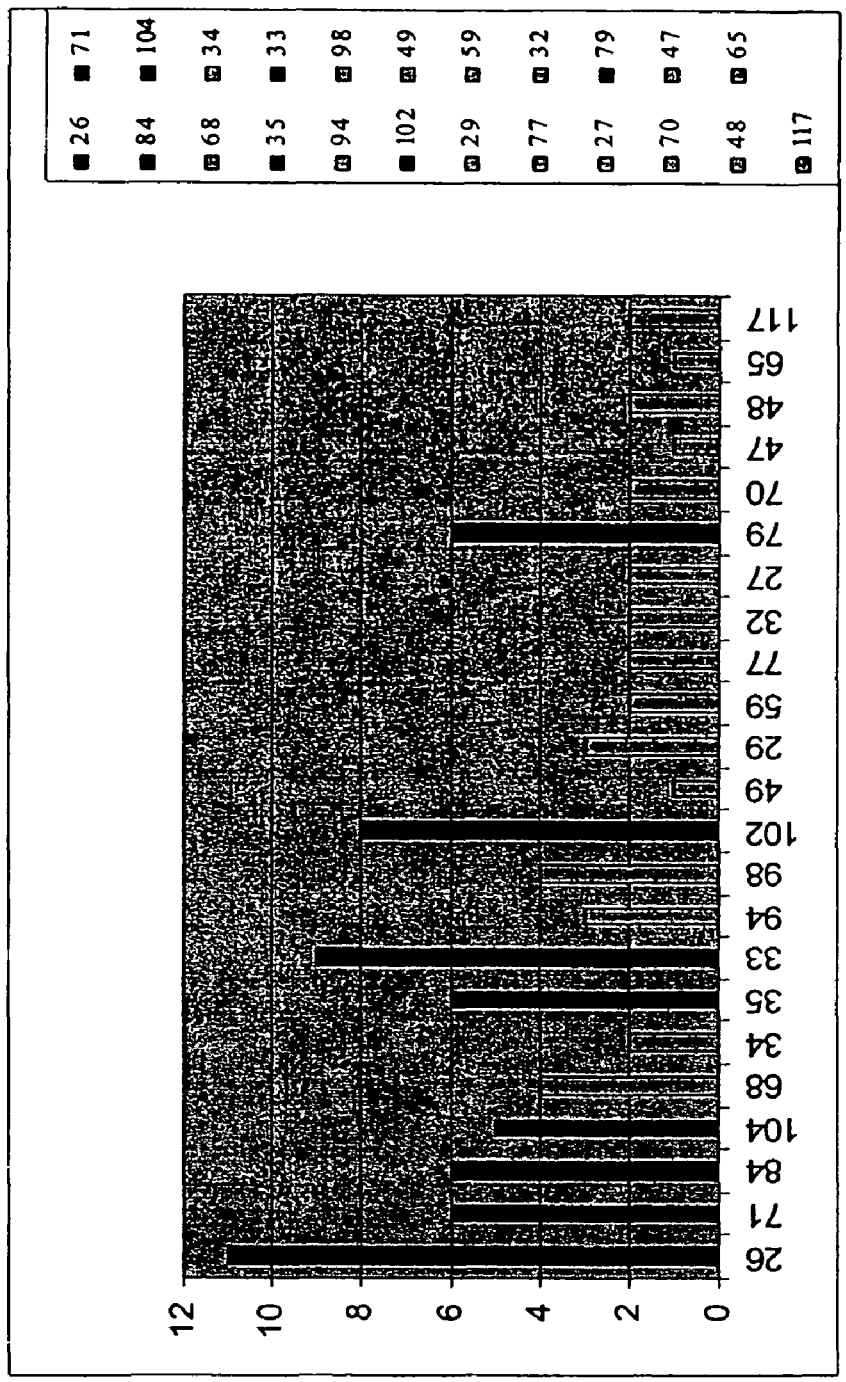
Figure 14. Occurrence of the synthons derived from starting carbonyl compounds in the hits

| # | Structure | MIC | MIC exper. | IC50 (uM) | SI | Lux | LogP | TPSA | Frag. #2 | Original plate # |
|---|---|---|---|---|---|---|---|---|---|---|
| 700 | 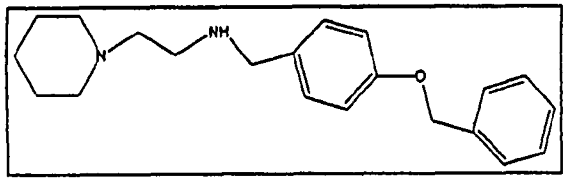 | 12.5 | | | | 1.5 | 4.24+/-0.39 | | 26 | 12-184A-1 |
| 701 | 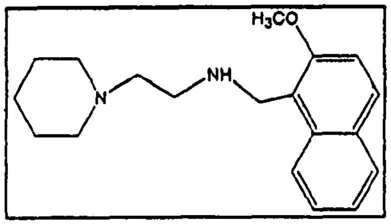 | 6.25 | | | | 1.48 | | | 71 | 12-184A-1 |
| 702 | 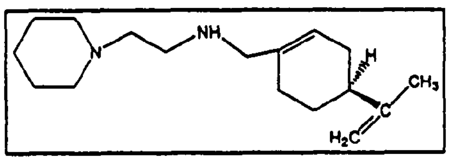 | 12.5 | | | | 1 | | | 84 | 12-184A-1 |
| 703 | 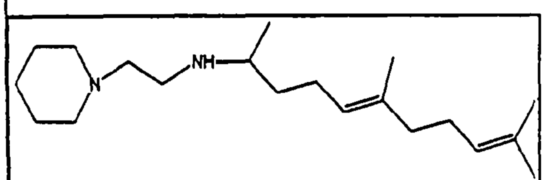 | 12.5 | | | | 1.7 | | | 104 | 12-184A-1 |

Figure 15A

| | | | | | | |
|---|---|---|---|---|---|---|
| 704 | [structure] | 12.5 | | | 1 | 68 | 12-184A-1 |
| 705 | [structure] | 12.5 | | | 1.52 | 26 | 12-184A-1 |
| 706 | [structure] | 12.5 | | | 1.12 | 71 | 12-184A-1 |
| 707 | [structure] | 12.5 | | | 1 | 26 | 12-184A-1 |
| 708 | [structure] | 12.5 | | | 1.12 | 71 | 12-184A-1 |

Figure 15B

| | | | | | |
|---|---|---|---|---|---|
| 709 | 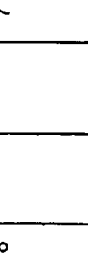 | 12.5 | | | 1.18 | | | 71 | 12-184A-1 |
| 710 | 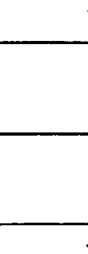 | 12.5 | | | 1.04 | | | 68 | 12-184A-1 |
| 711 | 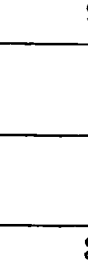 | 6.25 | | | 13.86 | | | 104 | 12-184A-1 |
| 712 | 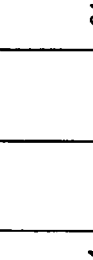 | 12.5 | | | 3.04 | | | 94 | 12-184A-1 |
| 713 |  | 12.5 | | | 1.03 | | | 104 | 12-184A-2 |
Figure 15C

| | | | | | | | | |
|---|---|---|---|---|---|---|---|---|
| 714 | [structure] | 3.13 | | | 0.95 | 7.23+/-0.27 | 26 | 12-184A-2 |
| 715 | [structure] | 3.13 | | | 1 | 6.28+/-0.27 | 71 | 12-184A-2 |
| 716 | [structure] | 3.13 | | | 1 | | 84 | 12-184A-2 |
| 717 | [structure] | 12.5 | | | 0.8 | | 102 | 12-184A-2 |
| 718 | [structure] | 12.5 | | | 1.1 | | 104 | 12-184A-2 |

Figure 15D

| | | | | | | |
|---|---|---|---|---|---|---|
| 719 | 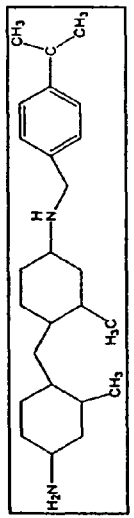 | 3.13 | | | 0.76 | | | 68 | 12-184A-2 |
| 720 | 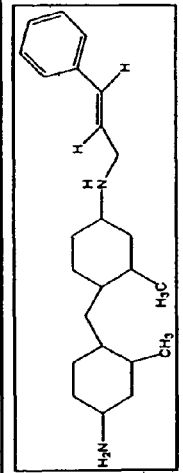 | 6.25 | | | 1 | | | 34 | 12-184A-2 |
| 721 | 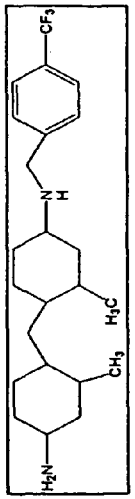 | 12.5 | | | 0.8 | | | 94 | 12-184A-2 |
| 722 | 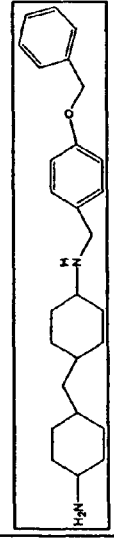 | 1.56 | | | 0.7 | 6.24+/-0.27 dbl.sym. 10.0+/-0.33 | | 26 | 12-184A-2 |
| 723 | 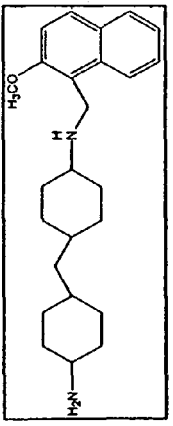 | 3.13 | | | 1 | 5.82+/-0.26 | | 71 | 12-184A-2 |
Figure 15E

| | | | | | |
|---|---|---|---|---|---|
| 724 | 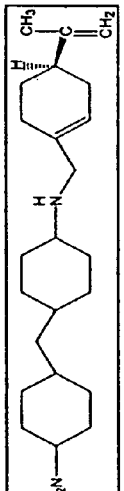 | 3.13 | | | 0.6 | | | 84 | 12-184A-2 |
| 725 | 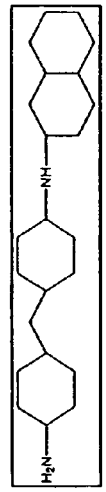 | 12.5 | | | 0.64 | | | 102 | 12-184A-2 |
| 726 | 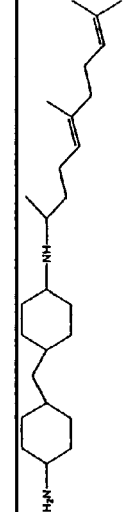 | 12.5 | | | 0.9 | | | 104 | 12-184A-2 |
| 727 | 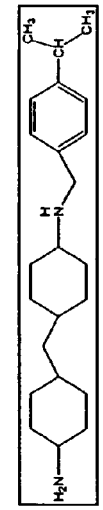 | 3.13 | | | 0.58 | | | 68 | 12-184A-2 |
| 728 | 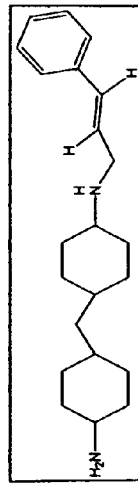 | 6.25 | | | 0.7 | | | 34 | 12-184A-2 |
Figure 15F

| | | | | | | | | | |
|---|---|---|---|---|---|---|---|---|---|
| 729 | ![structure] | 6.25 | | | | 0.5 | | | 94 | 12-184A-2 |
| 730 | ![structure] | 12.5 | | | | 1.98 | | | 35 | 12-184A-3 |
| 731 | ![structure] | 12.5 | | | | 1.98 | | | 35 | 12-184A-3 |
| 732 | ![structure] | 25 | | | | 12 | | | 98 | 12-184A-4 |
| 733 | ![structure] | 12.5 | | | | 1.7 | | | 35 | 12-184A-4 |

Figure 15G

| | | | | | | | |
|---|---|---|---|---|---|---|---|
| 734 | [structure] | 12.5 | | | 2.04 | | 35 | 12-184A-4 |
| 735 | [structure] | 6.25 | | | 1 | | 32 | 12-184A-4 |
| 736 | [structure] | 6.25 | | | 0.9 | | 27 | 12-184A-4 |
| 737 | [structure] | 6.25 | | | 3.29 | | 79 | 12-184A-4 |
| 738 | [structure] | 6.25 | | | 1.5 | | 70 | 12-184A-4 |

Figure 15H

| | | | | | | | | |
|---|---|---|---|---|---|---|---|---|
| 739 | 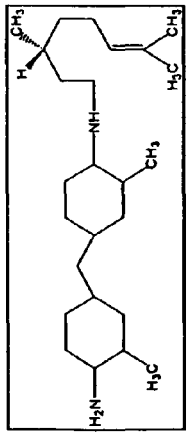 | 3.13 | | | 1.44 | | | 35 | 12-184A-4 |
| 740 | 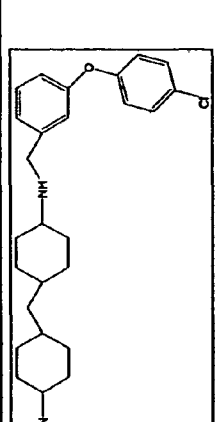 | 3.13 | | | 0.33 | | | 32 | 12-184A-4 |
| 741 | 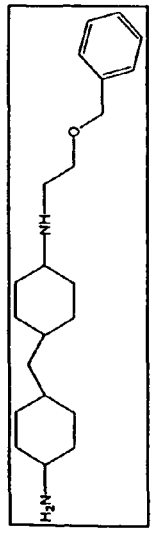 | 12.5 | | | 0.7 | | | 27 | 12-184A-4 |
| 742 | 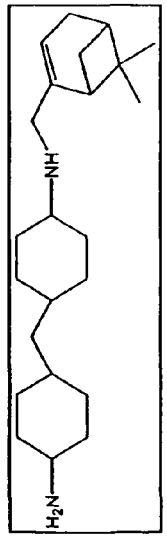 | 12.5 | | | 1.5 | | | 79 | 12-184A-4 |
| 743 | 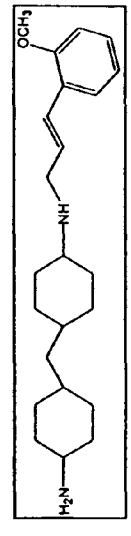 | 6.25 | | | 1.1 | | | 70 | 12-184A-4 |
Figure 15I

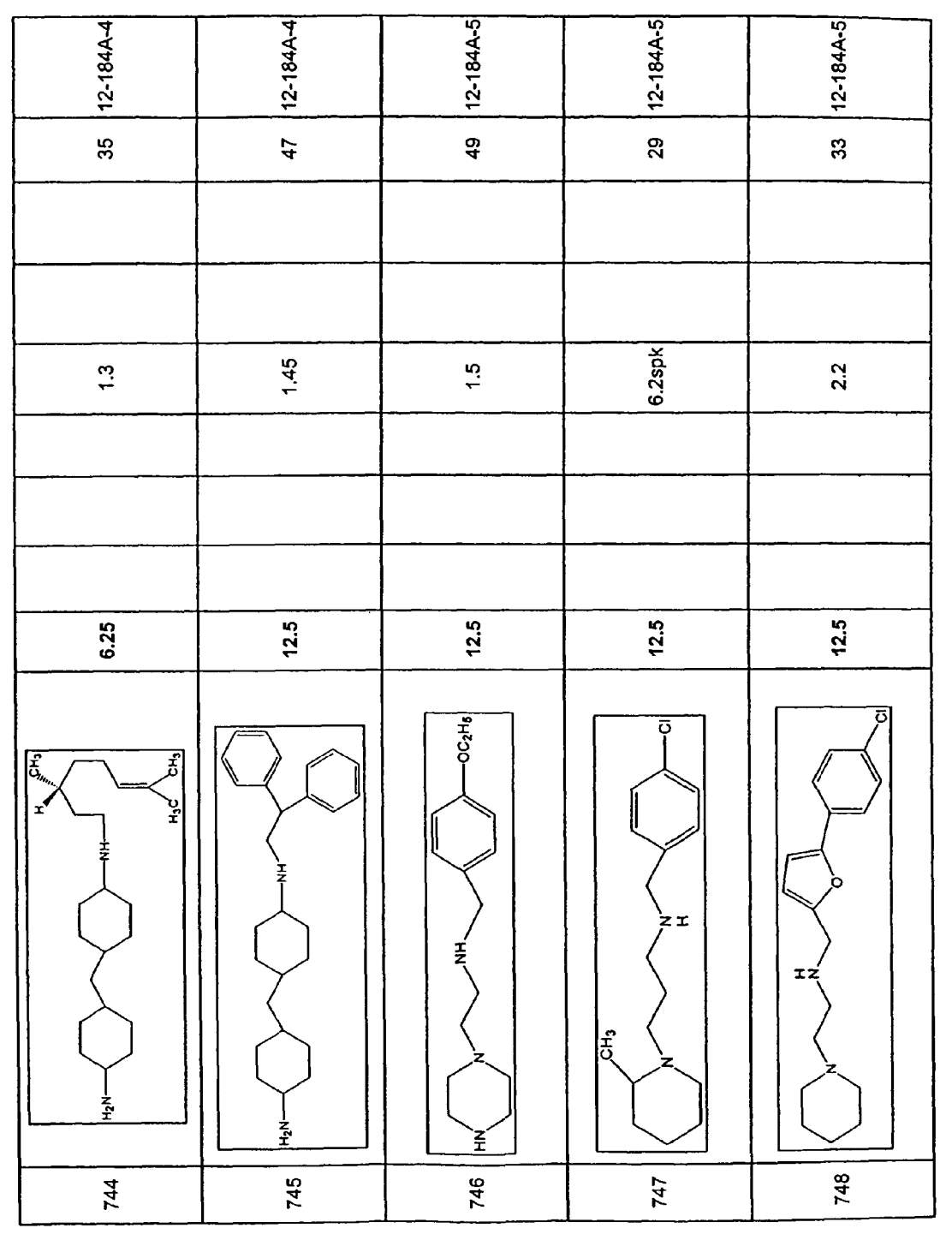

| | | | | | | | | | |
|---|---|---|---|---|---|---|---|---|---|
| 744 | [structure] | 6.25 | | | | 1.3 | | | 35 | 12-184A-4 |
| 745 | [structure] | 12.5 | | | | 1.45 | | | 47 | 12-184A-4 |
| 746 | [structure] | 12.5 | | | | 1.5 | | | 49 | 12-184A-5 |
| 747 | [structure] | 12.5 | | | | 6.2spk | | | 29 | 12-184A-5 |
| 748 | [structure] | 12.5 | | | | 2.2 | | | 33 | 12-184A-5 |

Figure 15J

| | | | | | | | | | |
|---|---|---|---|---|---|---|---|---|---|
| 749 | [structure] | 12.5 | | | | 3.8spk | | 33 | 12-184A-5 |
| 750 | [structure] | 12.5 | | | | 2.2 | | 33 | 12-184A-5 |
| 751 | [structure] | 12.5 | | | | 0.85 | | 33 | 12-184A-5 |
| 752 | [structure] | 12.5 | | | | 1.2 | | 33 | 12-184A-6 |
| 753 | [structure] | 12.5 | | | | 1.3 | | 33 | 12-184A-6 |

Figure 15K

| | | | | | |
|---|---|---|---|---|---|
| 754 | 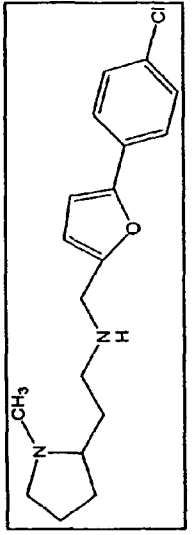 | 12.5 | | | 1.46 | | | 33 | 12-184A-6 |
| 755 | 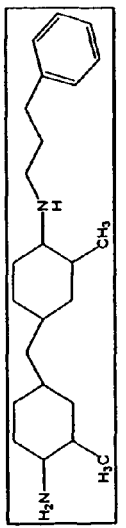 | 12.5 | | | 1.9 | | | 59 | 12-184A-6 |
| 756 | 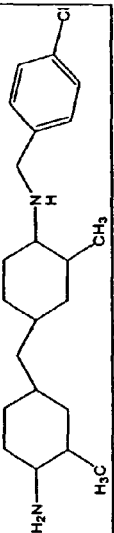 | 6.25 | | | 1.1 | | | 29 | 12-184A-6 |
| 757 | 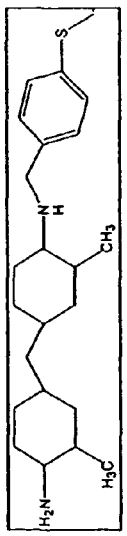 | 6.25 | | | 1.29 | | | 77 | 12-184A-6 |
| 758 | 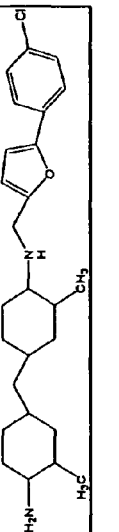 | 6.25 | | | 1.37 | | | 33 | 12-184A-6 |
Figure 15L

| | | | | | |
|---|---|---|---|---|---|
| 759 | ![structure] | 6.25 | | | 1.88 | | | 59 | 12-184A-6 |
| 760 | ![structure] | 12.5 | | | 1.6 | | | 29 | 12-184A-6 |
| 761 | ![structure] | 6.25 | | | 1.06 | | | 77 | 12-184A-6 |
| 762 | ![structure] | 1.56 | | | 1 | | | 33 | 12-184A-6 |
| 763 | ![structure] | 12.5 | | 54 | 4.32 | 2.89 | 2.93+/-0.63 | 26 | 12-184c-1 |

Figure 15M

| | | | | | | | | | |
|---|---|---|---|---|---|---|---|---|---|
| 764 | 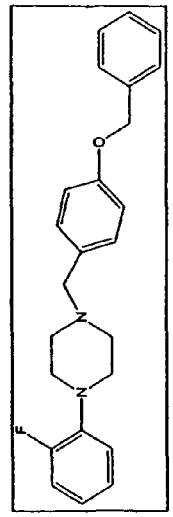 | 12.5 | | 66 | 5.28 | 1.89 | 5.23+/-0.54 | | 26 | 12-184c-1 |
| 765 | 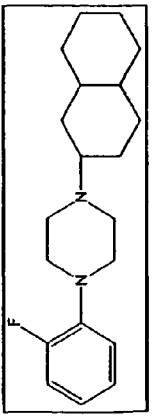 | 6.25 | 125 | 70 | 11.2 | 15.77 | | | 102 | 12-184c-1 |
| 766 | 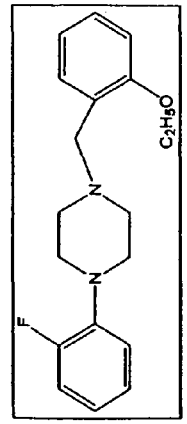 | 12.5 | 500 | 76 | 6.08 | 0.95 | 4.11+/-0.53 | | 48 | 12-184c-1 |
| 767 | 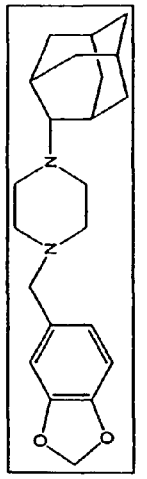 | 25 | 125 | | | 13.5 | 3.68+/-0.60 | | 98 | 12-184c-1 |
| 768 | 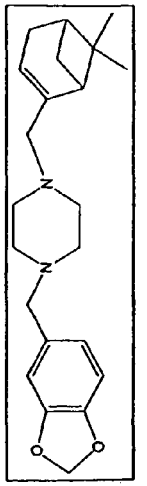 | 6.25 | | 65 | 10.4 | 1.39 | 4.22+/-0.63 | | 79 | 12-184c-1 |
Figure 15N

| | | | | | | | | | |
|---|---|---|---|---|---|---|---|---|---|
| 769 | [structure] | 6.25 | | 55 | 8.8 | 1.38 | | | 26 | 12-184c-1 |
| 770 | [structure] | 12.5 | | 69 | 5.52 | 1.5 | | | 102 | 12-184c-1 |
| 771 | [structure] | 3.13 | | 65 | 20.77 | 1.3 | | | 79 | 12-184c-1 |
| 772 | [structure] | 12.5 | | 72 | 5.76 | 1.2 | | | 84 | 12-184c-1 |
| 773 | [structure] | 12.5 | 125 | 178 | 14.24 | 2 | | | 26 | 12-184c-1 |

Figure 15O

| | | | | | | | | | |
|---|---|---|---|---|---|---|---|---|---|
| 774 | 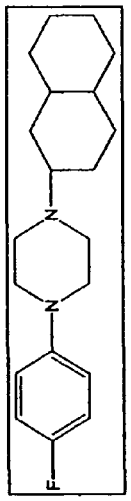 | 12.5 | | 86 | 6.88 | 25.78 | 5.49+/-0.68 | | 102 | 12-184c-2 |
| 775 | 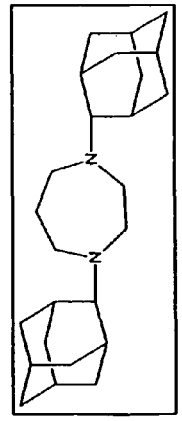 | 6.25 | 7.8 | 132 | 16.92 | 21 | 5.98+/-0.35 | | 98 | 12-184c-2 |
| 776 | 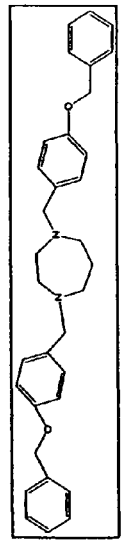 | 12.5 | 31.3 | 56 | 1.79 | 1.89 | 6.29+/-0.63 | | 26 | 12-184c-2 |
| 777 | 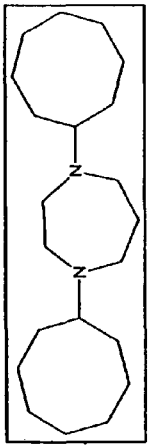 | 12.5 | 7.8 | 74 | 9.49 | 13.3 | 6.57+/-0.31 | | 65 | 12-184c-2 |
| 778 |  | 1.56 | 7.8 | 54 | 6.92 | 20.76 | 7.40+/-0.33 | | 102 | 12-184c-2 |
Figure 15P

| | | | | | | | | | |
|---|---|---|---|---|---|---|---|---|---|
| 779 | [structure] | 3.13 | 7.8 | 110 | 14.10 | 18.5 | 6.99+/-0.44+ | | 79 | 12-184c-2 |
| 780 | [structure] | 1.56 | 3.9 | 71 | 18.21 | 11.5 | 4.04+/-0.62 | | 48 | 12-184c-2 |
| 781 | [structure] | 12.5 | 62.5 | 81 | 1.30 | 0.95 | 7.14+/-0.5 | | 84 | 12-184c-2 |
| 782 | [structure] | 6.25 | 7.8 | 105 | 13.46 | 22.56 | 2.98+/-0.62 | | 117 | 12-184c-2 |
| 783 | [structure] | 12.5 | | 47 | 3.76 | 1.1 | 6.01+/-0.71 | | 102 | 12-184c-2 |

Figure 15Q

| | | | | | | | | | |
|---|---|---|---|---|---|---|---|---|---|
| 784 | 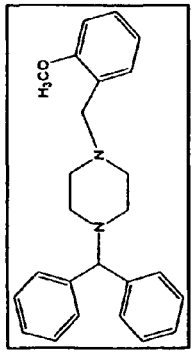 | 12.5 | | 65 | 5.2 | 0.9 | 3.85+/-0.85 | | 117 | 12-184c-2 |
| 785 | 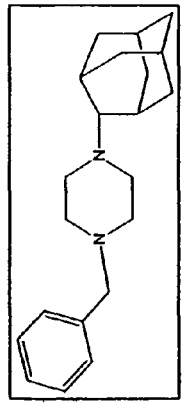 | 12.5 | 31.3 | 97 | 3.10 | 14.79 | 3.82+/-0.56 | | 98 | 12-184c-2 |
| 786 | 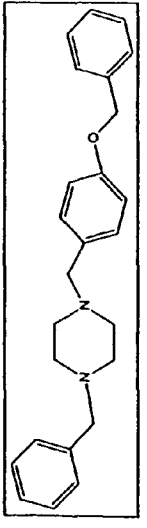 | 3.13 | | 54 | 17.25 | 1 | 4.02+/-0.71 | | 26 | 12-184c-2 |
| 787 | 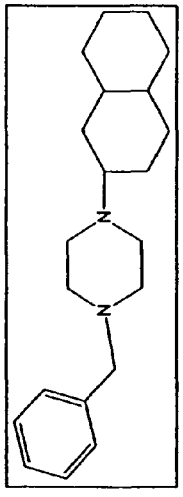 | 12.5 | | 70 | 5.6 | 3.85 | 4.53+/-0.55 | | 102 | 12-184c-2 |
| 788 | 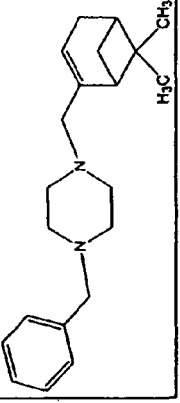 | 6.25 | | 64 | 10.24 | 1 | 4.36+/-0.59 | | 79 | 12-184c-1 |
Figure 15R

| | | | | | | | | | |
|---|---|---|---|---|---|---|---|---|---|
| 789 | (structure) | 3.13 | | 60 | 19.17 | 0.95 | 4.44+/-0.61 | | 84 | 12-184c-1 |
| 790 | (structure) | 3.13 | | | | | | | | 12-184a-10 |
| 791 | (structure) | 6.25 | | | | | | | | 12-184a-10 |
| 792 | (structure) | 6.25 | | | | | | | | 12-184b-1 A1 |
| 793 | (structure) | 12.5 | | | | | | | | 12-184b-1 G1 |

Figure 15S

| 12-184b-1 A2 | 12-184b-1 C2 | 12-184b-1 D2 | 12-184b-1 E2 | 12-184b-1 G2 |
|---|---|---|---|---|
|  |  |  |  |  |
|  |  |  |  |  |
|  |  |  |  |  |
|  |  |  |  |  |
|  |  |  |  |  |
|  |  |  |  |  |
|  |  |  |  |  |
| 6.25 | 6.25 | 12.5 | 6.25 | 12.5 |
|  |  |  |  |  |
| 794 | 795 | 796 | 797 | 798 |

Figure 15T

| | 12-184b-1 H2 | 12-184b-1 E5 | 12-184b-1 G5 | 12-184b-1 A7 | 12-184b-1 C7 |
|---|---|---|---|---|---|
| | | | | | |
| | | | | | |
| | | | | | |
| | | | | | |
| | | | | | |
| | | | | | |
| | 12.5 | 12.5 | 6.25 | 12.5 | 6.25 |
| | 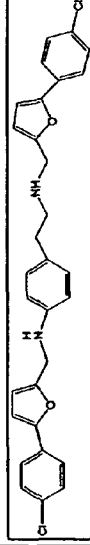 | 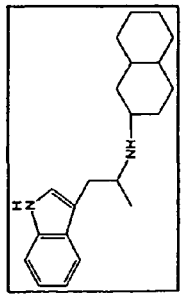 | 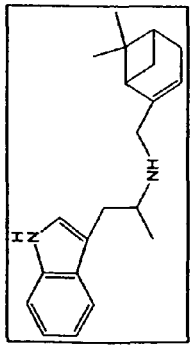 | 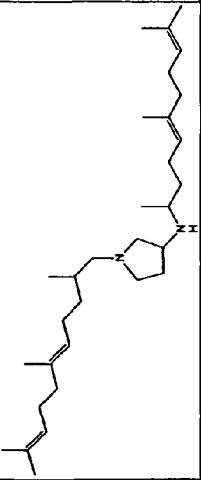 | 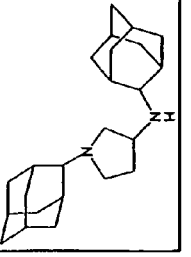 |
| | 799 | 800 | 801 | 802 | 803 |
Figure 15U

| | 12-184b-1 E8 | 12-184b-1 A10 | 12-184b-1 H11 | 12-184b-1 A12 | 12-184b-1 B12 |
|---|---|---|---|---|---|
| | | | | | |
| | | | | | |
| | | | | | |
| | | | | | |
| | | | | | |
| | | | | | |
| | | | | | |
| | 12.5 | 12.5 | 6.25 | 12.5 | 12.5 |
| | 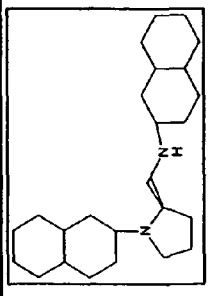 | 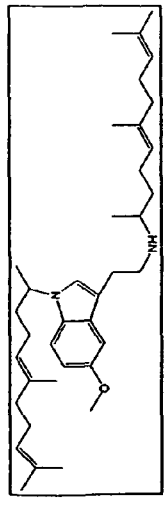 | 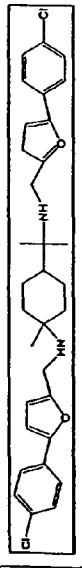 | 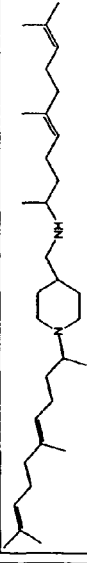 | 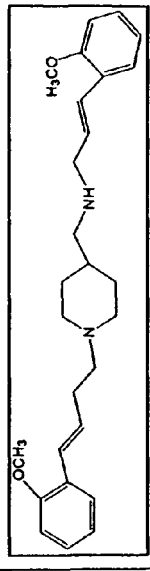 |
| | 804 | 805 | 806 | 807 | 808 |
Figure 15V

| | 12-184b-1 D12 | 12-184b-2 B2 | 12-184b-2 D2 | 12-184b-2 E2 | 12-184b-2 F2 |
|---|---|---|---|---|---|
| | | | | | |
| | | | | | |
| | | | | | |
| | | | | | |
| | | | | | |
| | | | | | |
| | | | | | |
| | 6.25 | 12.5 | 12.5 | 12.5 | 6.25 |
| | structure | structure | structure | structure | structure |
| | 809 | 810 | 811 | 812 | 813 |

Figure 15W

| | | | | | |
|---|---|---|---|---|---|
| | 12-184b-2 G2 | 12-184b-2 H2 | 12-184b-2 B6 | 12-184b-2 A8 | 12-184b-2 D8 |
| | | | | | |
| | | | | | |
| | | | | | |
| | | | | | |
| | | | | | |
| | | | | | |
| | | | | | |
| | 12.5 | 12.5 | 12.5 | 12.5 | 12.5 |
| | (structure) | (structure) | (structure) | (structure) | (structure) |
| | 814 | 815 | 816 | 817 | 818 |

Figure 15X

| | | | | | |
|---|---|---|---|---|---|
| | 12-184b-2 G8 | 12-184b-2 B11 | 12-184b-2 A12 | 12-184b-2 B12 | 12-184b-2 C12 |
| | | | | | |
| | | | | | |
| | | | | | |
| | | | | | |
| | | | | | |
| | | | | | |
| | | | | | |
| | 12.5 | 6.25 | 12.5 | | 12.5 |
| | 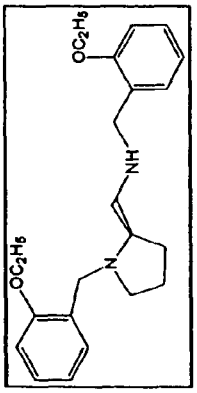 | 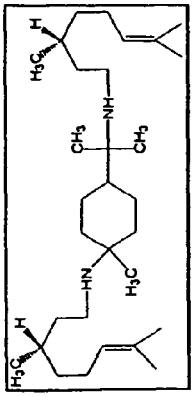 | 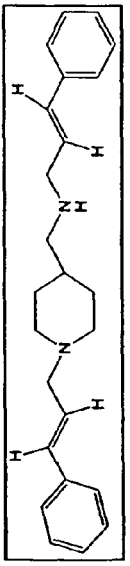 | 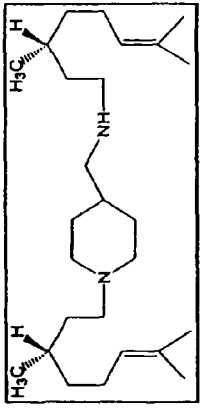 | 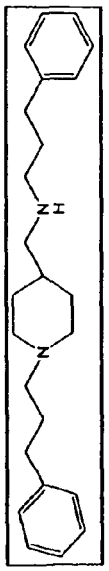 |
| | 819 | 820 | 821 | 822 | 823 |
Figure 15Y

| | | | | |
|---|---|---|---|---|
| 12-184b-2 D12 | 12-184b-2 G12 | 12-184b-4 B2 | 12-184b-4 B12 | 12-184b-6 A2 |
| | | | | |
| | | | | |
| | | | | |
| | | | | |
| | | | | |
| | | | | |
| | | | | |
| 12.5 | 12.5 | 6.25 | 12.5 | 12.5 |
| 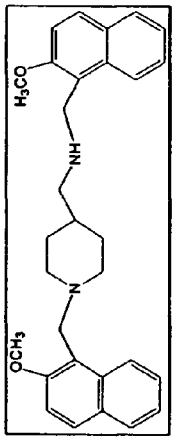 | 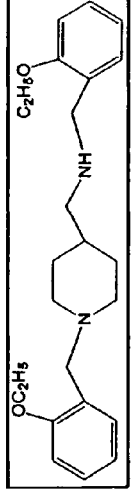 | 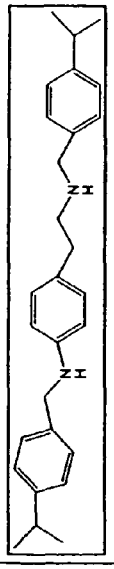 | 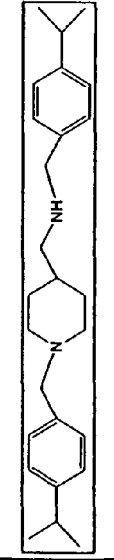 | 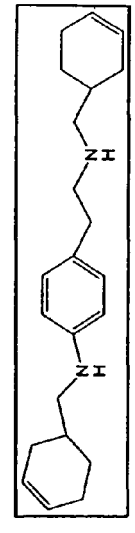 |
| 824 | 825 | 826 | 827 | 828 |
Figure 15Z

Figure 16. *In vitro* toxicity
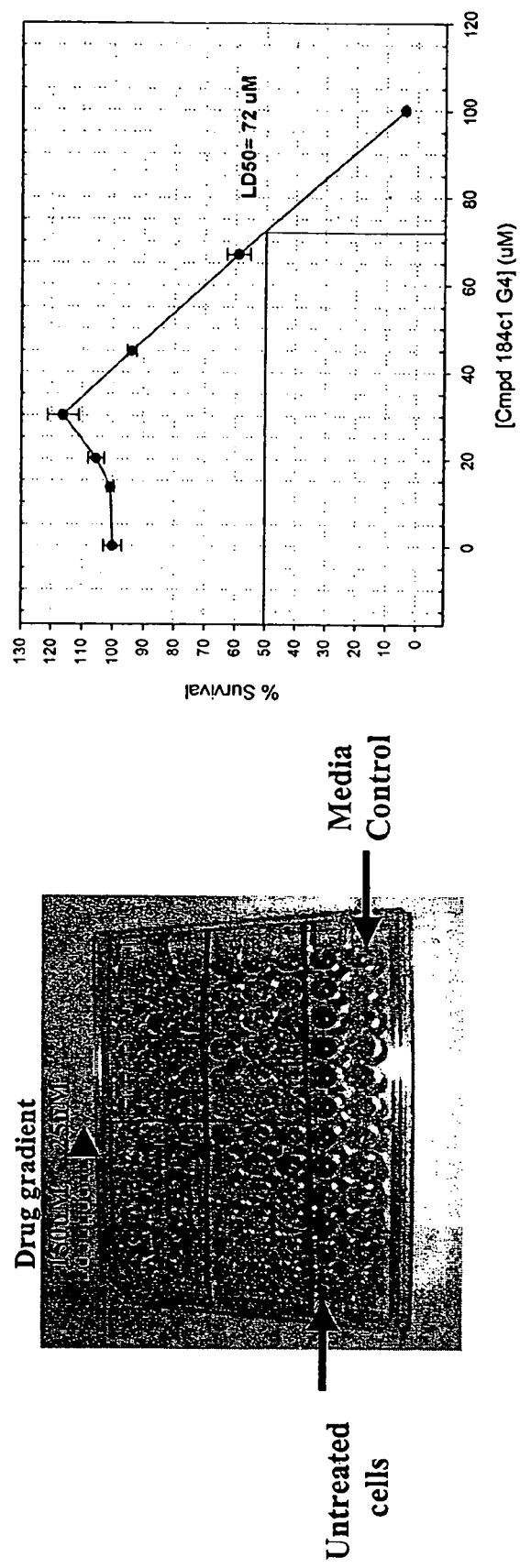

| Compound | MIC (uM) | IC50 (uM) | SI |
|---|---|---|---|
| 12-184c2 A3 | 6.25 | 90 | 14.40 |
| 12-184c2 A7 | 12.5 | 97 | 7.76 |
| 12-184c2 B3 | 12.5 | 64 | 5.12 |
| 12-184c2 B7 | 3.13 | 54 | 17.25 |
| 12-184c2 C3 | 12.5 | 100 | 8.00 |
| 12-184c2 D3 | 1.56 | 54 | 34.62 |
| 12-184c2 D6 | 12.5 | 47 | 3.76 |
| 12-184c2 D7 | 12.5 | 70 | 5.60 |
| 12-184c2 E3 | 3.13 | 60 | 19.17 |
| 12-184c2 E7 | 6.25 | 64 | 10.24 |
| 12-184c2 F3 | 1.56 | 71 | 45.51 |
| 12-184c2 G3 | 12.5 | 61 | 4.88 |
| 12-184c2 G7 | 3.13 | 60 | 19.17 |
| 12-184c2 H3 | 6.25 | 140 | 22.40 |
| 12-184c2 H6 | 12.5 | 65 | 5.20 |
| 12-184c2 D1 | 12.5 | 86 | 6.88 |
| 12-184c1 B1 | 12.5 | 54 | 4.32 |
| 12-184c1 B2 | 12.5 | 66 | 5.28 |
| 12-184c1 B4 | 6.25 | 55 | 8.80 |
| 12-184c1 B6 | 12.5 | 178 | 14.24 |
| 12-184c1 D2 | 6.25 | 70 | 11.20 |
| 12-184c1 D4 | 12.5 | 69 | 5.52 |
| 12-184c1 E3 | 6.25 | 65 | 10.40 |
| 12-184c1 E4 | 3.13 | 65 | 20.77 |
| 12-184c1 F2 | 12.5 | 76 | 6.08 |
| 12-184c1 G4 | 12.5 | 72 | 5.76 |

Table 4. Toxicity and SI of tested wells

Figure 17

| Compound | MIC (uM) | IC50 (uM) | SI |
|---|---|---|---|
| 775 | 7.8 | 132 | 16.92 |
| 776 | 31.3 | 56 | 1.79 |
| 777 | 7.8 | 74 | 9.49 |
| 778 | 7.8 | 54 | 6.92 |
| 779 | 7.8 | 110 | 14.10 |
| 780 | 3.9 | 71 | 18.21 |
| 781 | 62.5 | 81 | 1.30 |
| 782 | 7.8 | 105 | 13.46 |

Table 5. Toxicity and SI of selected compounds

Figure 18

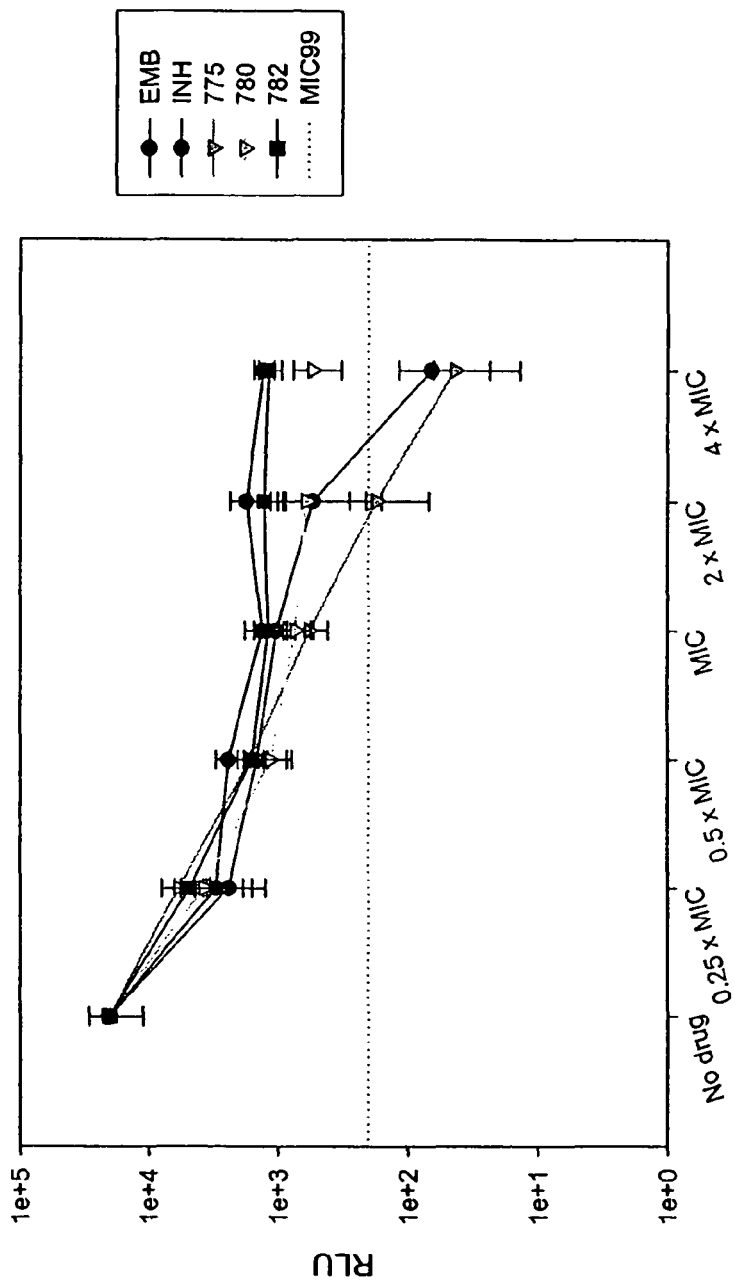
Figure 19. Efficacy of selected compounds in infected macrophages

FIGURE 21
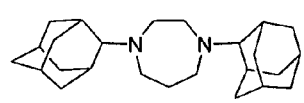 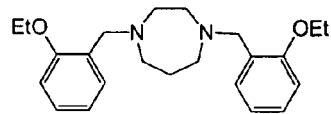 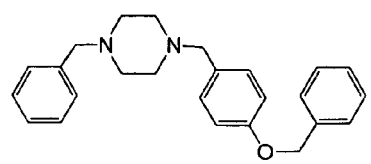
SQ775            SQ780            SQ786

FIGURE 30

| # | Structure | MIC µM | IC 50 µM | SI IC50:MIC | Luc | LogP |
|---|---|---|---|---|---|---|
| SQ775 | 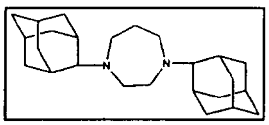 | 7.8 | 132 | 16.92 | 0.95 | 5.98+/-0.35 |
| SQ777 | 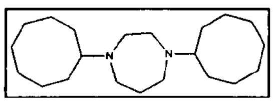 | 7.8 | 74 | 9.49 | 1.02 | 6.57+/-0.31 |
| SQ778 | 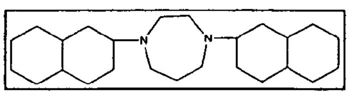 | 7.8 | 54 | 6.92 | 0.94 | 7.40+/-0.33 |
| SQ779 | 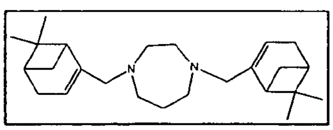 | 7.8 | 110 | 14.10 | 0.68 | 6.99+/-0.44+ |
| SQ780 | 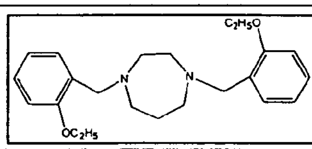 | 3.9 | 71 | 18.21 | 0.88 | 4.04+/-0.62 |
| SQ782 | 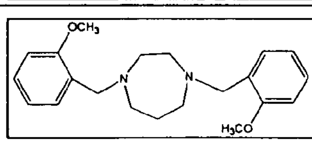 | 7.8 | 105 | 13.46 | 1.02 | 2.98+/-0.62 |
| SQ786 | 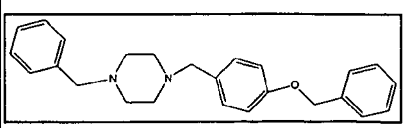 | 3.13 | 54 | 17.25 | 0. | 4.04+/-0.71 |

US 7,884,097 B2

METHODS AND COMPOSITIONS COMPRISING DIAMINES AS NEW ANTI-TUBERCULAR THERAPEUTICS

CROSS-REFERENCE TO RELATED PATENT APPLICATIONS

The present application claims priority to U.S. Provisional Patent Applications Ser. No. 60/500,531 filed on Sep. 5, 2003.

The present application is related to U.S. Provisional Patent Applications Ser. Nos. 60/381,244 filed May 17, 2002, 60/381,220 filed May 17, 2002, and 60/451,564 filed Mar. 3, 2003. The present application is also related to U.S. patent applications Ser. Nos. 10/147,587 filed May 17, 2002, Ser. No. 10/440,017 filed May 16, 2003, Ser. No. 10/441,146 filed May 19, 2003, and Ser. No. 10/441,272 filed May 19, 2003. The foregoing applications are all incorporated herein by reference.

FIELD OF INVENTION

The present invention relates to methods and compositions for treating disease caused by infectious agents, and in particular disease caused by mycobacteria. The present invention also relates to methods and compositions having improved anti-mycobacterial activity, namely compositions comprising novel diamine compounds.

BACKGROUND OF THE INVENTION

Mycobacterial infections often manifest as diseases such as tuberculosis. Human infections caused by mycobacteria have been widespread since ancient times, and tuberculosis remains a leading cause of death today. Although the incidence of the disease declined, in parallel with advancing standards of living, since the mid-nineteenth century, mycobacterial diseases still constitute a leading cause of morbidity and mortality in countries with limited medical resources. Additionally, mycobacterial diseases can cause overwhelming, disseminated disease in immunocompromised patients. In spite of the efforts of numerous health organizations worldwide, the eradication of mycobacterial diseases has never been achieved, nor is eradication imminent. Nearly one third of the world's population is infected with *mycobacterium tuberculosis* complex, commonly referred to as tuberculosis (TB), with approximately 8 million new cases, and two to three million deaths attributable to TB yearly. Tuberculosis (TB) is the cause of the largest number of human deaths attributable to a single etiologic agent (see Dye et al., J. Am. Med. Association, 282, 677-686, (1999); and 2000 WHO/OMS Press Release).

After decades of decline, TB is now on the rise. In the United States, up to 10 million individuals are believed to be infected. Almost 28,000 new cases were reported in 1990, constituting a 9.4 percent increase over 1989. A sixteen percent increase in TB cases was observed from 1985 to 1990. Overcrowded living conditions and shared air spaces are especially conducive to the spread of TB, contributing to the increase in instances that have been observed among prison inmates, and among the homeless in larger U.S. cities. Approximately half of all patients with "Acquired Immune Deficiency Syndrome" (AIDS) will acquire a mycobacterial infection, with TB being an especially devastating complication. AIDS patients are at higher risks of developing clinical TB, and anti-TB treatment seems to be less effective than in non-AIDS patients. Consequently, the infection often progresses to a fatal disseminated disease.

Mycobacteria other than *M. tuberculosis* are increasingly found in opportunistic infections that plague the AIDS patient. Organisms from the *M. avium-intracellulare* complex (MAC), especially serotypes four and eight, account for 68% of the mycobacterial isolates from AIDS patients. Enormous numbers of MAC are found (up to $10^{10}$ acid-fast bacilli per gram of tissue), and consequently, the prognosis for the infected AIDS patient is poor.

The World Health Organization (WHO) continues to encourage the battle against TB, recommending prevention initiatives such as the "Expanded Program on Immunization" (EPI), and therapeutic compliance initiatives such as "Directly Observed Treatment Short-Course" (DOTS). For the eradication of TB, diagnosis, treatment, and prevention are equally important. Rapid detection of active TB patients will lead to early treatment by which about 90% cure is expected. Therefore, early diagnosis is critical for the battle against TB. In addition, therapeutic compliance will ensure not only elimination of infection, but also reduction in the emergence of drug-resistance strains.

The emergence of drug-resistant *M. tuberculosis* is an extremely disturbing phenomenon. The rate of new TB cases proven resistant to at least one standard drug increased from 10 percent in the early 1980's to 23 percent in 1991. Compliance with therapeutic regimens, therefore, is also a crucial component in efforts to eliminate TB and prevent the emergence of drug resistant strains. Equally important is the development of new therapeutic agents that are effective as vaccines, and as treatments, for disease caused by drug resistant strains of mycobacteria.

Although over 37 species of mycobacteria have been identified, more than 95% of all human infections are caused by six species of mycobacteria: *M. tuberculosis, M. avium intracellulare, M. kansasii, M. fortuitum, M. chelonae*, and *M. leprae*. The most prevalent mycobacterial disease in humans is tuberculosis (TB) which is predominantly caused by mycobacterial species comprising *M. tuberculosis, M. bovis*, or *M. africanum* (Merck Manual 1992). Infection is typically initiated by the inhalation of infectious particles which are able to reach the terminal pathways in lungs. Following engulfment by alveolar macrophages, the bacilli are able to replicate freely, with eventual destruction of the phagocytic cells. A cascade effect ensues wherein destruction of the phagocytic cells causes additional macrophages and lymphocytes to migrate to the site of infection, where they too are ultimately eliminated. The disease is further disseminated during the initial stages by the infected macrophages which travel to local lymph nodes, as well as into the blood stream and other tissues such as the bone marrow, spleen, kidneys, bone and central nervous system. (See Murray et al. *Medical Microbiology*, The C.V. Mosby Company 219-230 (1990)).

There is still no clear understanding of the factors which contribute to the virulence of mycobacteria. Many investigators have implicated lipids of the cell wall and bacterial surface as contributors to colony morphology and virulence. Evidence suggests that C-mycosides, on the surface of certain mycobacterial cells, are important in facilitating survival of the organism within macrophages. Trehalose 6,6' dimycolate, a cord factor, has been implicated for other mycobacteria.

The interrelationship of colony morphology and virulence is particularly pronounced in *M. avium*. *M. avium* bacilli occur in several distinct colony forms. Bacilli which grow as transparent, or rough, colonies on conventional laboratory media are multiplicable within macrophages in tissue culture, are virulent when injected into susceptible mice, and are resistant to antibiotics. Rough or transparent bacilli, which are maintained on laboratory culture media, often spontaneously assume an opaque R colony morphology, at which time they are not multiplicable in macrophages, are avirulent in mice, and are highly susceptible to antibiotics. The differences in colony morphology between the transparent, rough and opaque strains of *M. avium* are almost certainly due to the presence of a glycolipid coating on the surface of transparent and rough organisms which acts as a protective capsule. This capsule, or coating, is composed primarily of C-mycosides which apparently shield the virulent *M. avium* organisms from lysosomal enzymes and antibiotics. By contrast, the non-virulent opaque forms of *M. avium* have very little C-mycoside on their surface. Both the resistance to antibiotics and the resistance to killing by macrophages have been attributed to the glycolipid barrier on the surface of *M. avium.*

Diagnosis of mycobacterial infection is confirmed by the isolation and identification of the pathogen, although conventional diagnosis is based on sputum smears, chest X-ray examination (CXR), and clinical symptoms. Isolation of mycobacteria on a medium takes as long as four to eight weeks. Species identification takes a further two weeks. There are several other techniques for detecting mycobacteria such as the polymerase chain reaction (PCR), mycobacterium tuberculosis direct test, or amplified mycobacterium tuberculosis direct test (MTD), and detection assays that utilize radioactive labels.

One diagnostic test that is widely used for detecting infections caused by *M. tuberculosis* is the tuberculin skin test. Although numerous versions of the skin test are available, typically one of two preparations of tuberculin antigens are used: old tuberculin (OT), or purified protein derivative (PPD). The antigen preparation is either injected into the skin intradermally, or is topically applied and is then invasively transported into the skin with the use of a multiprong inoculator (Tine test). Several problems exist with the skin test diagnosis method. For example, the Tine test is not generally recommended because the amount of antigen injected into the intradermal layer cannot be accurately controlled. (See Murray et al. *Medical Microbiology*, The C.V. Mosby Company 219-230 (1990)).

Although the tuberculin skin tests are widely used, they typically require two to three days to generate results, and many times, the results are inaccurate since false positives are sometimes seen in subjects who have been exposed to mycobacteria, but are healthy. In addition, instances of mis-diagnosis are frequent since a positive result is observed not only in active TB patients, but also in persons vaccinated with Bacille Calmette-Guerin (BCG), and those who had been infected with mycobacteria, but have not developed the disease. It is hard therefore, to distinguish active TB patients from the others, such as household TB contacts, by the tuberculin skin test. Additionally, the tuberculin test often produces a cross-reaction in those individuals who were infected with mycobacteria other than *M. tuberculosis* (MOTT). Therefore, diagnosis using the skin tests currently available is frequently subject to error and inaccuracies.

The standard treatment for tuberculosis caused by drug-sensitive organisms is a six-month regimen consisting of four drugs given for two months, followed by two drugs given for four months. The two most important drugs, given throughout the six-month course of therapy, are isoniazid and rifampin. Although the regimen is relatively simple, its administration is quite complicated. Daily ingestion of eight or nine pills is often required during the first phase of therapy; a daunting and confusing prospect. Even severely ill patients are often symptom free within a few weeks, and nearly all appear to be cured within a few months. If the treatment is not continued to completion, however, the patient may experience a relapse, and the relapse rate for patients who do not continue treatment to completion is high. A variety of forms of patient-centered care are used to promote adherence with therapy. The most effective way of ensuring that patients are taking their medication is to use directly observed therapy, which involves having a member of the health care team observe the patient take each dose of each drug. Directly observed therapy can be provided in the clinic, the patient's residence, or any mutually agreed upon site. Nearly all patients who have tuberculosis caused by drug-sensitive organisms, and who complete therapy will be cured, and the risk of relapse is very low ("Ending Neglect: The Elimination of Tuberculosis in the United States" ed. L. Geiter Committee on the Elimination of Tuberculosis in the United States Division of Health Promotion and Disease Prevention, Institute of Medicine. Unpublished.)

What is needed are effective therapeutic regimens that include improved vaccination and treatment protocols. Currently available therapeutics are no longer consistently effective as a result of the problems with treatment compliance, and these compliance problems contribute to the development of drug resistant mycobacterial strains.

Ethambutol (EMB) is a widely used antibiotic for the treatment of TB, with over 300 million doses delivered for tuberculosis therapy in 1988.

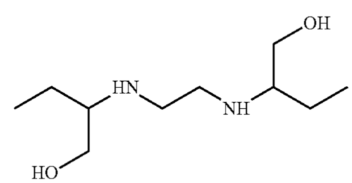

Ethambutol

Ethambutol, developed by Lederle Laboratories in the 1950s, has low toxicity and is a good pharmacokinetic. However, ethambutol has a high Minimum Inhibition Concentration (MIC) of about 5 μg/ml, and can cause optic neuritis. Thus, there is an increasing need for new, and more effective, therapeutic compositions (See for example, U.S. Pat. Nos. 3,176,040, 4,262,122; 4,006,234; 3,931,157; 3,931,152; U.S. Re. 29,358; and Häusler et al., Bioorganic & Medicinal Chemistry Letters 11 (2001) 1679-1681). In the decoder years since the discovery of the beneficial effects of ethambutol, few pharmacological advances in TB treatment have been developed. Moreover, with the combined emergence of drug resistant strains, and the more prevalent spread of mycobacterial disease, it is becoming seriously apparent that new therapeutic compositions are crucial in the fight against tuberculosis.

Clearly effective therapeutic regimens that include improved vaccination and treatment protocols are needed. A therapeutic vaccine that would prevent the onset of tuberculosis, and therefore eliminate the need for therapy is desirable. Although currently available therapeutics such as ethambutol are effective, the emergence of drug resistant strains has necessitated new formulations and compositions that are more versatile than ethambutol. What is needed are new antitubercular drugs that provide highly effective treatment, and shorten and simplify tuberculosis chemotherapy.

SUMMARY OF THE INVENTION

The present invention comprises methods and compositions comprising novel diamine compounds effective for the treatment of infectious disease. The compositions of the present invention have improved anti-mycobacterial activity, and more particularly, improved anti-tuberculosis activity.

The present invention contemplates novel diamine compositions which are prepared by reductive alkylation of diamines using carbonyl compounds and resin bound trimethylammonium cyanoborohydride.

The diamine compositions described herein are synthesized and screened for activity as follows. A chemical library of diamines is synthesized using solution phase chemistry. The diamines are screened for anti-TB activity using in vitro biological assays, including a High-Throughput Screening (HTS) assay based on the recently completed genomic sequence of *M. tuberculosis*, and a Minimum Inhibition Concentration (MIC) assay.

The methods and compositions described herein comprise diamine compositions that are effective against disease caused by infectious organisms, including, but not limited to, bacteria and viruses.

One embodiment of the invention provides methods and compositions comprising diamine compositions that are effective against mycobacterial disease.

Another embodiment of the invention provides methods and compositions comprising diamine compositions that have MIC of 50 µM or lower for mycobacterial disease.

Another embodiment of the present invention comprises diamine compositions that have an MIC of 25 µM or lower for mycobacterial disease.

Yet another embodiment of the present invention comprises diamine compositions that have an MIC of 12.5 µM or lower for mycobacterial disease.

Another embodiment of the present invention comprises diamine compositions that have an MIC of 5 µM or lower for mycobacterial disease.

In another embodiment of the present invention, the methods and compositions comprise diamine compositions with HTS Luc activity of 10% or greater.

The present invention contemplates various salt complexes and other substituted derivatives of the diamine compositions.

The present invention also contemplates enantiomers and other stereoisomers of the diamine compositions and their substituted derivatives. The present invention further contemplates treatment for animals, including, but not limited to, humans.

Accordingly, it is an object of the present invention to provide methods and compositions for the treatment and prevention of diseases caused by infectious agents.

Another object of the present invention is to provide methods and compositions for the treatment and prevention of mycobacterial disease, including but not limited to, tuberculosis.

Yet another object of the present invention is to provide methods and compositions for the treatment and prevention of infectious diseases using compositions comprising diamine compositions.

Another object of the present invention is to provide methods and compositions for the treatment and prevention of mycobacterial disease using compositions comprising diamine compositions.

Still another object of the present invention is to provide methods and compositions for the treatment and prevention of tuberculosis using compositions comprising diamine compositions.

Another object of the present invention is to provide methods and compositions for the treatment and prevention of tuberculosis using compositions comprising diamine compositions, wherein the diamine has an MIC of 50 µM, or less.

Another object of the present invention is to provide methods and compositions for the treatment and prevention of tuberculosis using compositions comprising diamine compositions, wherein the diamine has an MIC of 25 µM, or less.

Another object of the present invention is to provide methods and compositions for the treatment and prevention of tuberculosis using compositions comprising diamine compositions, wherein the diamine has an MIC of 12.5 µM, or less.

Yet another object of the present invention is to provide methods and compositions for the treatment and prevention of tuberculosis using compositions comprising diamine compositions, wherein the diamine has an MIC of 5 µM, or less.

Yet another object of the present invention is to provide methods and compositions for the treatment and prevention of tuberculosis using compositions comprising diamine compositions, wherein the diamine has HTS/Luc activity of 10% or greater.

Yet another object of the present invention is to provide compositions for the therapeutic formulation for the treatment and prevention of mycobacterial disease.

Another object of the present invention is to provide compositions for therapeutic formulations for the treatment and prevention of mycobacterial disease caused by mycobacterial species comprising *M. tuberculosis* complex, *M. avium intracellulare*, *M. kansarii*, *M. fortuitum*, *M. chelonoe*, *M. leprae*, *M. africanum*, *M. microti*, *M. avium paratuberculosis*, or *M. bovis*.

These and other objects, features and advantages of the present invention will become apparent after a review of the following detailed description of the disclosed embodiments and the appended claims.

BRIEF DESCRIPTION OF THE FIGURES

FIGS. 1-4 provide representative structures of starting diamine products.

FIGS. 5A and 5B provide Table 1 listing the chemical names of the structures provided in FIGS. 1-4.

FIG. 6A-6C provide Table 2 listing carbonyl compounds used to generate the diamine compositions of the present invention.

FIG. 7 provides the organizational scheme used to synthesize diamine compositions of the present invention.

FIG. 8 provides carbonyl compounds used in synthesis.

FIG. 9 is a graph showing the results of a luciferase assay used to evaluate the inhibitory effects of various compositions on cell wall biosynthesis.

FIG. 10 provides Luc data for representative wells.

FIG. 11 provides a schematic showing the deconvolution procedure.

FIG. 12 provides a schematic showing a deconvolution template.

FIG. 13 provides representative Luc data for deconvoluted samples.

FIG. 14 provides a graph showing the occurrence of synthons derived from starting carbonyl compounds in the hits.

FIG. 16 provides the results of in vitro toxicity testing.

FIG. 17 provides Table 4 listing the minimum inhibition concentration (MIC) and selectivity index (SI) for deconvoluted wells with the best MICs.

FIG. 18 provides Table 5 listing MIC (µM), IC50 (µM), and SI for selected compounds.

FIG. 19 provides a graph showing the efficacy of selected compounds in infected macrophages.

FIG. 21 provides of chemical structures of selected compounds tested for efficacy against *M. tuberculosis* in vivo.

FIG. 30 provides a graph showing the inhibitory activity of tested compounds against *M.tuberculosis* in TB-infected mouse macrophage RAW 264.7 cells at five concentrations. A bioluminescence-based assay with a reporter strain of *M. tuberculosis* was employed.

DETAILED DESCRIPTION

Figure 15A:
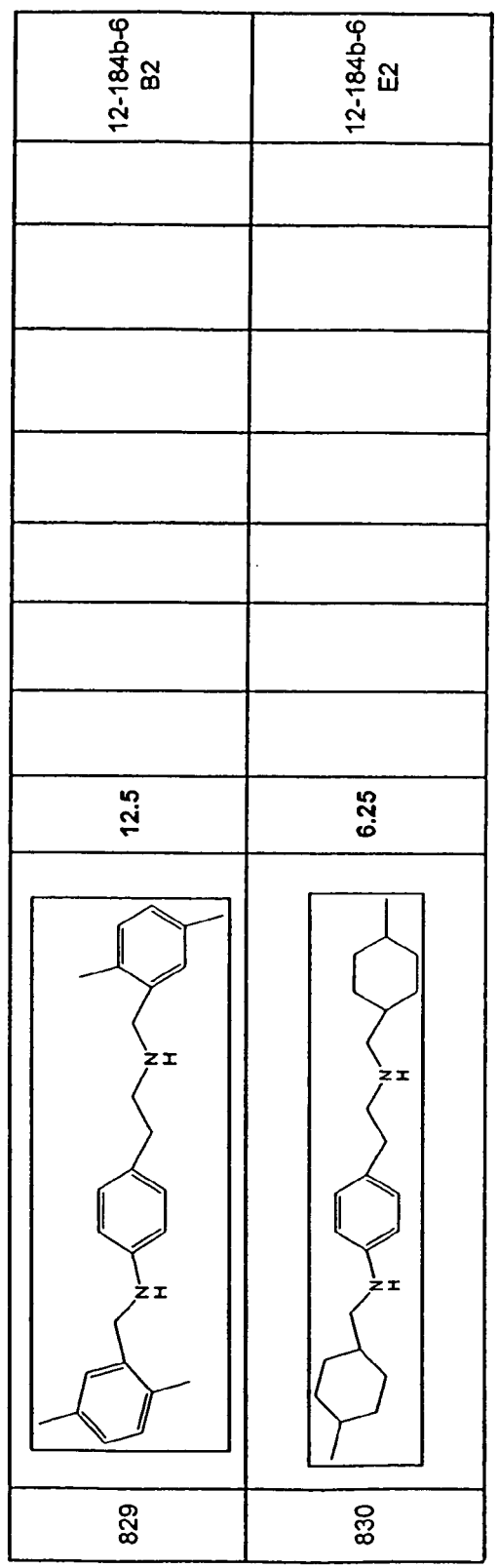
FIGS. 15A-AA provides Table 3 listing individual diamine structures identified as potent anti-TB compounds.

The present invention may be understood more readily by reference to the following detailed description of the specific embodiments included herein. However, although the present invention has been described with reference to specific details of certain embodiments thereof, it is not intended that such details should be regarded as limitations upon the scope of the invention. The entire text of the references mentioned herein are hereby incorporated in their entireties by reference including U.S. Provisional Patent Applications Ser. Nos. 60/500,531 filed Sep. 5, 2003, 60/381,244 filed May 17, 2002, 60/381,220 filed May 17, 2002, and 60/451,564 filed Mar. 3, 2003; and U.S. patent applications Ser. Nos. 10/147, 587 filed May 17, 2002, Ser. No. 10/440,017 filed May 16, 2003, Ser. No. 10/441,146 filed May 19, 2003, and Ser. No. 10/441,272 filed May 19, 2003.

Mycobacterial infections, such as those causing tuberculosis, once thought to be declining in occurrence, have rebounded, and again constitute a serious health threat. Tuberculosis (TB) is the cause of the largest number of human deaths attributed to a single etiologic agent with two to three million people infected with tuberculosis dying each year. Areas where humans are crowded together, or living in substandard housing, are increasingly found to have persons affected with mycobacteria. Individuals who are immunocompromised are at great risk of being infected with mycobacteria and dying from such infection. In addition, the emergence of drug-resistant strains of mycobacteria has led to treatment problems of such infected persons.

Many people who are infected with mycobacteria are poor, or live in areas with inadequate healthcare facilities. As a result of various obstacles (economical, education levels, etc.), many of these individuals are unable to comply with prescribed therapeutic regimens. Ultimately, persistent noncompliance by these and other individuals results in the prevalence of disease. This noncompliance is frequently compounded by the emergence of drug-resistant strains of mycobacteria. Effective compositions and vaccines that target various strains of mycobacteria are necessary to bring the increasing number of tuberculosis cases under control.

Chemotherapy is a standard treatment for tuberculosis. Some current chemotherapy treatments require the use of three or four drugs, in combination, administered daily for two months, or administered biweekly for four to twelve months. Table 1 lists several treatment schedules for standard tuberculosis drug regimens.

TABLE 1

Treatment Schedules for Standard TB Drug Regimens.

| STANDARD DRUG REGIMEN | INDUCTION PHASE Dosing Schedule | DURATION | DRUG | CONTINUATION PHASE Dosing Schedule | DURATION |
|---|---|---|---|---|---|
| Isoniazid | Daily, DOT | 8 weeks | Isoniazid | 2/week, DOT | 16 weeks |
| Rifampicin | Daily, DOT | 8 weeks | Rifampicin | 2/week, DOT | 16 weeks |

TABLE 1-continued

Treatment Schedules for Standard TB Drug Regimens.

| STANDARD DRUG REGIMEN | INDUCTION PHASE Dosing Schedule | DURATION | DRUG | CONTINUATION PHASE Dosing Schedule | DURATION |
|---|---|---|---|---|---|
| Pyrazinamide | Daily, DOT | 8 weeks | | | |
| Ethambutol or Streptomycin | Daily, DOT | 8 weeks | | | |

Decades of misuse of existing antibiotics and poor compliance with prolong and complex therapeutic regimens has led to mutations of the mycobacterium tuberculosis and has created an epidemic of drug resistance that threatens tuberculosis control worldwide. The vast majority of currently prescribed drugs, including the front line drugs, such as isoniazid, rifampin, pyrazinamide, ethambutol and streptomycin were developed from the 1950s to the 1970s. Thus, this earlier development of tuberculosis chemotherapy did not have at its disposal the implications of the genome sequence of *Mycobacterium tuberculosis*, the revolution in pharmaceutical drug discovery of the last decades, and the use of rational drug testing and combinational chemistry.

Consequently, the treatments of drug-resistant *M. tuberculosis* strains, and latent tuberculosis infections, require new anti-tuberculosis drugs that provide highly effective treatments, and shortened and simplified tuberculosis chemotherapies. Moreover, it is desirable that these drugs be prepared by a low-cost synthesis, since the demographics of the disease dictate that cost is a significant factor.

The present invention provides methods and compositions comprising a novel class of diamine compounds effective in treatment and prevention of disease caused by microorganisms including, but not limited to, bacteria. In particular, the methods and compositions of the present invention are effective in inhibiting the growth of the microorganism, *M. tuberculosis*. The methods and compositions of the present invention are intended for the treatment of mycobacteria infections in human, as well as other animals. For example, the present invention may be particularly useful for the treatment of cows infected by *M. bovis*.

As used herein, the term "tuberculosis" comprises disease states usually associated with infections caused by mycobacteria species such as those comprising *M. tuberculosis* complex. The term "tuberculosis" is also associated with mycobacterial infections caused by mycobacteria other than *M. tuberculosis* (MOTT). Other mycobacterial species include, but are not limited to, *M. avium-intracellulare, M. kansarii, M. fortuitum, M. chelonae, M. leprae, M. africanum,* and *M. microti, M. avium paratuberculosis, M. intracellulare, M. scrofulaceum, M. xenopi, M. marinum, M. ulcerans*.

The present invention further comprises methods and compositions effective for the treatment of infectious disease including, but not limited to, those caused by bacterial, mycological, parasitic, and viral agents. Examples of such infectious agents include the following: staphylococcus, streptococcaceae, neisseriaaceae, cocci, enterobacteriaceae, pseudomonadaceae, vibrionaceae, campylobacter, pasteurellaceae, bordetella, francisella, brucella, legionellaceae, bacteroidaceae, gram-negative bacilli, clostridium, corynebacterium, propionibacterium, gram-positive bacilli, anthrax, actinomyces, nocardia, mycobacterium, treponema, borrelia, leptospira, mycoplasma, ureaplasma, rickettsia, chlamydiae, systemic mycoses, opportunistic mycoses, protozoa, nematodes, trematodes, cestodes, adenoviruses, herpesviruses, poxviruses, papovaviruses, hepatitis viruses, orthomyxoviruses, paramyxoviruses, coronaviruses, picomaviruses, reoviruses, togaviruses, flaviviruses, bunyaviridae, rhabdoviruses, human immunodeficiency virus and retroviruses.

The present invention further provides methods and compositions useful for the treatment of infectious disease, including by not limited to, tuberculosis, leprosy, Crohn's Disease, aquired immunodeficiency syndrome, lyme disease, cat-scratch disease, Rocky Mountain Spotted Fever and influenza.

Diamine Compositions

While investigating the structural diversity and the influence of a modified linker between two nitrogen atoms on the activity against *M. tuberculosis* of ethambutol analogues, and evaluating Structure-Activity Relationship (SAR) of the hit compounds in the series, solution phase chemistry was pursued to generate a small library of structurally diverse diamines by one-step derivatization of commercially available diamines.

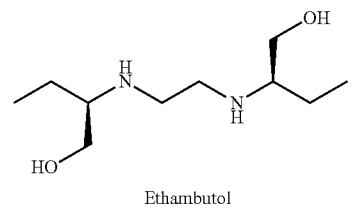

Ethambutol

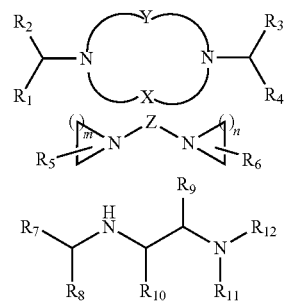

Selected diamines obtained in the series

Synthesis of the Library

The 5,000 compound library was prepared by reductive alkylation of 60 commercially available amines (FIGS. 1-4 and Table 1, FIGS. 5A-B) using 84 commercially available carbonyl compounds (Table 2, FIGS. 6A-C) and polymer/resin bound trimethylammonium cyanoborohydride (Scheme 1 (below)).

tion of the diamines with a primary amino group led, as expected, to the formation of mixtures of mono- and double-alkylated products, and syntheses outcomes were dependent Scheme 1. Solution phase synthesis of the diamines.

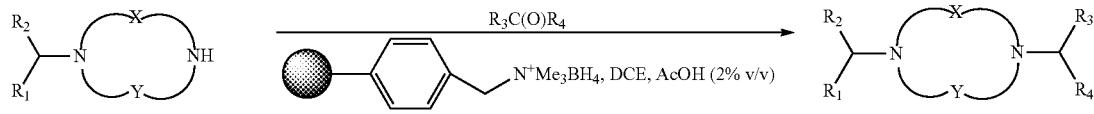

The carbonyl compounds (64 aldehydes and 20 ketones) were organized in the 96-well format, where each individual compound was placed as a 1.2 M solution in dichloroethane into individual wells of the master plate, FIGS. 7 and 8. Starting diamines were organized into four groups based on their steric and electronic characteristics (FIGS. 1-4). The diamine compounds in each group were combined and used as mixtures of 20 (Group 1, FIG. 1), 12 (Group 2, FIG. 2), 15 (Group 3, FIG. 3), or 12 (Group 4, FIG. 4) to react with individual carbonyl compounds. Four reaction plates were generated, one reaction plate per group of diamines. During synthesis, each well on the reaction plate would have a mixture of the diamines were to react with each individual carbonyl compound so, that final products were also formed as mixtures of 20, 13, 15, or 12 compounds per well.

For example, the diamines of the Group 1 were combined in equimolar amounts and dissolved in dichoroethane to yield 1.2 M stock solution that was evenly distributed (0.03 ml per well) into 84 wells of a 96-well chemically resistant reaction plate (FlexChem system by Robbins Scientific, Sunnyvale, Calif.), FIG. 7. The carbonyl compounds were then added into proper wells, one compound per well so, that a carbonyl compound from well A1 of the master plate was transferred into well A1 of the reaction plate, from well A2 of the master plate into well A2 of the reaction plate and so on. After 5-10 min, the resin bound catalyst was added and the reaction continued for 24-36 hours. Resulting diamines were obtained as mixtures of 20 compounds per well.

Quality assessment of the prepared library of diamines was done by Electrospray Ionization Mass Spectrometry, of 12 randomly selected samples per plate, 14% of the total number. Successful production of a compound was based on an appearance of a molecular ion of the calculated mass. Based on MS analysis, out of targeted 5,040 compounds, 4,788 diamines were actually formed (95%). Purity of the synthesized compounds was found to be 50-95% (based on MS data) and so the compounds were forwarded into the testing stage without purification.

Reactivity of the Diamines and Carbonyl Compounds

In addition to the information about the number and nature of the compounds being produced, mass spectroscopy provided sufficient data to estimate the reactivity of starting diamines and carbonyl reagents and their influence on the product formation.

Reductive alkylation of secondary amines was not of a concern, since a priori those compounds could yield only mono alkylated compounds, and, thus, a makeup of the product mixtures was easy to predict. In this regard, interpretation of the MS spectra of pool mixtures derived from the reactions of Group 3 diamines (mostly substituted piperazines) was straightforward due to the fact that every starting diamine gave only one product. For the rest of the library, derivatization of the diamines with a primary amino group led, as expected, to the formation of mixtures of mono- and double-alkylated products, and syntheses outcomes were dependent upon the reactivity of both diamine and carbonyl compounds. Since we used a large excess of the carbonyl reagents, for those starting diamine compounds that contained two primary amino groups or one primary and one secondary amino groups in the molecule (such as 4-(2-aminoethyl)morpholine or N-phenylethyldiamine), formation of two- or three component mixtures from the same starting diamines was unavoidable. However, diamines with sterically hindered amino group (3-aminoquinonucledine, for example) formed exclusively mono alkylated products.

Reductive alkylation by ketones regardless of nature of the starting diamines was found to proceed with a sole formation of mono alkylated products. Mono alkylation of the primary amino group was also the only or a major process in the reactions that involved aldehydes such as 4-(dimethylamino)benzaldehyde, 2-nitrobenzaldehyde, indol-3-carboxaldehyde, 1-methyl-2-pyrrolecarboxaldehyde, 4-quinolinecarboxaldehyde or 2- or 3-hydroxy substituted benzaldehydes (2,3-dihydroxybenzaldehyde or 2-hydroxy-4-methoxybenzaldehyde). Sterically hindered 5-norbornene-2-carboxaldehyde and diphenylacetaldehyde always produced roughly equal mixture of mono- and double-alkylated products. 2-Methoxycinnamaldehyde, hydrocinnamaldehyde, citronellal, and 5-(4-chlorophenyl)furfural favored double alkylation, and in some cases the reactions with these compounds proceeded even further.

Screening the Library against M. tuberculosis and Deconvolution of Active Mixtures Activity of prepared diamines against M. tuberculosis was tested (1) by direct determination of the minimum inhibitory concentration (MIC) using microdilution method, and (2) in a high-throughput assay (HTS) with recombinant mycobacteria containing a promoter fusion of luciferase to Rv0341 (FIG. 9) that was shown to inhibit cell wall biosynthesis of Mycobacteria tuberculosis (Lee, R. et al. J. Comb. Chem 2003, U.S. patent application Ser. No. 10/147,587). Examples of the Luc data are presented in the FIG. 10.

It was found that out of 386 synthesized compound mixtures, 176 were active against M.tb.: 192 mixtures had MICs of 12.5 μM or less; 31 mixtures showed activity in the luc assay (>1.5×control); and 20 compound mixtures were active in both assays.

Wells possessing activity (>1.5×control) in the HTS Luc assay and/or with an MIC of <12.5 μM were selected for deconvolutions (FIGS. 11 and 12). Deconvolutions were performed by the discrete re-synthesis of the diamine compounds in 96-well format and the same synthetic route (Scheme 1). The same screening tests were used for every deconvoluted plate (FIG. 13). We identified a number of carbonyl compounds that contributed the most to the anti-TB activity and provided the highest number of hits (FIG. 14).

Ongoing deconvolutions identified over 100 individual diamines of novel structures as potent anti-TB compounds (Table 3, FIG. 15).

In vitro Toxicity Evaluation

Deconvoluted wells with the best MICs were tested in an in vitro model of toxicity with Vero monkey kidney cells using MTS assay (Metabolizm of Tetrazolium Salts), FIG. 16. The data from this toxicity testing and the MIC data were used to calculate a selectivity index (SI), the ratio of IC50:MIC (Table 4, FIG. 17), an important selection criteria for moving the compounds forward into advanced in vitro and in vivo studies. Selectivity Indexes were ranged from 3.76 to 45.51.

Nine compounds of acceptable purity (90% or greater, MS data) were prepared on a larger scale using the same protocol and used without additional purification for in vitro studies. The same set of tests was applied to evaluate their activity against M.tb. and in vitro toxicity, obtained results are summarized in the Table 3 (FIG. 15) and Table 5 (FIG. 18).

Efficacy of Selected Compounds in Macrophages

Three compounds with high SI (#775, 780, and 782) were tested for in vitro efficacy in macrophages: RAW 264.7 (mouse macrophage) cells were infected 1:20 with M.tb luciferase reporter strain pSMT1 (hsp60 promoter driven luciferase) and then treated with drugs for 6 days, measuring M.tb viability at 4 timepoints. The experiments were run at five different concentrations: MIC, 025×MIC, 0.5×MIC, 2×MIC, and 4×MIC. The tested compounds were found to be equal or superior to ethambutol (FIG. 19) and the compound 775 was as effective as isoniazid.

Figure 20A:
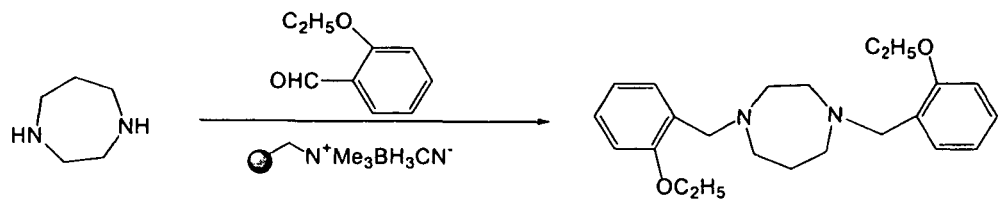
FIGS. 20A-J provides chemical structures of selected preferred compounds.

Selected examples of some preferred compounds are provided below (with corresponding structures in FIGS. 20A-J:

FIG. 20A: N,N'-Bis(2-Ethoxybenzyl)homopiperazine, compound #780; MIC 1.56 uM; IC50 71 uM; SI 18.21; LogP 4.04; obtained from homopiperazine and 2-ethoxybenzaldehyde.

Figure 20B:
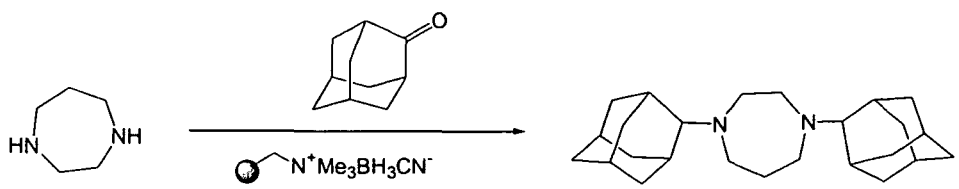

FIG. 20B: N,N'-Bis(2-Adamantane)homopiperazine, compound #775; MIC 7.8 uM; IC50 132 uM; SI 16.92; LogP 5.98: obtained from homopiperazine and 2-adamantanone.

Figure 20C:
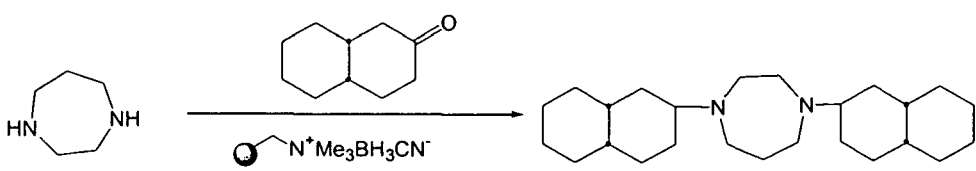

FIG. 20C: N,N'-Bis(2-Decalone)homopiperazine, compound #778; MIC 7.8 uM; IC50 54 uM; SI 6.92; LogP 7.4: obtained from homopiperazine and 2-decalone.

Figure 20D:
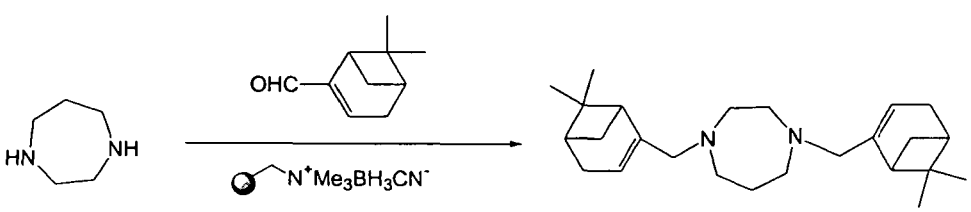

FIG. 20D: N,N'-Bis(2-Myrtanyl)homopiperazine, compound #779; MIC 7.8 uM; IC50 110 uM; SI 14.1; LogP 6.99; obtained from homopiperazine and (1R)-(−)-myrtenal.

Figure 20E:
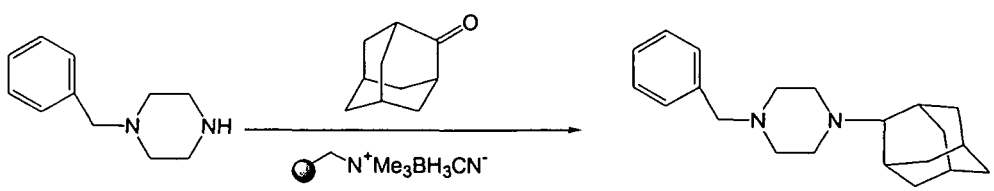

FIG. 20E: N-Benzyl-N'-2-Adamantylpiperazine, compound #785; MIC 12.5 uM; IC50 97 uM; SI 7.76; LogP 3.82; obtained from N-benzylpiperazine and 2-adamantanone.

Figure 20F:
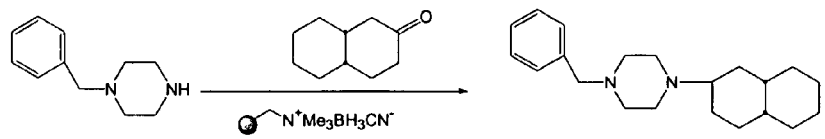

FIG. 20F: N-Benzyl-N'-2-Decalonepiperazine, compound #787; MIC 12.5 uM; IC50 70 uM; SI 5.6; LogP 4.53; obtained from N-benzylpiperazine and 2-decalone.

Figure 20G:
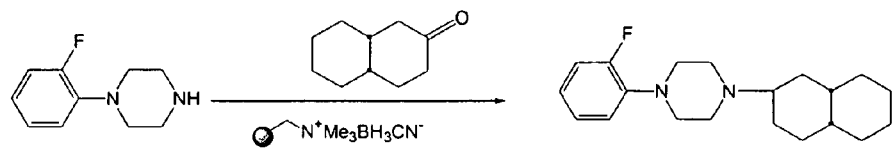

FIG. 20G: N-(2-Fluorophenyl)-N'-(2-decalone)piperazine, compound #765; MIC 6.25 uM; IC50 70 uM; SI 11.2; obtained from 1-(2-fluorophenyl)piperazine and 2-decalone.

Figure 20H:
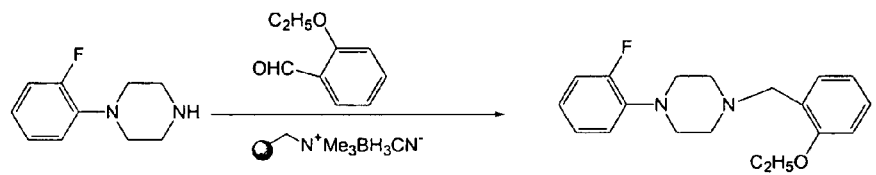

FIG. 20H: N-(2-Fluorophenyl)-N'-(2-ethoxybenzyl)piperazine, compound # 766; MIC 12.5 uM; IC50 76 uM; SI 6.08; obtained from 1-(2-fluorophenyl)piperazine and 2-ethoxybenzaldehyde.

Figure 20I:
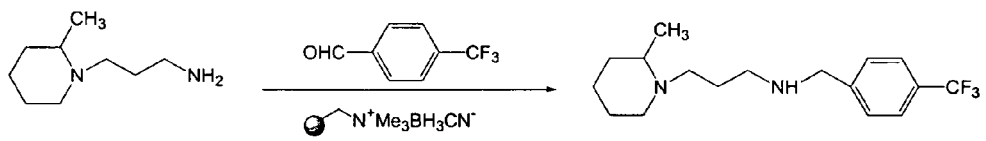

FIG. 20I: 1-(N-(4-Trifluorobenzyl)-3-Aminopropyl)pipecoline, compound # 712; MIC 12.5 uM; obtained from l-(3-aminopropyl)pipecoline and $\alpha,\alpha,\alpha$-trifluoro-p-tolualdehyde.

Figure 20J:
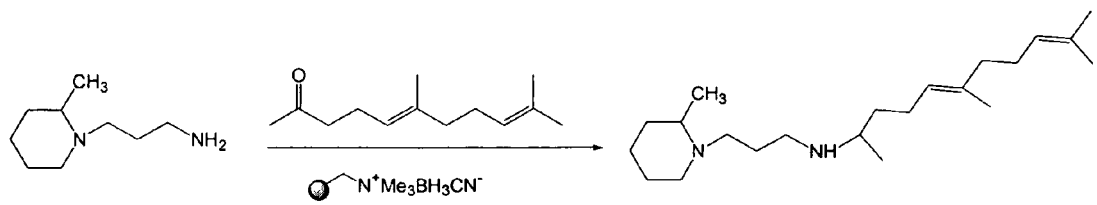

FIG. 20J: 1-(N-Geranyl)-3-Aminopropylpipecoline, compound #711; MIC 6.25 uM; obtained from 1-(3-aminopropyl)-pipecoline and geranylacetone.

The present application provides a diverse library of diamine compounds synthesized in one step from commercially available diamines and carbonyl compounds by solution phase reductive alkylation reaction using a polymer-supported trimethylammonium cyanoborohydride. Screening of the library against M. tuberculosis has revealed approximately 143 hits with the MIC equal or less than 12.5 μM. The most active hits have been re-synthesized on a lager scale, purified and tested in vitro and in vivo assays. New perspective scaffolds (homopiperazine, substituted piperazine, 4-(aminomethyl)piperidine, 2-(4-aminophenyl) ethylamine, 4,4'-methylenebis(2-methylcyclohexylamine) for synthesis of compounds with anti-TB activity have been identified. Two compounds, N,N'-bis(2-adamantyl)homopiperazine (SQ775) and N -benzyl-N'-(4-benzyloxy)benzylpiperazine (SQ786), are shown to have promising activity against M.tb in vivo.

Formulations

Therapeutics, including compositions containing the diamine compounds of the present invention, can be prepared in physiologically acceptable formulations, such as in pharmaceutically acceptable carriers, using known techniques. For example, a substituted ethylene diamine compound is combined with a pharmaceutically acceptable excipient to form a therapeutic composition.

The compositions of the present invention may be administered in the form of a solid, liquid or aerosol. Examples of solid compositions include pills, creams, soaps and implantable dosage units. Pills may be administered orally. Therapeutic creams and anti-mycobacteria soaps may be administered topically. Implantable dosage units may be administered locally, for example, in the lungs, or may be implanted for systematic release of the therapeutic composition, for example, subcutaneously. Examples of liquid compositions include formulations adapted for injection intramuscularly, subcutaneously, intravenously, intraarterially, and formulations for topical and intraocular administration. Examples of aerosol formulations include inhaler formulations for administration to the lungs.

A sustained release matrix, as used herein, is a matrix made of materials, usually polymers, which are degradable by enzymatic or acid/base hydrolysis, or by dissolution. Once inserted into the body, the matrix is acted upon by enzymes and body fluids. The sustained release matrix is chosen desirably from biocompatible materials, including, but not limited to, liposomes, polylactides, polyglycolide (polymer of glycolic acid), polylactide co-glycolide (coplymers of lactic acid and glycolic acid), polyanhydrides, poly(ortho)esters, polypeptides, hyaluronic acid, collagen, chondroitin sulfate, carboxylic acids, fatty acids, phospholipds, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide.

The dosage of the composition will depend on the condition being treated, the particular composition used, and other clinical factors, such as weight and condition of the patient, and the route of administration. A suitable dosage may range from 100 to 0.1 mg/kg. A more preferred dosage may range from 50 to 0.2 mg/kg. A more preferred dosage may range from 25 to 0.5 mg/kg. Tablets or other forms of media may contain from 1 to 1000 mg of the diamine composition. Dosage ranges and schedules of administration similar to ethambutol or other anti-tuberculosis drugs may be used.

The composition may be administered in combination with other compositions and procedures for the treatment of other disorders occurring in combination with mycobacterial disease. For example, tuberculosis frequently occurs as a secondary complication associated with acquired immunodeficiency syndrome (AIDS). Patients undergoing AIDS treatment, which includes procedures such as surgery, radiation or chemotherapy, may benefit from the therapeutic methods and compositions described herein.

The following specific examples will illustrate the invention as it applies to the particular synthesis of the substituted ethylene diamine compounds, and the in vitro and in vivo suppression of the growth of colonies of M. tuberculosis. In addition, the teachings of R. Lee et al. J. Comb. Chem 2003, 5, 172-187 are hereby incorporated by reference in their entirety. It will be appreciated that other examples, including minor variations in chemical procedures, will be apparent to those skilled in the art, and that the invention is not limited to these specific illustrated examples.

EXAMPLE I

The following methods and protocols were generally used for synthesis and analysis of the novel diamine compositions of the present invention.

Preparation of the Library: General Methods

All reagents were purchased from Sigma-Aldrich (St. Louis, Mo., USA). (Polystyrylmethyl)trimethylammonium cyanoborohydride was obtained from NovaBiochem (Darmstadt, Germany). Solvents 1,2-dichloroethane (DCE), dichloromethane, and methanol were purchased from Aldrich and used as received. Solution phase syntheses were performed using combinatorial chemistry equipment (Whatman Polyfiltronics (Rockland, Mass., USA) and Robbins Scientific, (Sunnyvale, Calif., USA)). Evaporation of the solvents was done using SpeedVac AES (Thermo Electron Corporation, Massachussettes, USA). Mass spectra data were obtained by Electrospray Ionization technique on Perkin Elmer/Sciex, API-300, TQMS (Wellesley, Mass.) with an autosampler.

Generating the Library/General Synthetic Procedure

Sixty commercially available diamines (FIGS. 1-4) were reductively alkylated with 64 of aldehydes and 20 ketones in presence of resin bound trimethylammonium cyanoborohydride, Scheme 1. Syntheses were carried out using 96-deep (2 ml) well chemically resistant plates, one reaction plate per group. Prior to the synthesis, selected carbonyl compounds were organized in 96-well format (Table 2) to yield a master plate of 1.2 M solutions in DCE.

All sixty diamines were separated in four groups based on their steric and electronic characteristics, FIGS. 1-4. Each diamine was measured in the amount of 0.05 g (approximately 0.3 mmol) and pooled together with the others in the group. Obtained diamine mixtures were dissolved in 5 ml of 1,2-dichloroethane and used for the syntheses. Each well of the 96-well filterplates was loaded with 0.2 ml of 1:10 mixture of acetic acid:DCE, 0.03 ml of the diamine mixture in DCE (group 1, group 2, group 3, or group 4) to assure 0.04 mmol of the diamines per well, and shaken for 5 min at room temperature. Appropriate carbonyl compounds from the master plate (0.1 ml of 1.2 M solution) were added into corresponding wells of the reaction plates followed by the addition of (polystyrylmethyl)trimethylammonium cyanoborohydride, (0.020 g, 0.08 mmol per well). The reaction plates were sealed and placed on a shaker. The reaction was allowed to proceed 24-36 hours at room temperature. At the end, the reaction mixtures were filtered using a filtration manifold, and products were collected into four (one per group) collection plates. Solvents were evaporated in SpeedVac and formed residues were analyzed by mass spectrometry prior to biological screening. Mono and double alkylated products were observed in 1:0.5 to 1:2 ratios by mass spectral analysis.

Screening of the Library: MIC Protocol

1. Grow H37Rv strain of Mtb in 7H9 media to a density of 0.2 OD at 600 nm.
2. Dilute culture 1:100 in 7H9.
3. Prepare a stock solution of Isoniazid (32 μg/ml in 7H9 media).
4. Prepare a stock solution of Ethambutol (32 μg/ml in 7H9 media).
5. All compounds to be tested are in 10 mM solution in MeOH.
6. Add 100 μl 7H9 medium to all wells in a round bottom 96 well plate.
7. Add 80 μl 7H9 medium to the first wells in rows C through H.
8. To well A1 add 100 ul INH soln (32 μg/ml).
9. To well B1 add 100 ul EMB soln (32 μg/ml).
10. To C1 through H-1 add 20 ul of compounds 1,2,3,4,5 or 6 respectively.
11. Perform a dilution series across each row by mixing and transferring 100 μl to the subsequent well. Discard the 100 μl from each well in the last column. Change tips after each transfer.
12. Add to each well on the plate 100 μl of the diluted H37Rv strain of Mtb.
13. Cover the plate and incubate at 37 C for 10 days.
14. Read plates for growth or non-growth using an inverted plate reader. MIC is considered to be the lowest concentration of drug that inhibits visible growth of Mtb.

Plate layout:

Concentrations in each well (μM)

| Drug | | | | | | | | | | | | |
|---|---|---|---|---|---|---|---|---|---|---|---|---|
| INH | 58.25 | 29.13 | 14.56 | 7.28 | 3.64 | 1.82 | 0.91 | 0.45 | 0.23 | 0.11 | 0.06 | 0.03 |
| EMB | 28.75 | 14.38 | 7.19 | 3.60 | 1.80 | 0.90 | 0.45 | 0.22 | 0.11 | 0.06 | 0.03 | 0.01 |
| Cpmd | 500 | 250 | 125 | 62.5 | 31.25 | 15.63 | 7.81 | 3.91 | 1.96 | 0.98 | 0.49 | 0.24 |

High-throughput Screening Lux Assay Protocol

1. Analogs to be tested are dried down in a speed vacuum to an approximate concentration of 6.3 μmoles/well.
2. Resuspend each analog with 200 μl methanol for a concentration of 31.5 mM.
3. A solution of 200 μM is made for each analog (a 1:15.75 dilution of the 31.5 mM stock followed by a 1:10 dilution) in 7H9 broth medium.
4. Using an opaque 96-well plate (Dynex, Microlite 1+), add 50 ul of each test analog to the first well of a row.

5. Add 25 µl 7H9 broth medium to wells 2-12 in each row.
6. Serially dilute the analogs from well 1 by transferring 25 µl through well 11, discarding the extra 25 µl from well 11.
7. Repeat for each row.
8. Well 12 is used as a growth control to assess background activity by the reporter strain.
9. Cover plate with adhesive film and incubate at 37 C for 24 hrs.
10. Prepare following substrates fresh immediately prior to use: Buffer (50 mM HEPES pH 7.1, 0.4% Triton X-100), 1M DTT, 10 mg/ml luciferin in DMSO.
11. Add 0.25 ml of 1M DTT and 14 µl 10 mg/ml luciferin in DMSO to each 5 ml of buffer to be used (5 ml/96-well plate).
12. Remove plates from incubator minimizing exposure to fluorescent lights.
13. Add 50 µl of substrate from step 11 to each well and measure luminescence immediately using TopCount NXT luminometer (5 s/well).

EXAMPLE 2

In vitro Efficacy Studies

The following methods and protocols were generally used for the in vitro analysis of the novel diamine compositions of the present invention.

Methods. In vitro Testing.

Cytotoxicity The Vero cell line (ATCC CCL-8 1) was seeded overnight at $5\times10^4$ cells per well in 96-well plates at 37° C. and 5% $CO_2$ in EMEM with essential amino acids and glutamine (BioFluids) supplemented with 10% heat-inactivated fetal bovine serum (FBS). Cells were exposed to dilutions of experimental and control drugs in triplicate for 72 hr, with each compound at a range of concentrations from 15-200 µM. Chlorpromazine (Sigma) was run as a control at the same concentrations. CellTiter 96 AQueous Assay (Promega) was used for determination of Vero cell viability. Briefly, a solution of MTS salt (3-(4,5-dimethylthiazol-2-yl)-5-(3-carboxymethoxyphenyl)-2-(4-sulfophenyl)-2H-tetrazolium) and phenazine methosulfate was added to each well and plates were incubated for 2 hr at 37° C. and 5% $CO_2$. Absorbance of each well was read using BioRad microplate reader at 490 nm. Viability (absorbance) of cells in drug-exposed wells was compared to those in drug-free control wells, and a curve relating cell viability to drug concentration was created.

Activity in macrophages: The RAW 264.7 (ATCC TIB-71) murine macrophage cell line was seeded overnight at $5\times10^5$ cells/well in 24-well plates at 37° C. and 5% $CO_2$ in DMEM with essential amino acids and glutamine (BioFluids) supplemented with 10% heat-inactivated FBS. Log-phase cultures of recombinant *M. tuberculosis* H37Rv containing the luciferase reporter construct pSMT1 [24] were grown in Middlebrook 7H9 (Difco) supplemented with BSA, dextrose, catalase, and 50 µg/ml of hygromycin B (Roche) at 37° C. with 5% $CO_2$ from frozen stocks. *Mycobacteria* were harvested by centrifugation at 2,500×g for 10 min and washed twice with serum-free DMEM before re-suspension in DMEM supplemented with 5% heat-inactivated FBS at $5\times10^6$ cells/ml. Macrophages were infected by incubation with an MOI of 10:1 *M. tuberculosis*:cell overnight at 37° C.; they were then washed three times in Dulbecco's PBS (Biofluids). Infected cells were treated in duplicate with compounds in DMEM/5% FBS at 37° C. with 5% $CO_2$ at the MIC of each compound for 1, 2, 3 and 6d. Macrophage cells were lysed by the addition of 1 ml/well sterile distilled $H_2O$ containing 0.1% Triton-X-100 with stirring for 2 min. One hundred (100) µl lysate was sampled from each well and an equal amount of 1% n-decyl aldehyde (Sigma) in ethanol was added. Luminescence was immediately quantified using a TopCount luminometer (Packard) with a dwell-time of 10 s per well.

EXAMPLE 3

In Vivo Efficacy Studies

Two homopiperazines SQ775 and SQ780 and one piperazine compound SQ786 (see FIG. 21), were tested for mycobacterial activity in mice using two models, and proved to be efficacious against *Mycobacterium tuberculosis* in vivo.

In Vivo Studies

*Mycobacterial inoculum:* An aliquot of a frozen stock of *M. tuberculosis* H37Rv Pasteur was thawed and added to 5 ml 7H9 broth medium supplemented with 0.2% glycerol, albumin dextrose complex (ADC) and 0.05% Tween 80, and incubated 1 wk at 37° C. One (1) ml was then added into 25 ml fresh medium (the 2nd passage) during wk 2. The culture was washed twice with PBS and 0.05% Tween 80, re-suspended in PBS with 0.5% BSA and 0.05% Tween 80, and aliquots were frozen at −80° C. To determine viable Colony-forming Units (CFU) of the frozen culture, an aliquot was thawed and 10-fold dilutions were plated on agar 7H9 and incubated at 37° C. CFU were determined 20 d later.

Mice: Female C57BL/6 mice, 8 wk old, were purchased from Charles River (Raleigh, N.C.). Mice were housed in the BSL-2 facility of BIOQUAL, Inc. (Rockville, Md.), and were allowed to acclimatize for at least 4 d prior to infection.

Chronic Model of TB Infection

Infection: A frozen sample of stock *M. tuberculosis* culture of known viability and CFU count was thawed and diluted to a concentration of approximately $5\times10^5$ CFU/ml. Mice were infected with *M. tuberculosis* H37Rv iv through lateral tail vein with $10^5$ CFU in 0.2 ml of PBS, and final concentration of CFU was confirmed by culture of a sample of the inoculum.

Drug treatment: Chemotherapy was initiated 20 d following infection and continued for 30 d. Drugs were administered by gavage, 200 □l per mouse, 5 d/wk. Diamine compounds were tested at 10 mg/kg; INH and EMB were given at 25 mg/kg and 100 mg/kg, respectively, and used as positive controls. On the day 30 after initiation of chemotherapy, one group of mice for every tested compound (6 mice per group) was sacrificed, and their lungs and spleens were removed and homogenized in sterile 2 ml PBS with 0.05% Tween-80. Organ homogenates were plated in 10-fold serial dilutions on 7H10 agar dishes, and were incubated at 37° C. CFU were calculated after 3 wk of growth.

Statistical Analysis: To analyze results of CFU in organs, we used the ANOVA test: significance of any differences was estimated by Student's T-test and $p<0.05$ was considered statistically significant.

At first, compounds were studied in a new rapid (3 wk) murine model that allows to predict quickly and with sufficient accuracy the drug's efficacy based on its ability to prevent body weight loss in the infected animals, one of the signs of TB severity [Nikonenko, et al, 2004. Antimicrob. Agents Chemother. in press]. Briefly, mice were inoculated iv with $10^6$ CFU of virulent *M. tuberculosis* H37Rv to develop a rapid and progressive TB disease. Chemotherapy was initiated 7 days after inoculation and continued for 10 days. Mice (6 per group) treated with INH, as well as uninfected animals and infected untreated placebo, were used as the controls. Tested drugs were administrated daily by gavage at a dose of 10 mg/kg.

Figure 22:
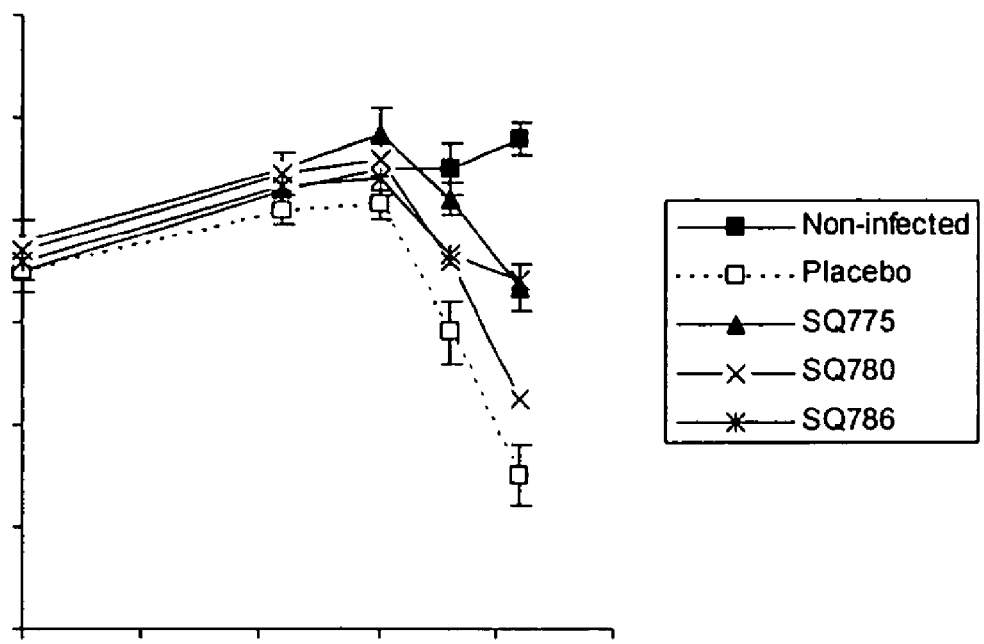
FIG. 22 provides data corresponding to rapid model testing assessing dynamics of body weight of mice treated with SQ 775, SQ780 AND SQ786.

Body weights of mice in all groups were monitored starting from time 0. By day 10, infected placebo control mice had started to lose weight and by day 20 mice in this group lost more than 25% of their body weight (sign of terminal illness), in contrast, treatment with SQ775 and SQ786 prevented body weight loss and delayed mortality, FIG. 22. In this model, mice treated with INH did not show any signs of body loss; also, no significant differences were seen when mice was treated with INH at 25 mg/kg (highly efficacious dose) vs 2.5 mg/kg. Compound SQ780 demonstrated low efficacy in this model.

Figure 23:
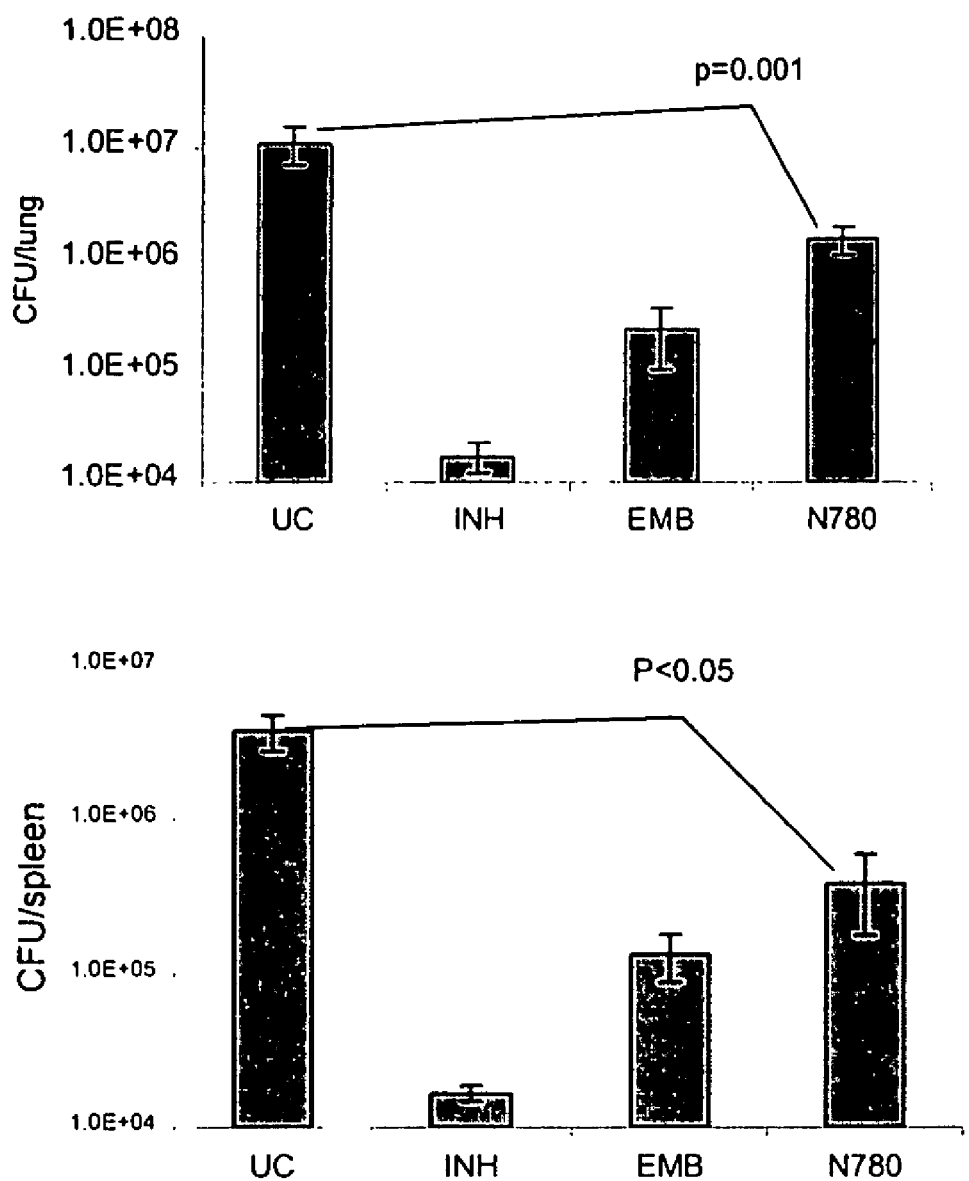
FIG. 23 provides anti-TB activity of SQ780 in lung and spleen of mice. Female C57BL/6 mice were i.v. infected with $10^5$ CFU *M.tuberculosis* H37Rv (museum strain). 20 days following infection mice were treated with anti-TB drugs for 4 weeks.

Compounds SQ775, SQ780, and SQ786 were then tested in a murine model of chronic TB well known to those skilled in the art for evaluation of new drugs and drug combinations [Kelly, et al, 1996. Antimicrob. Agents Chemother. 40:2809-2812]. Mice were infected iv with *M. tuberculosis* H37Rv and the infection was allowed to progress. Chemotherapy was initiated 20 days following infection. Mice treated with INH (25 mg/kg) and EMB (100 mg/kg) were used as positive controls, and infected mice that were untreated served as negative controls. Test compounds were administered daily by gavage for 28 days at a dose 10 mg/kg. At the end of therapy, a group of mice for every tested drug was sacrificed, and 10-fold dilutions of spleen and lung homogenates were plated on agar to determine CFU, see FIGS. 23 and 24.

Figure 24:
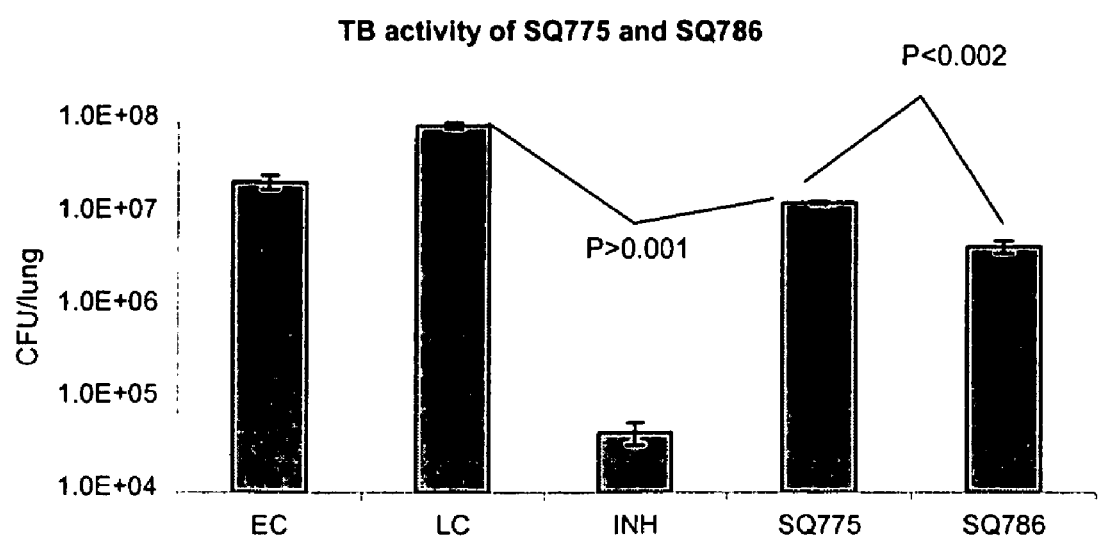
FIG. 24 provides a graph of the data demonstrating a reduction of bacterial CFU in lungs of mice as a result of chemotherapy. Female C57BL/6 mice were i.v. infected with $10^4$ CFU *M.tuberculosis* H37Rv previously passed thought C57BL/6 mice (lungs). Three weeks after infection chemotherapy with anti-TB drugs was initiated. Duration of treatment was 4 weeks. INH was used at 25 mg/kg, SQ775 and SQ786—at 10 mg/kg.

As shown in FIG. 24, a reduction of bacterial CFU in lungs of mice as a result of chemotherapy using SQ780. Female C57BL/6 mice were i.v. infected with $10^4$ CFU *M. tuberculosis* H37Rv previously passed thought C57BL/6 mice (lungs). Three weeks after infection, chemotherapy with anti-TB drugs was initiated. Duration of treatment was 4 weeks. MNH was used at 25 mg/kg, SQ775 and SQ786—at 10 mg/kg.

In the chronic model, all three compounds have shown 0.77-0.96 log reduction of the CFUs in lungs of infected and treated mice that is indicative of anti-TB activity (Tuberculosis Antimicrobial Acquisition and Coordinating Facility, www.tacf.org). Compound SQ780 was also able to reduce the CFU in spleen by 1 log. During testing of SQ775 and SQ786 spleens of the treated animals were not examined. In this chronic model, compound SQ775, SQ780, and SQ786 have shown similar activity despite the fact that SQ780 was not active in the initial in vivo rapid screen. This can be explained by the fact that during conducted in vivo studies of chronic TB infection in mice, compound SQ780 (unlike compounds SQ775 and SQ786) was tested using less virulent strain of M.tb,—museum strain of H37Rv, while compounds SQ775 and SQ786 were tested with M.tb H37Rv previously passed (derived) through the lungs of infected C57BL/6 mice.

EXAMPLE 4

Additional analysis of the diamine compositions were conducted according to the following methods and protocols.

Screening of the Library

Prepared library was screened for activity in vitro against *M. tuberculosis* (1) by direct determination of the MIC in a broth microdilution assay and (2) using a high-throughput screening assay that has a shared target with Ethambutol and other cell wall inhibitors such as Isoniazid and Ethioniamide, and contains recombinant mycobacteria with firefly luciferase encoded to the drug-inducible gene (Shawar, R. M. et al. *Antimicrob Agents Chemother* 1997, 41, 570-4.; Arain, T. M. et al. *Antimicrob Agents Chemother* 1996, 40, 1536-41; Lee, R. E., Barry, C. E., III, unpublished results)

Figure 25:
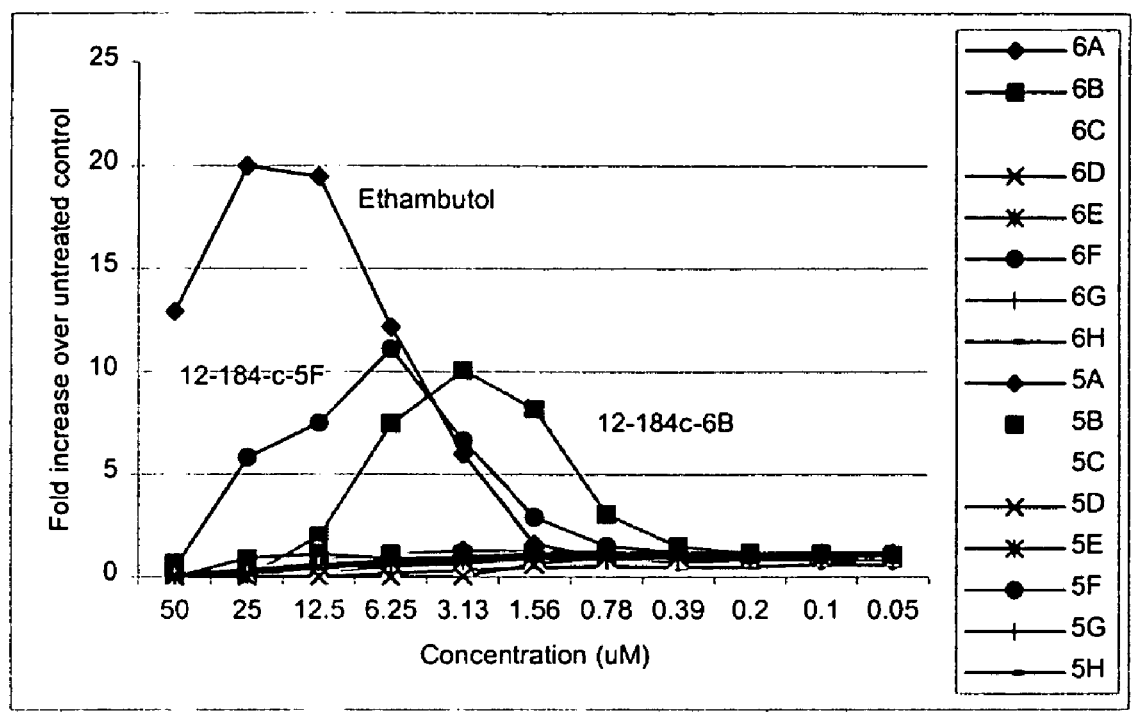
FIG. 25 provides a graph showing representative assay data in the luciferase reporter strain containing an Rv0341 promoter with serial dilution of 16 wells of a 96-well library plate representing about 240 individual compounds.

The diamines were tested (as prepared) in pools within a 50 µM to 0.18 nM range of concentrations per each individual compound based on an assumption that every synthesized compound was produced with theoretical yield of 100%; commercially available Ethambutol (of 99% purity) was used as a positive control in each assay, FIG. 25. Wells with an MIC equal to or less than 12.5 µM and/or activity in the luciferase assay that exceeded untreated control by 1.5 times were considered to be active and were selected for deconvolution.

Out of 336 synthesized compound mixtures, 176 showed antimycobacterial activity and were deconvoluted. During deconvolutions, individual compounds were re-synthesized in the 96-well format and tested for anti-TB activity in the same in vitro screening assays to yield 143 hits with the MIC equal or less than 12.5 µM. Among those, twenty-five compounds were also active in the Luc assay, Table A (below); half of them were derivatives of the Group 3 diamines. Group 2 and Group 3 gave the hits with good MIC values, but low activty in the luciferase assay. Group 4 was found to be the least productive among all diamines yielding upon deconvolutions of 40 active mixtures only 2 hits with the MIC of 12.5 µM that can be explained by additive effects of individual compounds contributing to the activity or variations in the dilutions.

TABLE A

Screening results of synthesized mixtures and individual compounds.

| Diamines | Active mixtures | Hits | Hits active in both assays |
|---|---|---|---|
| Group 1 | 56 | 65 | 5 |
| Group 2 | 48 | 49 | 7 |
| Group 3 | 32 | 27 | 15 |
| Group 4 | 40 | 2 | 0 |
| Total actives | 176 | 143 | 27 |

SAR Evaluation

Figure 26:
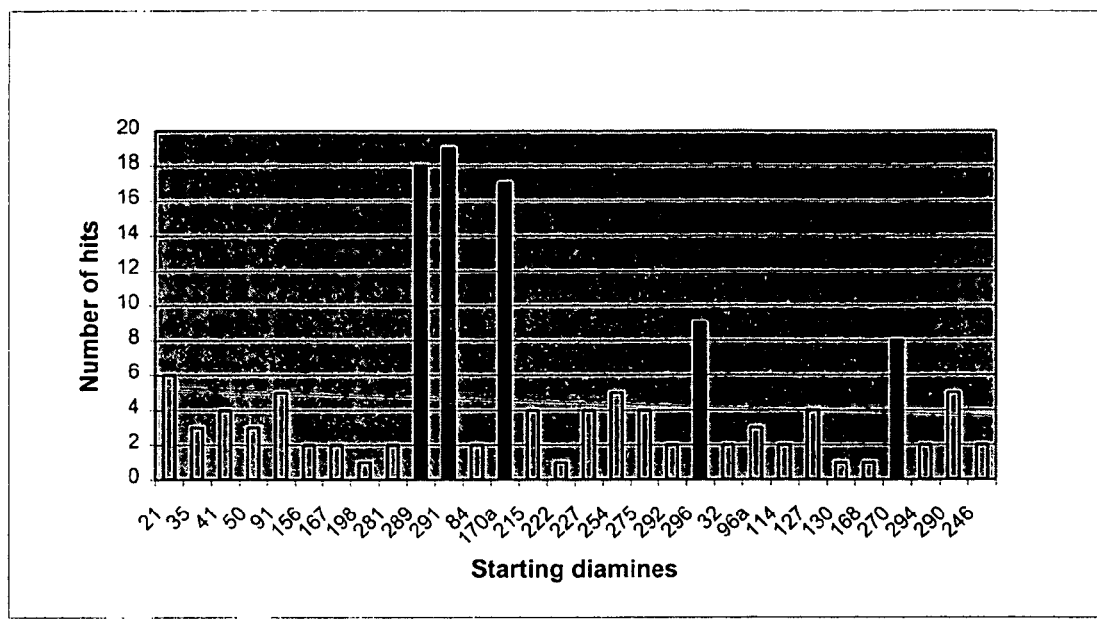
FIG. 26 provides a graph showing the occurrence of the starting diamines in the molecules that are active in at least one screening assay. Among the most frequently occurring are 4,4'-methylenebis(cyclohexylamine) (marked as 289), 4,4'-methylenebis(2-methylcyclohexylamine) (291), 2-(4-aminophenyl)ethylamine (170.a), 4-(aminomethyl)piperidine (296), and homopiperazine (270).
Figure 27:
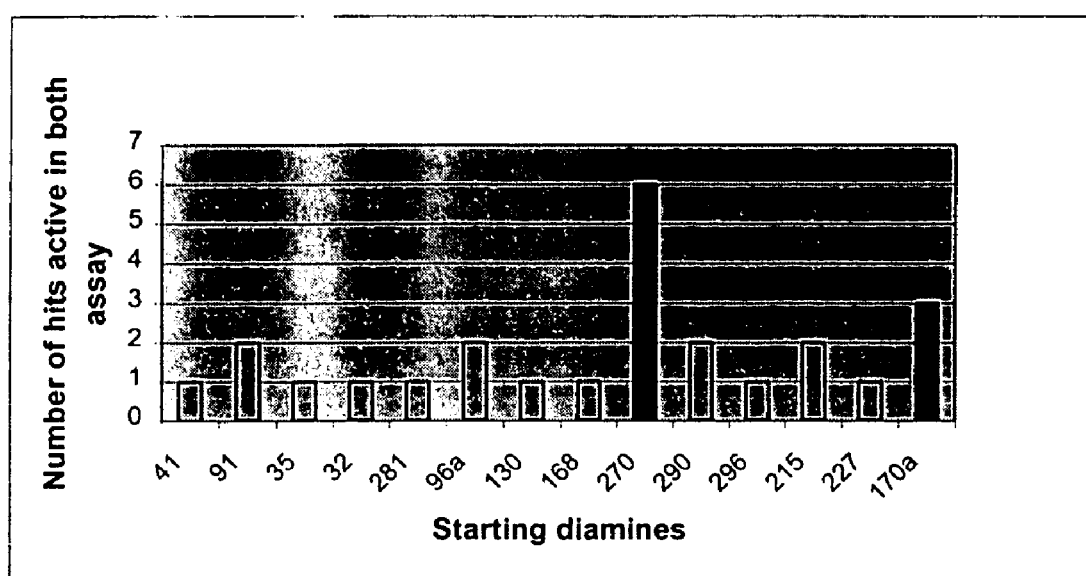
FIG. 27 provides a graph showing the occurrence of starting diamines in the hit compounds active in both screening assays (the MIC 12.5 µM or less after the deconvolutions). Diamines: homopiperazine (270), 2-(4-aminophenyl)ethylamine (170.a).
Figure 28:
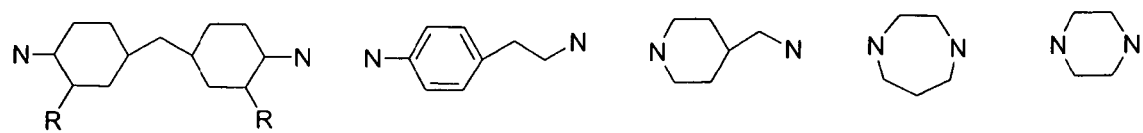
FIG. 28 provides chemical scaffolds with antimycobacterial activity.

We found that the vast majority of the hits derived from five diamines: 4,4'-methylenebis(cyclohexylamine) (d-289) and its analogue 4,4'-methylenebis(2-methylcyclohexylamine) (d-291), 2-(4-aminophenyl)ethylamine (d-170.a), 4-(aminomethyl)piperidine (d-296), and homopiperazine (d-270), FIGS. 26-28.

Both biscyclohexylamines yielded at least thirty-seven hits, but not a single one was active in the luciferase assay (FIG. 27), suggesting a different target or overall toxicity of this class of compounds. Similarly, very few compounds derived from 2-(4-aminophenyl)ethylamine and 4-(aminomethyl)piperidine had showed activity in both screening assays. Homopiperazine scaffold was found to be of the most interest since it produced eight hits with the MIC of 12.5 µM or less, and six of those compounds showed significant activity in the Luc assay. Substituted piperazines should also be noted as substantially contributing to antimycobacterial activity, FIG. 28: when combined, 1-(2-aminoethyl)piperazine (d-41), 1-(2-fluorophenyl)piperazine (d-96.1), 1-piperonylpiperazine (d-114), 1-(4-fluorophenyl)piperazine (d-168), 1-amino-4-(2-hydroxyethyl)piperazine (d-246), and 1-benzylpiperazine (d-290) gave nineteen hits with six being active in both screening assays (FIGS. 26 and 27).

Figure 29:
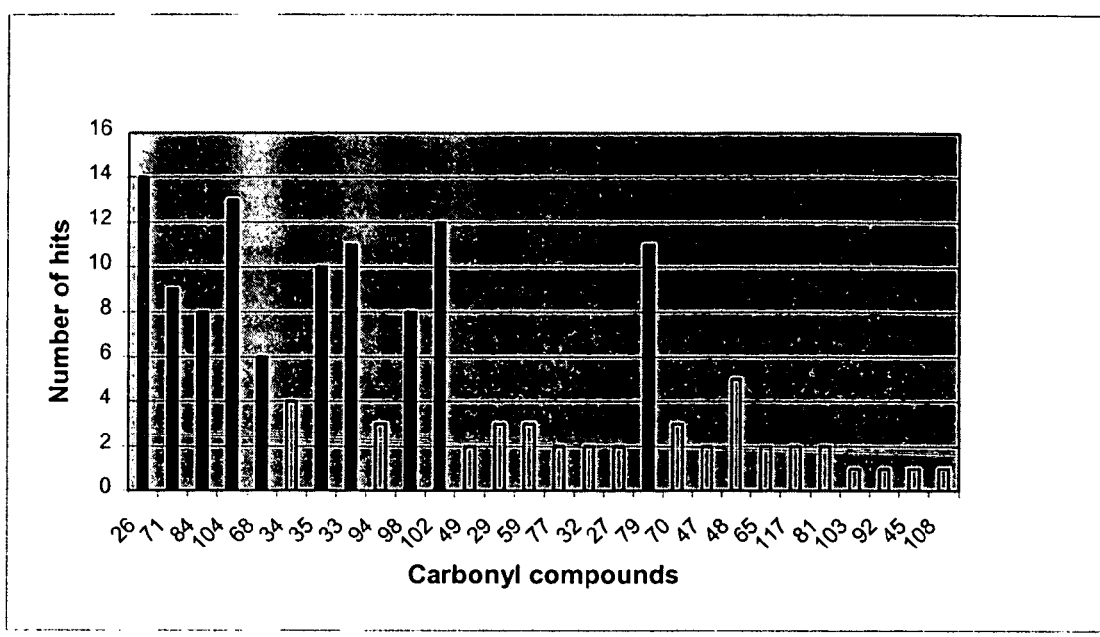
FIG. 29 provides carbonyl compounds that have contributed into antimycobacterial activity of the final products. Among the most frequently occurring are 4-benzyloxybenzaldehyde (marked as 26), 2-methoxy-1-naphthaldehyde (71), (S)-(–)-perrilaldehyde (84), geranylacetone (104), 4-isopropylbenzaldehyde (68), citronellal (c-35), 5-(4-chlorophenyl)furfural (33), 2-adamantanone (c-98), decalone (c-102), (–)-myrtenal (79).

Among carbonyl compounds that produced most of the hits (FIG. 29) were 4-benzyloxybenzaldehyde (c-26), 5-(4-chlorophenyl)furfural (c-33), decalone (c-102), 2-methoxy-1-naphthaldehyde (c-71), (S)-(−)-perrilaldehyde (c-84), and citronellal (c-35). We have also found similarities with the 1,2-ethylenediamine series: some hits in this diamine library contained identified earlier myrtenyl, geranyl and adamantane fragments derived from (−)-myrtenal (c-79), geranylacetone (c-104), and 2-adamantanone (c-98). (Lee et al. *J. Comb. Chem.* 5:172-187.)

Homopiperazine and Piperazine Series.

After identification of pharmacophores with antimycobacterial activity, FIG. 28, we focused our efforts on homopiperazine series due to the fact, that they had demonstrated significant activity against M.tb. in both the MIC and the Luc assay, and were readily accessible. Eight symmetrically substituted homopiperazines SQ775-SQ782 of at least 90% purity (by MS) were prepared on 150-200 mg scale with 45-96% yield by the same route but using either stochiometric amounts of the reagents or little excess of carbonyl compound to the starting homopiperazine, Table B (below). To select candidates for in vivo efficacy testing in mice, synthesized compounds were evaluated for (i) antimycobacterial activity in vitro, (ii) cytotoxicity, and later (iii) for effectiveness against intracellular M.tb. in macrophages.

Determined by the same microdilution method, the MICs of purified hits were within a 3.9-7.8 µM range (except SQ776 and SQ781) and mostly re-confirmed, Table 3. In vitro cytotoxicity of active compounds was determined using HepG2 cell line in a MTS assay yielding IC50 values for each compound and Selectivity Index, SI, the ratio IC50 to MIC, as an estimate of a therapeutic window, Table 3. Top compounds were SQ775, SQ779, SQ780, and SQ782, all with SI greater than 10. To evaluate lipophilicity of the hits in this series, we calculated the octanol/water partition coefficient logP using commercial software and the services of ACD (www.acdlabs.com). In general, all synthesized homopiperazines in the study demonstrated high logP values, and for some hits the logP was greater than 6.

At this point, five compounds were dropped due to high MIC (SQ776, SQ781), poor activity in Luc assay (SQ776), low SI values (SQ776, SQ781), and/or high logP (SQ776-SQ779, SQ781), and compounds SQ775 (MIC 6.25 µM, SI 16.92, logP 5.98), SQ780 (MIC 1.56 µM, SI 18.21, logP 4.04), and SQ782 (MIC 6.25 µM, SI 13.46, logP 2.98) were advanced into further testing.

To be studied along with those selected compounds, we also added compound SQ786, as a representative of the hits with a piperazine scaffold. This compound showed MIC of 3.9 µM, relatevely low cytotoxicty (HepG2 cells, 54 µM), high Selectivity Index SI of 17.25, and acceptable for good oral bioavailability [5] logP value of 4.02, Table B. But unlike its higher homologues, SQ786 was not active in the Luc assay that is indicative of a target other than a cell wall.

TABLE B

Structure and in vitro data of selected hits. Results of the Luc assay are reported in % LCPS compared to EMB at 3.1 µM.

| # | Structure | MIC µM | IC 50 µM | SI IC50:MIC | Luc | LogP |
|---|---|---|---|---|---|---|
| SQ775 | 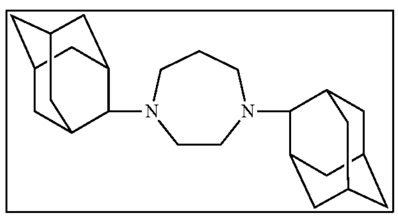 | 7.8 | 132 | 16.92 | 0.95 | 5.98 +/− 0.35 |
| SQ777 | 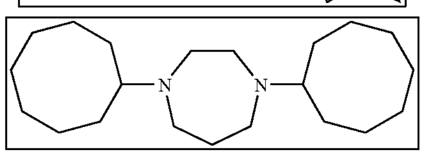 | 7.8 | 74 | 9.49 | 1.02 | 6.57 +/− 0.31 |
| SQ778 | 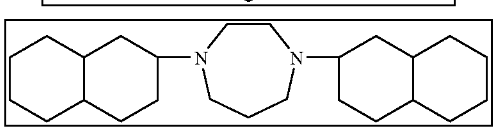 | 7.8 | 54 | 6.92 | 0.94 | 7.40 +/− 0.33 |
| SQ779 | 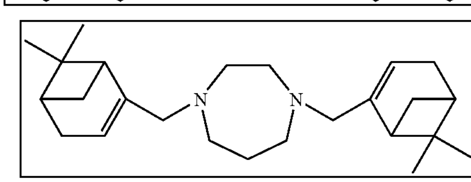 | 7.8 | 110 | 14.10 | 0.68 | 6.99 +/− 0.44+ |
| SQ780 | 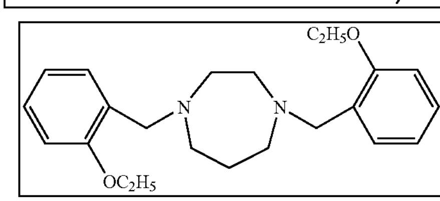 | 3.9 | 71 | 18.21 | 0.88 | 4.04 +/− 0.62 |

TABLE B-continued

Structure and in vitro data of selected hits. Results of the Luc assay are reported in % LCPS compared to EMB at 3.1 µM.

| # | Structure | MIC µM | IC 50 µM | SI IC50:MIC | Luc | LogP |
|---|---|---|---|---|---|---|
| SQ782 | 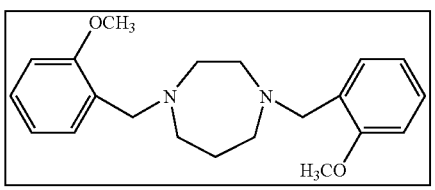 | 7.8 | 105 | 13.46 | 1.02 | 2.98 +/− 0.62 |
| SQ786 | 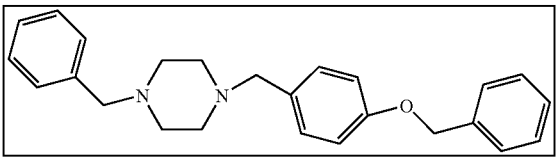 | 3.13 | 54 | 17.25 | 0. | 4.04 +/− 0.71 |

EXAMPLE 5

In vitro Evaluation

Figure 31:
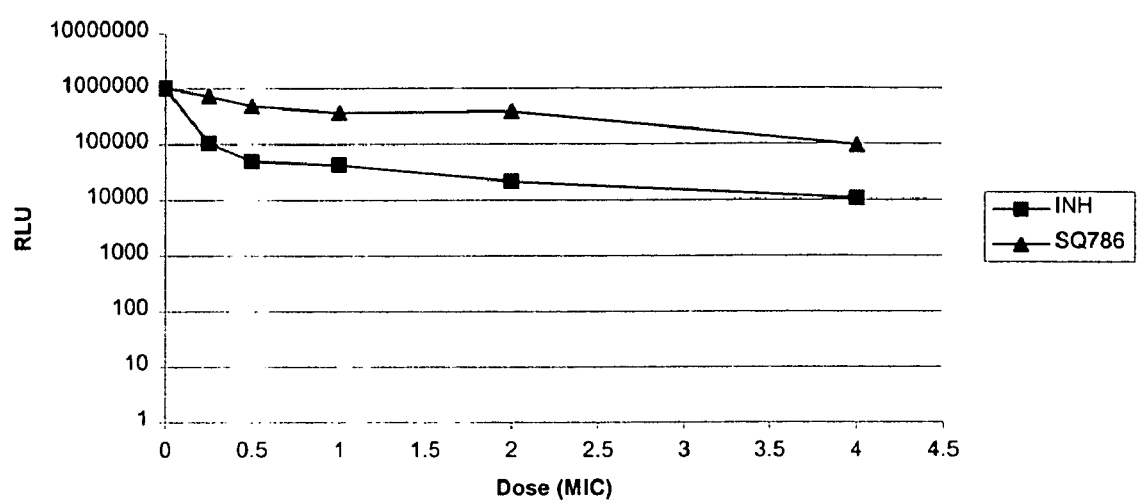
FIG. 31 provides a graph showing the inhibitory activity of INH and SQ786 against *M.tuberculosis* in TB-infected mouse macrophage RAW 264.7 cells at five concentrations. A bioluminescence-based assay with a reporter strain of *M. tuberculosis* was employed.

To somewhat predict their potency in vivo prior to actual testing in the animal models, SQ775, SQ780, SQ782, and SQ786 were evaluated for in vitro efficacy in TB-infected mouse macrophage RAW 264.7 cells. A bioluminescence-based assay that employed a reporter strain of *M. tuberculosis* were used for the screening so, that mycobacterial growth was estimated based on light production following addition of a drug to the infected cells. The cells were treated with the drugs for seven days at MIC, 0.25×MIC, 0.5×MIC, 2×MIC, and 4×MIC, and *M. tuberculosis* viability was measured on day 7 (one time point). Standard drugs EMB (MIC of 12.5 µM) and INH (MIC of 1 µM) served as positive controls. In intracellular environment, compounds SQ780, SQ782, and SQ786 demonstrated at least 90% inhibition of bacterial growth (FIGS. 30 and 31), and SQ775 has reached 99% level at the concentration 2×MIC (FIG. 30). Compounds SQ782 and SQ780 were equivalent to or better than EMB, but less active than INH (FIG. 30).

EXAMPLE 6

In Vivo Evaluation

Having shown a substantial intracellular *M. tuberculosis* inhibitory activity, compounds SQ775, SQ780, and SQ786 were evaluated for in vivo efficacy in a new rapid (3 wk) murine model of TB (Nikonenko, AAC, 2004), that allows to predict quickly and with sufficient accuracy the drug's efficacy based on its ability to prevent body weight loss in the infected animals, one of the signs of TB severity.

Figure 32:
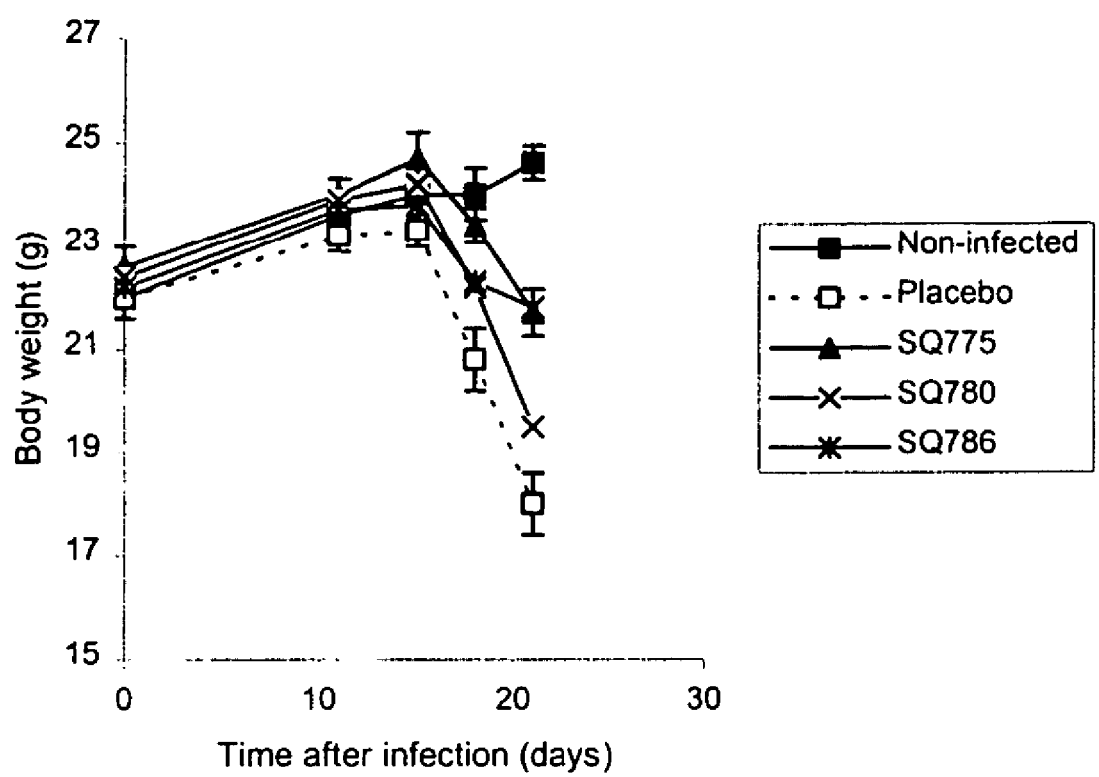
FIG. 32 provides a graph showing data collected using the rapid model evaluation technique used to measure the dynamics of body weight of mice treated with SQ775, SQ780, and SQ786.

Briefly, mice were inoculated iv with $10^6$ CFU of virulent *M. tuberculosis* H37Rv to develop a rapid and progressive TB disease. Chemotherapy was initiated 7 d after inoculation and continued for 10 days. Mice (6 per group) treated with INH, as well as uninfected animals and infected untreated placebo, were used as the controls. Tested drugs were administrated daily by gavage at a dose of 10 mg/kg. Body weights of mice in all groups were monitored starting from time 0. By 10 d, infected placebo control mice had started to lose weight and by 20 d mice in this group lost more than 25% of their body weight (sign of terminal illness), while treatment with SQ775 and SQ786 prevented body weight loss and delayed mortality. (As a footnote or reference: In this model, mice treated with INH did not show any signs of there is no significant differences were seen INH, administered at 25 mg/kg (highly efficacious dose) as well as at 2.5 mg/kg), FIG. 32. By day 21 following challenge mice treated with SQ780 lost 13% of their initial body weight, but mice that were cured with SQ775 lost 4% of their initial body weight. For this group of 6 mice chemotherapy was withdrawn and body weight was monitored for another 18 days. One week after chemotherapy withdrawn 3 mice died and 3 mice remained alive. So mortality in the group was 50%. Ten days later the rest 3 mice that remained alive lost about 20% of their initial body weight and were sacrificed.

Based on data obtained from our in vitro and in vivo studies compounds SQ775 and SQ786 have been advanced into further testing, including their evaluation in an accepted murine model of chronic TB infection that is in progress.

We claim:

1. A method for treating tuberculosis in an animal comprising administering to the animal an effective tuberculosis-treating amount of a compound selected from Compound 775

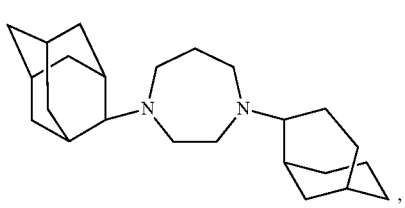

-continued
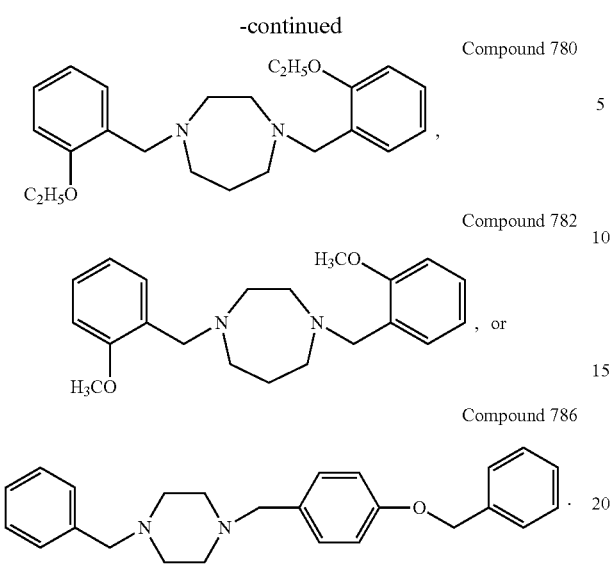
Compound 780
Compound 782
Compound 786
2. The method of claim 1, wherein the compound is
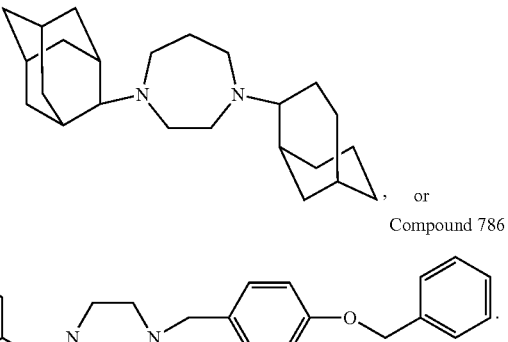
Compound 775
Compound 786
3. The method of claim 2, wherein the animal is a human.
* * * * *